United States Patent [19]
Ellis et al.

[11] Patent Number: 5,824,501
[45] Date of Patent: Oct. 20, 1998

[54] NUCLEIC ACIDS OF THE BLOOM'S SYNDROME GENE

[75] Inventors: Nathan A. Ellis; James German, both of New York, N.Y.; Joanna Groden, Cincinnati, Ohio

[73] Assignees: New York Blood Center, New York, N.Y.; University of Cincinnati, Cincinnati, Ohio

[21] Appl. No.: 559,303

[22] Filed: Nov. 15, 1995

[51] Int. Cl.⁶ .......................... C12N 15/12; C12N 15/63; C12N 15/00; C07H 21/04

[52] U.S. Cl. ................ 435/69.1; 435/252.3; 435/254.11; 435/325; 435/320.1; 435/172.3; 536/23.1; 536/23.2; 536/23.5

[58] Field of Search .......................... 435/6, 69.1, 320.1, 435/325, 252.3, 254.11, 172.3; 536/23.1, 23.2, 23.5

[56] References Cited

PUBLICATIONS

James German, M.D., entitled "Bloom Syndrome: A Mendelian Prototype of Somatic Mutational Disease," Medicine, vol. 72, No. 6, pp. 393–406 Nov. (1993).

Nathan A. Ellis et al., entitled "The Bloom's Syndrome Gene Product Is Homologous to RecQ Helicases," Cell, vol. 83, pp. 655–666, Nov. 17, 1995.

Eberhard Passarge, entitled "A DNA helicase in full Bloom", Nature Genetics, vol. 11, pp. 356–357 Dec. (1995).

Puranam et al., "Cloning and characterization of RECQL, a potential human homologue of the *Escherichia coli* DNA helicase RecQ.", J. Biol. Chem. 269(47):29838–29845, Nov. 1994.

*Primary Examiner*—Jasemine C. Chambers
*Assistant Examiner*—Scott D. Priebe
*Attorney, Agent, or Firm*—Amster, Rothstein & Ebenstein

[57] ABSTRACT

The present invention provides a method for diagnosing BS as well as determining whether a subject is a carrier of a mutated BLM gene. The present invention also provides one or more single-stranded nucleic acid probes and antibodies which may be formulated in kits, and used for diagnosing BS or determining whether a subject is a carrier of a mutated BLM gene. In addition, the present invention provides a method for treating or preventing the onset of BS in a subject in need of such treatment or prevention, as well as vectors and stem cells useful for such treatment or prevention. The present invention also provides a purified and isolated nucleic acid encoding an enzymatically active BLM protein, a vector comprising this nucleic acid, a cell stably transformed with this vector, as well as a method for producing recombinant, enzymatically active BLM protein. A purified, enzymatically active BLM protein is also provided by the present invention. Finally, the present invention provides a vector, an embryonic stem cell, and a non-human, transgenic animal, each of which comprises a mutated BLM gene, as well as a method for producing the non-human, transgenic animal.

15 Claims, 11 Drawing Sheets

FIG. 2A

```
323  K  D  L  D  T  S  D  R  K  E  D  V  L  S  T  S  K  D  L  L  S  K  P  E  K  M  S
     TATGCAGGAGCTGAATCCAGAAGCAGCACAGACTGTGACGCTAGACAGATAAGTTTACAGCAGCTTATTCAGTGA 1200
350  M  Q  E  L  N  P  E  T  S  T  D  C  D  A  R  Q  I  S  L  Q  Q  Q  L  I  H  V
     TGGAGCAGCACATCTGTAAATCCTGAAACTAGTACTGATTGTGATGCTAGACAGATAAGCCTACAACAGCAGCTTATACATGTCTCAG 1280
376  M  E  H  I  C  K  L  I  D  T  I  P  D  D  K  L  K  L  L  D  C  G  N  E  L  L  Q
     CAGCGGAACATAGAAGAAACTCTAACGGAAGATTTTAATAAAAGTGATGCCAGTCTCTTGGCTCTTCATTGTGGAG 1360
403  Q  R  N  I  R  R  K  L  T  E  V  D  F  N  K  S  D  A  S  L  L  G  S  L  W  R
     ATACAGGCCTGATTCACTTGAGGCCCTATGGAGGGTGATTCTGCCCTACAGGAATTCTATGAAGGAGTTAAATTTTT 1440
430  Y  R  P  D  S  L  D  G  P  M  E  G  D  S  C  P  T  G  N  S  M  K  E  L  N  F
     CACACCTTCCCTCAAATTCTGTTTCCTCGGGACTGTTTACTGACTAGAAAGACAGGATTCTCTGCCACC 1520
456  S  H  L  P  S  N  S  V  S  P  G  D  C  L  T  T  T  L  G  K  T  G  F  S  A  T
     AGGAAGAATCTTTTTGAAGGCCCTTTATTCAATACCATTTACAGAAGTCCTTGTAAGTAGCAACTGGGCTGAAACACC 1600
483  R  K  N  L  F  E  R  P  L  F  N  T  H  L  Q  K  S  F  V  S  S  N  W  A  E  T  P
     AAGACTAGAAAATGAAAAAAATGAAAGCTCTTATTCCCAGAAATGTTCTGTGAAGATCAGAATAAAC 1680
510  R  L  G  K  K  N  E  S  S  Y  F  P  G  N  V  L  T  S  T  A  V  K  D  Q  N  K
     ATACTGCTTCAATAAATGACTTAGAAAGAGAAACCCAACTTCCTATGATATTTGATAATTTGATATAGTGACTTTGAT 1760
536  H  T  A  S  I  N  D  L  E  R  E  T  Q  P  S  Y  D  I  D  N  F  D  I  D  D  F  D
     GATGATGATGACTGGGAAGACATAATGCATAATTTAGCAGCTGCCTATCAACCATCAAGGA 1840
563  D  D  D  W  E  D  I  M  H  N  L  A  A  S  K  S  S  T  A  A  Y  Q  P  I  K  E
     AGTGTCGGCCAATTAAATCAGTATCAGAAGACTTTCCTCAGCTGTCTTCCAGTGTCATCTACTGCTCAAA 1920
590  G  R  P  I  K  S  V  S  E  R  L  S  S  A  K  T  D  C  L  P  V  S  S  T  A  Q
     ATATAAACTTCTCAGAGTCAATTCAGAATTACTGACAAGTCAGCAAAATTTAGCACAAAATTTAGAAATCTGAAACATGAG 2000
616  N  I  N  F  S  E  S  I  Q  N  Y  T  D  K  S  A  Q  N  L  A  S  R  N  L  K  H  E
     CGTTTCCAAAGTCTTAGTTTTCCTCATACAAAGAAAATGATGAAGATTTCATAAAAATTTGGCCTGATAATTTTAG 2080
643  R  F  Q  S  L  S  F  P  H  T  K  E  M  M  K  I  F  H  K  F  G  L  H  N  F  R
     AACTAATCAGCTAGAGGCAATCAATGCTGCTTGGTGAAGACTGTTTATCCTGATGCCGACTGAGGTGTGGTAAGA 2160
670  T  N  Q  L  E  A  I  N  A  A  L  L  G  E  D  C  F  I  L  M  P  T  G  G  K
     GTTTGTGTTACCAGCTCCCTGCGTGTTCCCTTGCATTTCCCTTGAGATCACTTATCGTAGAT 2240
```

FIG. 2B

```
 696  S  L  C  Y  Q  L  P  A  C  V  S  P  G  V  T  V  V  I  S  P  L  R  S  L  I  V  D
      CAAGTCCAAAAGCTGACTTCCTTGGATATTCCAGTACATCTGACAGTGATAAGACTGACTCAGAAGCTACAAATAT  2320
 723  Q  V  Q  K  L  T  S  L  D  I  P  A  T  Y  L  T  G  D  K  T  D  S  E  A  T  N  I
      TTACCTCCAGTTATCAAAAAGACCCAATCAATAAACTTCTATATGTCACTGGAGAAAAGATCTGTCAAGTAACAGAC  2400
 750  Y  L  Q  L  S  K  K  D  P  I  K  L  L  Y  V  T  P  E  K  I  C  A  S  N  R
      TCATTTCTACTCTGGAGAATCTCTATGAGGAAGCTCTTGGCACGTTTGTTATGAAGCACATTGTCAGTCAG  2480
 776  L  I  S  T  L  E  N  L  Y  E  R  K  L  L  A  R  F  V  I  D  E  A  H  C  V  S  Q
      TGGGGACATGATTTTCGTCAAGATTACAAAAGAATGCTTCGCCAGAAGTTCCTCTGTTCCGTGATGGCTCT  2560
 803  W  G  H  D  F  R  Q  D  Y  K  R  M  N  M  L  R  Q  K  F  P  S  V  P  V  M  A  L
      TACGGCCACAGCTAATCCCAGTGTACAGAAGGACATCCTGACTCAGCTGAAGATTCTCAGGCCACCTCAGTTGTTAGCATGA  2640
 830  T  A  T  A  N  P  R  V  Q  K  D  I  L  T  Q  L  K  I  L  R  P  Q  V  F  S  M
      GCTTTAACAGACATAATCTGAAATACTATGTATTACCGAAAAAGCCTAAAAAGGTGGCATTGATTGCCTAGAATGCTC  2720
 856  S  F  N  R  H  N  L  K  Y  Y  V  L  P  K  K  V  A  F  D  C  L  E  W  I
      AGAAAGCACCACCATATGATTCAGGGATAATTTACTGCCTCTCCAGCGAGAATGCTGACACGTTACA  2800
 883  R  K  H  H  P  Y  D  S  G  I  I  Y  C  L  S  R  R  E  C  D  T  M  A  D  T  L  Q
      GAGAGATGGGCTGCTGTCTCTTGCTTCAGTGATCTGCCAGAGATGAAGTCAGCAGAAGTGGATTA  2880
 910  R  D  G  L  A  A  L  A  Y  H  A  G  L  S  D  S  A  R  D  E  V  Q  Q  K  W  I
      ATCAGGAGATGGCTGTGTCAGTTGATCTGTCTACAATTGGAATGGGATTGACAAACGGAGTGATTGTGATT  2960
 936  N  Q  D  G  C  Q  V  I  C  A  T  I  A  F  G  M  G  I  D  K  P  D  V  R  F  V  I
      CATGCCATCTCTCCCTAAATCTGTGGAGGGTTACTACCAGAGAATCTGGCAGAGCTGGAAGAGATGGGAAATATCTCACTG  3040
 963  H  A  S  L  P  K  S  V  E  G  Y  Y  Q  E  S  G  R  A  G  R  D  G  E  I  S  H  C
      CCTGCTTTTCTATACCATCATGATGTGACCAGACTGAAAAGACTTATAATGATGGAAAAAGATGAAACCATCATACAA  3120
 990  L  F  Y  T  Y  H  D  V  T  R  L  K  R  L  I  M  E  K  D  G  N  H  H  T
      GAGAAACTCACTTCACTTCAATAATTGTATAGCATGTGAAATCGAATCAGGAGAATACGAATGCAGAATACAGCTTTTG  3200
1016  R  E  T  H  F  N  N  L  Y  S  M  V  H  Y  C  E  N  I  T  E  C  R  R  I  Q  L  L
      GCCTACTTGGTGAAAAATCCTCAATTAATCCTGATTTTGTAAGAACACCCAGATGTTCTTGTGATAATTGCTGTAAAAC  3280
1043  A  Y  F  G  E  N  G  F  N  P  D  F  C  K  K  H  P  D  V  S  C  D  N  C  C  K  T
```

FIG. 2C

```
     AAGGATTATAAACAGAGATGACTGACGATGTGAAAGTATTGTAAGATTTGTCAAGAACATAGTTCATCACAAG 3360
1070  K  D  Y  K  T  R  D  V  T  D  D  V  K  S  I  V  R  F  V  Q  E  H  S  S  S  Q
     GAATGAGAAATATAAAACATGTAGTCCTTCTGAAGATTACTATGAATATGCTGTGACATTTCTTGGGAGTAAG 3440
1096  G  M  R  N  I  K  H  V  G  P  S  G  R  F  T  M  N  L  V  D  I  F  L  G  S  K
     AGTGCAAAAATCCAGTCAGTATATTTGGAAAAGGATCTGCTTATTCACGACACAATGCCGAAAGACTTTTAAAAGCT 3520
1123  S  A  K  I  Q  S  G  I  F  G  K  G  S  A  Y  S  R  H  N  A  E  R  L  F  K  K  L
     GATACTTGACAAGATTTTGATGAAGACTTATATCAATGCCAGGCGATCGCTTATGATGCTCGAAATA 3600
1150  I  L  D  K  I  L  D  E  D  L  Y  I  N  A  N  D  Q  A  I  A  Y  V  M  L  G  N
     AAGCCCAAACTGTACTAAATGGCAATTAAAGGTAGACTTTATGGAAACAGAAAATTCCAGCAGTGTGAAAAACAAAA 3680
1176  K  A  Q  T  V  L  N  G  N  L  K  V  D  F  M  E  T  E  N  S  S  V  K  K  Q  K
     GCGTTAGTAGCAAAAGTGTCTCAGAGGGAAGAGATGGTTAAAAAATGTCTGGAGAACTTACAGAGTCTGCAATCT 3760
1203  A  L  V  A  K  V  S  Q  R  E  E  M  V  K  K  C  L  G  E  L  T  E  V  C  K  S  L
     GGGGAAAGTTTTGTGTCCATTATGGACACTGCCGTCCTCACTCTCAAGAAGCTTGCAGAATCTTTATCTTCTG 3840
1230  G  K  V  F  G  V  H  Y  F  N  I  F  N  T  V  T  L  K  K  L  A  E  S  L  S  S
     ATCCTGAGGTTTTGCTTCAAATTGATGGTGTTACTGAAGACAGTCCTGAAAAATATGGTGCGAAGTGATTCAGTATTA 3920
1256  D  P  E  V  L  L  Q  I  D  G  V  T  E  D  S  P  E  K  Y  G  A  E  V  I  S  V  L
     CAGAAATACTCTGAATGGACATCGCCAGCTGAAGACTGTCCCCAGGATAAGCCTGTCCAGCAGCCCCGGAAG 4000
1283  Q  K  Y  S  E  W  T  S  P  A  E  D  S  S  P  G  I  S  L  S  S  S  R  G  P  G  R
     AAGTGCCGCTGAGGAGCTTGACGAGGAAATACCCGTATCTTCCACTACTTGCAAGTAAAACCAGAAATGAAGGAAGA 4080
1310  S  A  E  E  L  D  E  E  I  P  V  S  S  H  Y  F  A  S  K  T  R  N  E  R  K
     GGAAAAAGATGCCAGCCTCCCAAAGTCTTAAGAGAGAAAAATCTTCCAGTGGTTCCAAGGGGGGTCTGCC 4160
1336  R  K  K  M  P  A  S  Q  R  S  K  R  R  K  T  A  S  G  S  K  A  K  G  G  S  A
     ACATGTAGAAAGATATCTTCCAAAACGAAATCCTCCAGCATCATTGATCCAGTTCAGCTTCACTACTTCTCAAGCGAC 4240
1363  T  C  R  K  I  S  S  K  T  K  S  S  I  I  G  S  S  A  S  H  T  S  Q  A  T
     ATCAGGAGCCAATAGCAAATTGGGGATTATGCTCACCGAAGCTCTATAAATAGACCGTTTCTTAAGCCTTCATATGCAT 4320
1390  S  G  A  N  S  K  L  G  I  M  A  P  P  K  P  I  N  R  P  F  L  K  P  S  Y  A
     TCTCATAAcaaccgaatctcaatgtacatagacccctctttgttgtcagcatctgtgactataaagctg 4400
1416  F  S
     ttattcctgttatacaaaaaaaaaaaaaaaa 4437
```

FIG. 2D

```
                                                     *                                          Ia
649   FPHTKEMMKIFHKKFGLHNFRTNQLEAINAALLGEDCFILMPTGGGKSLCYQLPACV-----SPGVTVVISPLRSLIVDQV    BLM
74    FPWSGKVKDILQNVFKLEKFRPLQLETINVTMAGKEVFLVMPTGGGKSLCYQLPALC-----SDGFTLVICPLISLMEDQL    REQL
659   YPWSDEVLYRLHEVFKLPGFRPNQLEAVNATLQGKDVFVLMPTGGGKSLCYQLPAVVKSGKTHGTTIVISPLISLMQDQV     SGS1
16    ------VLQETFGYQQFRPGQEEIIDTVLSGRDCLVVMPTGGGKSLCYQIPALL-----LNGLTVVSPLISLMKDQV        recQ II
725   QKLTSLDIPATYLTGDKTDSEATNIYLQLSKKDPIIKLLYVTPEKICASNRLISTLENLYERKLLARFVIDEAHCVSQWG     BLM
150   MVLKQLGISATMLNASSSKEHVKWVHDEMVNKNSELKLIYVTPEKIAKSKMFMSRLEKAYEARRFTRIAVDEVHCCSQWQ     REQL
739   EHLLNKNIKASMFSSRGTAEQRRQTFNLFIN--GLLDLVYISPEMISASEQCKRAISRLYADGKLARIVVDEAHCVSNWG     SGS1
83    DQLQANGVAAACLNSTQTREQQLEVMT---GCRTGQIRLLYIAPERL----MLDNFLEHL-AHWNPVLLAVDEAHCISQWG    recQ III                                     *
805   HDFRQDYKRMNMLRQKFPSVPVMALTATANPRVQKDILTQLKILRPQVFSMSFNRHNLKYYVLPKKPKKVA----FDCLEW    BLM
230   HDFRPDYKALGILKRQFPNASLIGLTATATNHVLTDAQKILCIEKCFTFTASFNRPNL-YYEVRQKPSNTEDFIEDIVKL    REQL
817   HDFRPDYKELKFFKREYPDIPMIALTATASEQVRMDIIHNLELKEPVFLKQSFNRTNL-YYEVNKKTKNT---IFEICDA    SGS1
157   HDFRPEYAALGQLRQRFPTLPFMALTATADDTTRQDIVRLLGLNDPLIQISSEDRPNIRY-MLMEKFKPLDQLM----RY    recQ V
882   IRKHHPYDSGIIYCLSRRECDTMADTLQRDGLAALAYHAGLSDSARDEVQQKWINQDGCQVICATIAFGMGIDKPDVRFV    BLM
309   INGRYKGQSGIIYCFSQKDSEQVTVSLQNLGIHAGAYHANLEPEDKTTVHRKWSANE-IQVVATVAFGMGIDKPDVRFV     REQL
893   VKSRFKNQTGIIYCHSKKSCEQTSAQMQRNGIKCAYYHAGMEPDERLSVQKAWQADE-IQVICATVAFGMGIDKPDVRFV    SGS1
233   VQEQ-RGKSGIIYCNSRAKVEDTAAALQSKGISAAAYHAGLENNVRADVQEKFQRDD-LQIVVATVAFGMGINKPNVRFV    recQ VI
962   IHASLPKSVEGYYQESGRAGRDGEISHCLLFYTYHDVTRLKRLIMMEKDGNHHTRETHFNNLYSMVHYCENITECRRIQL    BLM
388   IHHSMSKSMENYYQESGRAGRDDMKADCILYYGFGDIFRISSMVVMENVGQQ------KLYEMVSYCQNISKSRRVLM     REQL
972   YHFTVPRTLEGYYQETGRAGRDGNYSYCITYFSFRDIRTMQTMIQKDKNLDRENKEKHLNKLQQVMAYCDNVTDCRRKLV    SGS1
311   VHFDIPRNIESYYQETGRAGRDGLPAEAMLFYDPADMAWLRRCLEEKPQGQLQDIERH--KLNAMGAFAEAQT-CRRLVL    recQ
```

FIG. 4

SEQUENCE LISTING ( 1 ) GENERAL INFORMATION:

( i i i ) NUMBER OF SEQUENCES: 78

( 2 ) INFORMATION FOR SEQ ID NO:1:

( i ) SEQUENCE CHARACTERISTICS:
        ( A ) LENGTH: 19
        ( B ) TYPE: NUCLEIC ACID
        ( C ) STRANDEDNESS: SINGLE
        ( D ) TOPOLOGY: LINEAR ( i i ) MOLECULE TYPE:
        ( A ) DESCRIPTION: OTHER NUCLEIC ACID ( i i i ) HYPOTHETICAL: YES ( i v ) ANTI-SENSE: NO ( x i ) SEQUENCE DESCRIPTION: SEQ ID NO: 1:

GGTGGCGACG ACTCCTGGA        19

( 2 ) INFORMATION FOR SEQ ID NO:2:

( i ) SEQUENCE CHARACTERISTICS:

(A) LENGTH: 19
                (B) TYPE: NUCLEIC ACID
                (C) STRANDEDNESS: SINGLE
                (D) TOPOLOGY: LINEAR (ii) MOLECULE TYPE:
                (A) DESCRIPTION: OTHER NUCLEIC ACID (iii) HYPOTHETICAL: YES (iv) ANTI-SENSE: NO (ix) FEATURE:
                (A) NAME/KEY:
                (B) LOCATION:
                (C) IDENTIFICATION METHOD:
                (D) OTHER INFORMATION:

(xi) SEQUENCE DESCRIPTION: SEQ ID NO: 2:

ACCAGACCAA CTGGTAATG                                                                                            19

(2) INFORMATION FOR SEQ ID NO:3:

(i) SEQUENCE CHARACTERISTICS:
                (A) LENGTH: 20
                (B) TYPE: NUCLEIC ACID
                (C) STRANDEDNESS: SINGLE
                (D) TOPOLOGY: LINEAR (ii) MOLECULE TYPE:
                (A) DESCRIPTION: OTHER NUCLEIC ACID (iii) HYPOTHETICAL: YES (iv) ANTI-SENSE: NO (ix) FEATURE:
                (A) NAME/KEY:
                (B) LOCATION:
                (C) IDENTIFICATION METHOD:
                (D) OTHER INFORMATION:

(xi) SEQUENCE DESCRIPTION: SEQ ID NO: 3:

ATGGTAGCGA CCGGCGCTCA                                                                                           20

(2) INFORMATION FOR SEQ ID NO:4:

(i) SEQUENCE CHARACTERISTICS:
                (A) LENGTH: 20
                (B) TYPE: NUCLEIC ACID
                (C) STRANDEDNESS: SINGLE
                (D) TOPOLOGY: LINEAR (ii) MOLECULE TYPE:
                (A) DESCRIPTION: OTHER NUCLEIC ACID (iii) HYPOTHETICAL: YES (iv) ANTI-SENSE: NO (ix) FEATURE:
                (A) NAME/KEY:
                (B) LOCATION:
                (C) IDENTIFICATION METHOD:
                (D) OTHER INFORMATION:

(xi) SEQUENCE DESCRIPTION: SEQ ID NO: 4:

CCGTCAGTAT CGGCGGAATT                                                                                           20

(2) INFORMATION FOR SEQ ID NO:5:

(i) SEQUENCE CHARACTERISTICS:
                (A) LENGTH: 21
                (B) TYPE: NUCLEIC ACID (C) STRANDEDNESS: SINGLE
                (D) TOPOLOGY: LINEAR (ii) MOLECULE TYPE:
                (A) DESCRIPTION: OTHER NUCLEIC ACID (iii) HYPOTHETICAL: YES (iv) ANTI-SENSE: NO (ix) FEATURE:
                (A) NAME/KEY:
                (B) LOCATION:
                (C) IDENTIFICATION METHOD:
                (D) OTHER INFORMATION:

(xi) SEQUENCE DESCRIPTION: SEQ ID NO: 5:

TTGTGGTGTT GGGTAGAGGT T 21

(2) INFORMATION FOR SEQ ID NO:6:

(i) SEQUENCE CHARACTERISTICS:
                (A) LENGTH: 15
                (B) TYPE: NUCLEIC ACID
                (C) STRANDEDNESS: SINGLE
                (D) TOPOLOGY: LINEAR (ii) MOLECULE TYPE:
                (A) DESCRIPTION: OTHER NUCLEIC ACID (iii) HYPOTHETICAL: YES (iv) ANTI-SENSE: NO (ix) FEATURE:
                (A) NAME/KEY:
                (B) LOCATION:
                (C) IDENTIFICATION METHOD:
                (D) OTHER INFORMATION:

(xi) SEQUENCE DESCRIPTION: SEQ ID NO: 6:

GCCGCCGGCA CCAAC 15

(2) INFORMATION FOR SEQ ID NO:7:

(i) SEQUENCE CHARACTERISTICS:
                (A) LENGTH: 22
                (B) TYPE: NUCLEIC ACID
                (C) STRANDEDNESS: SINGLE
                (D) TOPOLOGY: LINEAR (ii) MOLECULE TYPE:
                (A) DESCRIPTION: OTHER NUCLEIC ACID (iii) HYPOTHETICAL: YES (iv) ANTI-SENSE: NO (ix) FEATURE:
                (A) NAME/KEY:
                (B) LOCATION:
                (C) IDENTIFICATION METHOD:
                (D) OTHER INFORMATION:

(xi) SEQUENCE DESCRIPTION: SEQ ID NO: 7:

CCTCAGTCAA ATCTATNGC TC 22

(2) INFORMATION FOR SEQ ID NO:8:

(i) SEQUENCE CHARACTERISTICS:
                (A) LENGTH: 23
                (B) TYPE: NUCLEIC ACID
                (C) STRANDEDNESS: SINGLE
                (D) TOPOLOGY: LINEAR (i i) MOLECULE TYPE:
  (A) DESCRIPTION: OTHER NUCLEIC ACID (i i i) HYPOTHETICAL: YES (i v) ANTI-SENSE: NO (i x) FEATURE:
  (A) NAME/KEY:
  (B) LOCATION:
  (C) IDENTIFICATION METHOD:
  (D) OTHER INFORMATION:

(x i) SEQUENCE DESCRIPTION: SEQ ID NO: 8:

GCCATCACCG GAACAGAAGG AAA                             23

(2) INFORMATION FOR SEQ ID NO:9:

(i) SEQUENCE CHARACTERISTICS:
    (A) LENGTH: 22
    (B) TYPE: NUCLEIC ACID
    (C) STRANDEDNESS: SINGLE
    (D) TOPOLOGY: LINEAR (i i) MOLECULE TYPE:
    (A) DESCRIPTION: OTHER NUCLEIC ACID (i i i) HYPOTHETICAL: YES (i v) ANTI-SENSE: NO (i x) FEATURE:
    (A) NAME/KEY:
    (B) LOCATION:
    (C) IDENTIFICATION METHOD:
    (D) OTHER INFORMATION:

(x i) SEQUENCE DESCRIPTION: SEQ ID NO: 9:

TCTTCTGGAG GAGGTGGAAC AA                              22

(2) INFORMATION FOR SEQ ID NO:10:

(i) SEQUENCE CHARACTERISTICS:
    (A) LENGTH: 19
    (B) TYPE: NUCLEIC ACID
    (C) STRANDEDNESS: SINGLE
    (D) TOPOLOGY: LINEAR (i i) MOLECULE TYPE:
    (A) DESCRIPTION: OTHER NUCLEIC ACID (i i i) HYPOTHETICAL: YES (i v) ANTI-SENSE: NO (i x) FEATURE:
    (A) NAME/KEY:
    (B) LOCATION:
    (C) IDENTIFICATION METHOD:
    (D) OTHER INFORMATION:

(x i) SEQUENCE DESCRIPTION: SEQ ID NO: 10:

GGATCCTGGT TCCGTCCGC                                  19

(2) INFORMATION FOR SEQ ID NO:11:

(i) SEQUENCE CHARACTERISTICS:
    (A) LENGTH: 21
    (B) TYPE: NUCLEIC ACID
    (C) STRANDEDNESS: SINGLE
    (D) TOPOLOGY: LINEAR (i i) MOLECULE TYPE:

(A) DESCRIPTION: OTHER NUCLEIC ACID (iii) HYPOTHETICAL: YES (iv) ANTI-SENSE: NO (ix) FEATURE:
    (A) NAME/KEY:
    (B) LOCATION:
    (C) IDENTIFICATION METHOD:
    (D) OTHER INFORMATION:

(xi) SEQUENCE DESCRIPTION: SEQ ID NO: 11:

CAACTAGAAC GTCACTCAGC C                   21

(2) INFORMATION FOR SEQ ID NO:12:

(i) SEQUENCE CHARACTERISTICS:
    (A) LENGTH: 22
    (B) TYPE: NUCLEIC ACID
    (C) STRANDEDNESS: SINGLE
    (D) TOPOLOGY: LINEAR (ii) MOLECULE TYPE:
    (A) DESCRIPTION: OTHER NUCLEIC ACID (iii) HYPOTHETICAL: YES (iv) ANTI-SENSE: NO (ix) FEATURE:
    (A) NAME/KEY:
    (B) LOCATION:
    (C) IDENTIFICATION METHOD:
    (D) OTHER INFORMATION:

(xi) SEQUENCE DESCRIPTION: SEQ ID NO: 12:

GACTTTTCCT TCAGTGAACC TC                   22

(2) INFORMATION FOR SEQ ID NO:13:

(i) SEQUENCE CHARACTERISTICS:
    (A) LENGTH: 21
    (B) TYPE: NUCLEIC ACID
    (C) STRANDEDNESS: SINGLE
    (D) TOPOLOGY: LINEAR (ii) MOLECULE TYPE:
    (A) DESCRIPTION: OTHER NUCLEIC ACID (iii) HYPOTHETICAL: YES (iv) ANTI-SENSE: NO (ix) FEATURE:
    (A) NAME/KEY:
    (B) LOCATION:
    (C) IDENTIFICATION METHOD:
    (D) OTHER INFORMATION:

(xi) SEQUENCE DESCRIPTION: SEQ ID NO: 13:

CCAGATTTCT TGCAGACTCC G                   21

(2) INFORMATION FOR SEQ ID NO:14:

(i) SEQUENCE CHARACTERISTICS:
    (A) LENGTH: 24
    (B) TYPE: NUCLEIC ACID
    (C) STRANDEDNESS: SINGLE
    (D) TOPOLOGY: LINEAR (ii) MOLECULE TYPE:
    (A) DESCRIPTION: OTHER NUCLEIC ACID (iii) HYPOTHETICAL: YES (iv) ANTI-SENSE: NO (ix) FEATURE:
  (A) NAME/KEY:
  (B) LOCATION:
  (C) IDENTIFICATION METHOD:
  (D) OTHER INFORMATION:

(xi) SEQUENCE DESCRIPTION: SEQ ID NO: 14:

CTTTAAGTAC CATCAATGAT TGGG 24

(2) INFORMATION FOR SEQ ID NO:15:

(i) SEQUENCE CHARACTERISTICS:
    (A) LENGTH: 22
    (B) TYPE: NUCLEIC ACID
    (C) STRANDEDNESS: SINGLE
    (D) TOPOLOGY: LINEAR (ii) MOLECULE TYPE:
    (A) DESCRIPTION: OTHER NUCLEIC ACID (iii) HYPOTHETICAL: YES (iv) ANTI-SENSE: NO (ix) FEATURE:
    (A) NAME/KEY:
    (B) LOCATION:
    (C) IDENTIFICATION METHOD:
    (D) OTHER INFORMATION:

(xi) SEQUENCE DESCRIPTION: SEQ ID NO: 15:

GAGTAAGCAC TGCTCAGAAA TC 22

(2) INFORMATION FOR SEQ ID NO:16:

(i) SEQUENCE CHARACTERISTICS:
    (A) LENGTH: 23
    (B) TYPE: NUCLEIC ACID
    (C) STRANDEDNESS: SINGLE
    (D) TOPOLOGY: LINEAR (ii) MOLECULE TYPE:
    (A) DESCRIPTION: OTHER NUCLEIC ACID (iii) HYPOTHETICAL: YES (iv) ANTI-SENSE: NO (ix) FEATURE:
    (A) NAME/KEY:
    (B) LOCATION:
    (C) IDENTIFICATION METHOD:
    (D) OTHER INFORMATION:

(xi) SEQUENCE DESCRIPTION: SEQ ID NO: 16:

CGAGCAAATA GATTTGACTG AGG 23

(2) INFORMATION FOR SEQ ID NO:17:

(i) SEQUENCE CHARACTERISTICS:
    (A) LENGTH: 21
    (B) TYPE: NUCLEIC ACID
    (C) STRANDEDNESS: SINGLE
    (D) TOPOLOGY: LINEAR (ii) MOLECULE TYPE:
    (A) DESCRIPTION: OTHER NUCLEIC ACID (iii) HYPOTHETICAL: YES ( i v ) ANTI-SENSE: NO ( i x ) FEATURE:
                ( A ) NAME/KEY:
                ( B ) LOCATION:
                ( C ) IDENTIFICATION METHOD:
                ( D ) OTHER INFORMATION:

( x i ) SEQUENCE DESCRIPTION: SEQ ID NO: 17:

GAAGATGCTC AGGAAAGTGA C                                                                                            21

( 2 ) INFORMATION FOR SEQ ID NO:18:

( i ) SEQUENCE CHARACTERISTICS:
                ( A ) LENGTH: 24
                ( B ) TYPE: NUCLEIC ACID
                ( C ) STRANDEDNESS: SINGLE
                ( D ) TOPOLOGY: LINEAR ( i i ) MOLECULE TYPE:
                ( A ) DESCRIPTION: OTHER NUCLEIC ACID ( i i i ) HYPOTHETICAL: YES ( i v ) ANTI-SENSE: NO ( i x ) FEATURE:
                ( A ) NAME/KEY:
                ( B ) LOCATION:
                ( C ) IDENTIFICATION METHOD:
                ( D ) OTHER INFORMATION:

( x i ) SEQUENCE DESCRIPTION: SEQ ID NO: 18:

CAACTGAGAA AGTTCCATGT ATTG                                                                                         24

( 2 ) INFORMATION FOR SEQ ID NO:19:

( i ) SEQUENCE CHARACTERISTICS:
                ( A ) LENGTH: 24
                ( B ) TYPE: NUCLEIC ACID
                ( C ) STRANDEDNESS: SINGLE
                ( D ) TOPOLOGY: LINEAR ( i i ) MOLECULE TYPE:
                ( A ) DESCRIPTION: OTHER NUCLEIC ACID ( i i i ) HYPOTHETICAL: YES ( i v ) ANTI-SENSE: NO ( i x ) FEATURE:
                ( A ) NAME/KEY:
                ( B ) LOCATION:
                ( C ) IDENTIFICATION METHOD:
                ( D ) OTHER INFORMATION:

( x i ) SEQUENCE DESCRIPTION: SEQ ID NO: 19:

CTATTCCTGA TGATAAACTG AAAC                                                                                         24

( 2 ) INFORMATION FOR SEQ ID NO:20:

( i ) SEQUENCE CHARACTERISTICS:
                ( A ) LENGTH: 21
                ( B ) TYPE: NUCLEIC ACID
                ( C ) STRANDEDNESS: SINGLE
                ( D ) TOPOLOGY: LINEAR ( i i ) MOLECULE TYPE:
                ( A ) DESCRIPTION: OTHER NUCLEIC ACID ( i i i ) HYPOTHETICAL: YES ( i v ) ANTI-SENSE: NO ( i x ) FEATURE:
  ( A ) NAME/KEY:
  ( B ) LOCATION:
  ( C ) IDENTIFICATION METHOD:
  ( D ) OTHER INFORMATION:

( x i ) SEQUENCE DESCRIPTION: SEQ ID NO: 20:

GTGGAGATAC AGGCCTGATT C                    21

( 2 ) INFORMATION FOR SEQ ID NO:21:

( i ) SEQUENCE CHARACTERISTICS:
    ( A ) LENGTH: 20
    ( B ) TYPE: NUCLEIC ACID
    ( C ) STRANDEDNESS: SINGLE
    ( D ) TOPOLOGY: LINEAR ( i i ) MOLECULE TYPE:
    ( A ) DESCRIPTION: OTHER NUCLEIC ACID ( i i i ) HYPOTHETICAL: YES ( i v ) ANTI-SENSE: NO ( i x ) FEATURE:
    ( A ) NAME/KEY:
    ( B ) LOCATION:
    ( C ) IDENTIFICATION METHOD:
    ( D ) OTHER INFORMATION:

( x i ) SEQUENCE DESCRIPTION: SEQ ID NO: 21:

CAGGATTCTC TGCCACCAGG                       20

( 2 ) INFORMATION FOR SEQ ID NO:22:

( i ) SEQUENCE CHARACTERISTICS:
    ( A ) LENGTH: 22
    ( B ) TYPE: NUCLEIC ACID
    ( C ) STRANDEDNESS: SINGLE
    ( D ) TOPOLOGY: LINEAR ( i i ) MOLECULE TYPE:
    ( A ) DESCRIPTION: OTHER NUCLEIC ACID ( i i i ) HYPOTHETICAL: YES ( i v ) ANTI-SENSE: NO ( i x ) FEATURE:
    ( A ) NAME/KEY:
    ( B ) LOCATION:
    ( C ) IDENTIFICATION METHOD:
    ( D ) OTHER INFORMATION:

( x i ) SEQUENCE DESCRIPTION: SEQ ID NO: 22:

CAGGAAATGT TCTCACAAGC AC                    22

( 2 ) INFORMATION FOR SEQ ID NO:23:

( i ) SEQUENCE CHARACTERISTICS:
    ( A ) LENGTH: 21
    ( B ) TYPE: NUCLEIC ACID
    ( C ) STRANDEDNESS: SINGLE
    ( D ) TOPOLOGY: LINEAR ( i i ) MOLECULE TYPE:
    ( A ) DESCRIPTION: OTHER NUCLEIC ACID ( i i i ) HYPOTHETICAL: YES ( i v ) ANTI-SENSE: NO ( i x ) FEATURE:
    ( A ) NAME/KEY:

( B ) LOCATION:
                    ( C ) IDENTIFICATION METHOD:
                    ( D ) OTHER INFORMATION:

( x i ) SEQUENCE DESCRIPTION: SEQ ID NO: 23:

CAGCCAGCAA ATCTTCCACA G                                                                                          21

( 2 ) INFORMATION FOR SEQ ID NO:24:

( i ) SEQUENCE CHARACTERISTICS:
                    ( A ) LENGTH: 23
                    ( B ) TYPE: NUCLEIC ACID
                    ( C ) STRANDEDNESS: SINGLE
                    ( D ) TOPOLOGY: LINEAR ( i i ) MOLECULE TYPE:
                    ( A ) DESCRIPTION: OTHER NUCLEIC ACID ( i i i ) HYPOTHETICAL: YES ( i v ) ANTI-SENSE: NO ( i x ) FEATURE:
                    ( A ) NAME/KEY:
                    ( B ) LOCATION:
                    ( C ) IDENTIFICATION METHOD:
                    ( D ) OTHER INFORMATION:

( x i ) SEQUENCE DESCRIPTION: SEQ ID NO: 24:

GAATTATACT GACAAGTCAG CAC                                                                                        23

( 2 ) INFORMATION FOR SEQ ID NO:25:

( i ) SEQUENCE CHARACTERISTICS:
                    ( A ) LENGTH: 20
                    ( B ) TYPE: NUCLEIC ACID
                    ( C ) STRANDEDNESS: SINGLE
                    ( D ) TOPOLOGY: LINEAR ( i i ) MOLECULE TYPE:
                    ( A ) DESCRIPTION: OTHER NUCLEIC ACID ( i i i ) HYPOTHETICAL: YES ( i v ) ANTI-SENSE: NO ( i x ) FEATURE:
                    ( A ) NAME/KEY:
                    ( B ) LOCATION:
                    ( C ) IDENTIFICATION METHOD:
                    ( D ) OTHER INFORMATION:

( x i ) SEQUENCE DESCRIPTION: SEQ ID NO: 25:

CTCCTGGGGT CACTGTTGTC                                                                                            20

( 2 ) INFORMATION FOR SEQ ID NO:26:

( i ) SEQUENCE CHARACTERISTICS:
                    ( A ) LENGTH: 22
                    ( B ) TYPE: NUCLEIC ACID
                    ( C ) STRANDEDNESS: SINGLE
                    ( D ) TOPOLOGY: LINEAR ( i i ) MOLECULE TYPE:
                    ( A ) DESCRIPTION: OTHER NUCLEIC ACID ( i i i ) HYPOTHETICAL: YES ( i v ) ANTI-SENSE: NO ( i x ) FEATURE:
                    ( A ) NAME/KEY:
                    ( B ) LOCATION:
                    ( C ) IDENTIFICATION METHOD:

-continued ( D ) OTHER INFORMATION:

( x i ) SEQUENCE DESCRIPTION: SEQ ID NO: 26:

GAGGTTCACT GAAGGAAAAG TC                                                                                    2 2

( 2 ) INFORMATION FOR SEQ ID NO:27:

( i ) SEQUENCE CHARACTERISTICS:
                ( A ) LENGTH: 21
                ( B ) TYPE: NUCLEIC ACID
                ( C ) STRANDEDNESS: SINGLE
                ( D ) TOPOLOGY: LINEAR ( i i ) MOLECULE TYPE:
                ( A ) DESCRIPTION: OTHER NUCLEIC ACID ( i i i ) HYPOTHETICAL: YES ( i v ) ANTI-SENSE: NO ( i x ) FEATURE:
                ( A ) NAME/KEY:
                ( B ) LOCATION:
                ( C ) IDENTIFICATION METHOD:
                ( D ) OTHER INFORMATION:

( x i ) SEQUENCE DESCRIPTION: SEQ ID NO: 27:

GAAGTCCTTG ACCCTTTGCT G                                                                                     2 1

( 2 ) INFORMATION FOR SEQ ID NO:28:

( i ) SEQUENCE CHARACTERISTICS:
                ( A ) LENGTH: 23
                ( B ) TYPE: NUCLEIC ACID
                ( C ) STRANDEDNESS: SINGLE
                ( D ) TOPOLOGY: LINEAR ( i i ) MOLECULE TYPE:
                ( A ) DESCRIPTION: OTHER NUCLEIC ACID ( i i i ) HYPOTHETICAL: YES ( i v ) ANTI-SENSE: NO ( i x ) FEATURE:
                ( A ) NAME/KEY:
                ( B ) LOCATION:
                ( C ) IDENTIFICATION METHOD:
                ( D ) OTHER INFORMATION:

( x i ) SEQUENCE DESCRIPTION: SEQ ID NO: 28:

GGGATTTCTT TACAGTTGGT GTG                                                                                   2 3

( 2 ) INFORMATION FOR SEQ ID NO:29:

( i ) SEQUENCE CHARACTERISTICS:
                ( A ) LENGTH: 22
                ( B ) TYPE: NUCLEIC ACID
                ( C ) STRANDEDNESS: SINGLE
                ( D ) TOPOLOGY: LINEAR ( i i ) MOLECULE TYPE:
                ( A ) DESCRIPTION: OTHER NUCLEIC ACID ( i i i ) HYPOTHETICAL: YES ( i v ) ANTI-SENSE: NO ( i x ) FEATURE:
                ( A ) NAME/KEY:
                ( B ) LOCATION:
                ( C ) IDENTIFICATION METHOD:
                ( D ) OTHER INFORMATION:

(x i) SEQUENCE DESCRIPTION: SEQ ID NO: 29:

CTCTTACAAA GTGACTTTGG GG 22

(2) INFORMATION FOR SEQ ID NO:30:

(i) SEQUENCE CHARACTERISTICS:
        (A) LENGTH: 23
        (B) TYPE: NUCLEIC ACID
        (C) STRANDEDNESS: SINGLE
        (D) TOPOLOGY: LINEAR (i i) MOLECULE TYPE:
        (A) DESCRIPTION: OTHER NUCLEIC ACID (i i i) HYPOTHETICAL: YES (i v) ANTI-SENSE: NO (i x) FEATURE:
        (A) NAME/KEY:
        (B) LOCATION:
        (C) IDENTIFICATION METHOD:
        (D) OTHER INFORMATION:

(x i) SEQUENCE DESCRIPTION: SEQ ID NO: 30:

CCTCAGTCAA ATCTATTTGC TCG 23

(2) INFORMATION FOR SEQ ID NO:31:

(i) SEQUENCE CHARACTERISTICS:
        (A) LENGTH: 22
        (B) TYPE: NUCLEIC ACID
        (C) STRANDEDNESS: SINGLE
        (D) TOPOLOGY: LINEAR (i i) MOLECULE TYPE:
        (A) DESCRIPTION: OTHER NUCLEIC ACID (i i i) HYPOTHETICAL: YES (i v) ANTI-SENSE: NO (i x) FEATURE:
        (A) NAME/KEY:
        (B) LOCATION:
        (C) IDENTIFICATION METHOD:
        (D) OTHER INFORMATION:

(x i) SEQUENCE DESCRIPTION: SEQ ID NO: 31:

GCTTAACCAT TCTGAGTCAT CC 22

(2) INFORMATION FOR SEQ ID NO:32:

(i) SEQUENCE CHARACTERISTICS:
        (A) LENGTH: 24
        (B) TYPE: NUCLEIC ACID
        (C) STRANDEDNESS: SINGLE
        (D) TOPOLOGY: LINEAR (i i) MOLECULE TYPE:
        (A) DESCRIPTION: OTHER NUCLEIC ACID (i i i) HYPOTHETICAL: YES (i v) ANTI-SENSE: NO (i x) FEATURE:
        (A) NAME/KEY:
        (B) LOCATION:
        (C) IDENTIFICATION METHOD:
        (D) OTHER INFORMATION:

(x i) SEQUENCE DESCRIPTION: SEQ ID NO: 32:

CAATACATGG AACTTTCTCA GTTG 24

( 2 ) INFORMATION FOR SEQ ID NO:33:

( i ) SEQUENCE CHARACTERISTICS:
        ( A ) LENGTH: 23
        ( B ) TYPE: NUCLEIC ACID
        ( C ) STRANDEDNESS: SINGLE
        ( D ) TOPOLOGY: LINEAR ( i i ) MOLECULE TYPE:
        ( A ) DESCRIPTION: OTHER NUCLEIC ACID ( i i i ) HYPOTHETICAL: YES ( i v ) ANTI-SENSE: NO ( i x ) FEATURE:
        ( A ) NAME/KEY:
        ( B ) LOCATION:
        ( C ) IDENTIFICATION METHOD:
        ( D ) OTHER INFORMATION:

( x i ) SEQUENCE DESCRIPTION: SEQ ID NO: 33:

CGTACTAAGG CATTTTGAAG AGG 23

( 2 ) INFORMATION FOR SEQ ID NO:34:

( i ) SEQUENCE CHARACTERISTICS:
        ( A ) LENGTH: 21
        ( B ) TYPE: NUCLEIC ACID
        ( C ) STRANDEDNESS: SINGLE
        ( D ) TOPOLOGY: LINEAR ( i i ) MOLECULE TYPE:
        ( A ) DESCRIPTION: OTHER NUCLEIC ACID ( i i i ) HYPOTHETICAL: YES ( i v ) ANTI-SENSE: NO ( i x ) FEATURE:
        ( A ) NAME/KEY:
        ( B ) LOCATION:
        ( C ) IDENTIFICATION METHOD:
        ( D ) OTHER INFORMATION:

( x i ) SEQUENCE DESCRIPTION: SEQ ID NO: 34:

CACAGTCTGT GCTGGTTTCT G 21

( 2 ) INFORMATION FOR SEQ ID NO:35:

( i ) SEQUENCE CHARACTERISTICS:
        ( A ) LENGTH: 22
        ( B ) TYPE: NUCLEIC ACID
        ( C ) STRANDEDNESS: SINGLE
        ( D ) TOPOLOGY: LINEAR ( i i ) MOLECULE TYPE:
        ( A ) DESCRIPTION: OTHER NUCLEIC ACID ( i i i ) HYPOTHETICAL: YES ( i v ) ANTI-SENSE: NO ( i x ) FEATURE:
        ( A ) NAME/KEY:
        ( B ) LOCATION:
        ( C ) IDENTIFICATION METHOD:
        ( D ) OTHER INFORMATION:

( x i ) SEQUENCE DESCRIPTION: SEQ ID NO: 35:

CCTTCATAGA ATTCCCTGTA GG 22

( 2 ) INFORMATION FOR SEQ ID NO:36:

( i ) SEQUENCE CHARACTERISTICS:
        ( A ) LENGTH: 21
        ( B ) TYPE: NUCLEIC ACID
        ( C ) STRANDEDNESS: SINGLE
        ( D ) TOPOLOGY: LINEAR ( i i ) MOLECULE TYPE:
        ( A ) DESCRIPTION: OTHER NUCLEIC ACID ( i i i ) HYPOTHETICAL: YES ( i v ) ANTI-SENSE: NO ( i x ) FEATURE:
        ( A ) NAME/KEY:
        ( B ) LOCATION:
        ( C ) IDENTIFICATION METHOD:
        ( D ) OTHER INFORMATION:

( x i ) SEQUENCE DESCRIPTION: SEQ ID NO: 36:

GTGTTTCAGC CCAGTTGCTA C         21

( 2 ) INFORMATION FOR SEQ ID NO:37:

( i ) SEQUENCE CHARACTERISTICS:
        ( A ) LENGTH: 24
        ( B ) TYPE: NUCLEIC ACID
        ( C ) STRANDEDNESS: SINGLE
        ( D ) TOPOLOGY: LINEAR ( i i ) MOLECULE TYPE:
        ( A ) DESCRIPTION: OTHER NUCLEIC ACID ( i i i ) HYPOTHETICAL: YES ( i v ) ANTI-SENSE: NO ( i x ) FEATURE:
        ( A ) NAME/KEY:
        ( B ) LOCATION:
        ( C ) IDENTIFICATION METHOD:
        ( D ) OTHER INFORMATION:

( x i ) SEQUENCE DESCRIPTION: SEQ ID NO: 37:

GCAGTATGTT TATTCTGATC TTTC         24

( 2 ) INFORMATION FOR SEQ ID NO:38:

( i ) SEQUENCE CHARACTERISTICS:
        ( A ) LENGTH: 21
        ( B ) TYPE: NUCLEIC ACID
        ( C ) STRANDEDNESS: SINGLE
        ( D ) TOPOLOGY: LINEAR ( i i ) MOLECULE TYPE:
        ( A ) DESCRIPTION: OTHER NUCLEIC ACID ( i i i ) HYPOTHETICAL: YES ( i v ) ANTI-SENSE: NO ( i x ) FEATURE:
        ( A ) NAME/KEY:
        ( B ) LOCATION:
        ( C ) IDENTIFICATION METHOD:
        ( D ) OTHER INFORMATION:

( x i ) SEQUENCE DESCRIPTION: SEQ ID NO: 38:

CCTTGATGGG TTGATAGGCA G         21

( 2 ) INFORMATION FOR SEQ ID NO:39:

(i) SEQUENCE CHARACTERISTICS:
    (A) LENGTH: 22
    (B) TYPE: NUCLEIC ACID
    (C) STRANDEDNESS: SINGLE
    (D) TOPOLOGY: LINEAR (ii) MOLECULE TYPE:
    (A) DESCRIPTION: OTHER NUCLEIC ACID (iii) HYPOTHETICAL: YES (iv) ANTI-SENSE: NO (ix) FEATURE:
    (A) NAME/KEY:
    (B) LOCATION:
    (C) IDENTIFICATION METHOD:
    (D) OTHER INFORMATION:

(xi) SEQUENCE DESCRIPTION: SEQ ID NO: 39:

CGCTCATGTT TCAGATTTCT GG　　　　　　　　　　　　　　　　　　　　　　22

(2) INFORMATION FOR SEQ ID NO:40:

(i) SEQUENCE CHARACTERISTICS:
    (A) LENGTH: 23
    (B) TYPE: NUCLEIC ACID
    (C) STRANDEDNESS: SINGLE
    (D) TOPOLOGY: LINEAR (ii) MOLECULE TYPE:
    (A) DESCRIPTION: OTHER NUCLEIC ACID (iii) HYPOTHETICAL: YES (iv) ANTI-SENSE: NO (ix) FEATURE:
    (A) NAME/KEY:
    (B) LOCATION:
    (C) IDENTIFICATION METHOD:
    (D) OTHER INFORMATION:

(xi) SEQUENCE DESCRIPTION: SEQ ID NO: 40:

GATCTACGAT AAGTGATCTC AAG　　　　　　　　　　　　　　　　　　　　　23

(2) INFORMATION FOR SEQ ID NO:41:

(i) SEQUENCE CHARACTERISTICS:
    (A) LENGTH: 22
    (B) TYPE: NUCLEIC ACID
    (C) STRANDEDNESS: SINGLE
    (D) TOPOLOGY: LINEAR (ii) MOLECULE TYPE:
    (A) DESCRIPTION: OTHER NUCLEIC ACID (iii) HYPOTHETICAL: YES (iv) ANTI-SENSE: NO (ix) FEATURE:
    (A) NAME/KEY:
    (B) LOCATION:
    (C) IDENTIFICATION METHOD:
    (D) OTHER INFORMATION:

(xi) SEQUENCE DESCRIPTION: SEQ ID NO: 41:

GAGTCTGTTA CTTGCACAGA TC　　　　　　　　　　　　　　　　　　　　　　22

(2) INFORMATION FOR SEQ ID NO:42:

(i) SEQUENCE CHARACTERISTICS:

( A ) LENGTH: 25
                    ( B ) TYPE: NUCLEIC ACID
                    ( C ) STRANDEDNESS: SINGLE
                    ( D ) TOPOLOGY: LINEAR ( i i ) MOLECULE TYPE:
                    ( A ) DESCRIPTION: OTHER NUCLEIC ACID ( i i i ) HYPOTHETICAL: YES ( i v ) ANTI-SENSE: NO ( i x ) FEATURE:
                    ( A ) NAME/KEY:
                    ( B ) LOCATION:
                    ( C ) IDENTIFICATION METHOD:
                    ( D ) OTHER INFORMATION:

( x i ) SEQUENCE DESCRIPTION: SEQ ID NO: 42:

CAATCATAAA ACTTCTATAT GTCAC                                                                                          2 5

( 2 ) INFORMATION FOR SEQ ID NO:43:

( i ) SEQUENCE CHARACTERISTICS:
                    ( A ) LENGTH: 23
                    ( B ) TYPE: NUCLEIC ACID
                    ( C ) STRANDEDNESS: SINGLE
                    ( D ) TOPOLOGY: LINEAR ( i i ) MOLECULE TYPE:
                    ( A ) DESCRIPTION: OTHER NUCLEIC ACID ( i i i ) HYPOTHETICAL: YES ( i v ) ANTI-SENSE: NO ( i x ) FEATURE:
                    ( A ) NAME/KEY:
                    ( B ) LOCATION:
                    ( C ) IDENTIFICATION METHOD:
                    ( D ) OTHER INFORMATION:

( x i ) SEQUENCE DESCRIPTION: SEQ ID NO: 43:

GTGGGGACAT GATTTTCGTC AAG                                                                                            2 3

( 2 ) INFORMATION FOR SEQ ID NO:44:

( i ) SEQUENCE CHARACTERISTICS:
                    ( A ) LENGTH: 21
                    ( B ) TYPE: NUCLEIC ACID
                    ( C ) STRANDEDNESS: SINGLE
                    ( D ) TOPOLOGY: LINEAR ( i i ) MOLECULE TYPE:
                    ( A ) DESCRIPTION: OTHER NUCLEIC ACID ( i i i ) HYPOTHETICAL: YES ( i v ) ANTI-SENSE: NO ( i x ) FEATURE:
                    ( A ) NAME/KEY:
                    ( B ) LOCATION:
                    ( C ) IDENTIFICATION METHOD:
                    ( D ) OTHER INFORMATION:

( x i ) SEQUENCE DESCRIPTION: SEQ ID NO: 44:

GACATCCTGA CTCAGCTGAA G                                                                                              2 1

( 2 ) INFORMATION FOR SEQ ID NO:45:

( i ) SEQUENCE CHARACTERISTICS:
                    ( A ) LENGTH: 21
                    ( B ) TYPE: NUCLEIC ACID ( C ) STRANDEDNESS: SINGLE
            ( D ) TOPOLOGY: LINEAR ( i i ) MOLECULE TYPE:
            ( A ) DESCRIPTION: OTHER NUCLEIC ACID ( i i i ) HYPOTHETICAL: YES ( i v ) ANTI-SENSE: NO ( i x ) FEATURE:
            ( A ) NAME/KEY:
            ( B ) LOCATION:
            ( C ) IDENTIFICATION METHOD:
            ( D ) OTHER INFORMATION:

( x i ) SEQUENCE DESCRIPTION: SEQ ID NO: 45:

GCACCACCCA TATGATTCAG G                                                        2 1

( 2 ) INFORMATION FOR SEQ ID NO:46:

( i ) SEQUENCE CHARACTERISTICS:
            ( A ) LENGTH: 21
            ( B ) TYPE: NUCLEIC ACID
            ( C ) STRANDEDNESS: SINGLE
            ( D ) TOPOLOGY: LINEAR ( i i ) MOLECULE TYPE:
            ( A ) DESCRIPTION: OTHER NUCLEIC ACID ( i i i ) HYPOTHETICAL: YES ( i v ) ANTI-SENSE: NO ( i x ) FEATURE:
            ( A ) NAME/KEY:
            ( B ) LOCATION:
            ( C ) IDENTIFICATION METHOD:
            ( D ) OTHER INFORMATION:

( x i ) SEQUENCE DESCRIPTION: SEQ ID NO: 46:

GATGAAGTGC AGCAGAAGTG G                                                        2 1

( 2 ) INFORMATION FOR SEQ ID NO:47:

( i ) SEQUENCE CHARACTERISTICS:
            ( A ) LENGTH: 20
            ( B ) TYPE: NUCLEIC ACID
            ( C ) STRANDEDNESS: SINGLE
            ( D ) TOPOLOGY: LINEAR ( i i ) MOLECULE TYPE:
            ( A ) DESCRIPTION: OTHER NUCLEIC ACID ( i i i ) HYPOTHETICAL: YES ( i v ) ANTI-SENSE: NO ( i x ) FEATURE:
            ( A ) NAME/KEY:
            ( B ) LOCATION:
            ( C ) IDENTIFICATION METHOD:
            ( D ) OTHER INFORMATION:

( x i ) SEQUENCE DESCRIPTION: SEQ ID NO: 47:

GCAGAGCTGG AAGAGATGGG                                                          2 0

( 2 ) INFORMATION FOR SEQ ID NO:48:

( i ) SEQUENCE CHARACTERISTICS:
            ( A ) LENGTH: 23
            ( B ) TYPE: NUCLEIC ACID
            ( C ) STRANDEDNESS: SINGLE
            ( D ) TOPOLOGY: LINEAR (i i) MOLECULE TYPE:
    (A) DESCRIPTION: OTHER NUCLEIC ACID (i i i) HYPOTHETICAL: YES (i v) ANTI-SENSE: NO (i x) FEATURE:
    (A) NAME/KEY:
    (B) LOCATION:
    (C) IDENTIFICATION METHOD:
    (D) OTHER INFORMATION:

(x i) SEQUENCE DESCRIPTION: SEQ ID NO: 48:

GTATAGCATG GTACATTACT GTG 23

(2) INFORMATION FOR SEQ ID NO:49:

(i) SEQUENCE CHARACTERISTICS:
    (A) LENGTH: 23
    (B) TYPE: NUCLEIC ACID
    (C) STRANDEDNESS: SINGLE
    (D) TOPOLOGY: LINEAR (i i) MOLECULE TYPE:
    (A) DESCRIPTION: OTHER NUCLEIC ACID (i i i) HYPOTHETICAL: YES (i v) ANTI-SENSE: NO (i x) FEATURE:
    (A) NAME/KEY:
    (B) LOCATION:
    (C) IDENTIFICATION METHOD:
    (D) OTHER INFORMATION:

(x i) SEQUENCE DESCRIPTION: SEQ ID NO: 49:

GACTGACGAT GTGAAAAGTA TTG 23

(2) INFORMATION FOR SEQ ID NO:50:

(i) SEQUENCE CHARACTERISTICS:
    (A) LENGTH: 23
    (B) TYPE: NUCLEIC ACID
    (C) STRANDEDNESS: SINGLE
    (D) TOPOLOGY: LINEAR (i i) MOLECULE TYPE:
    (A) DESCRIPTION: OTHER NUCLEIC ACID (i i i) HYPOTHETICAL: YES (i v) ANTI-SENSE: NO (i x) FEATURE:
    (A) NAME/KEY:
    (B) LOCATION:
    (C) IDENTIFICATION METHOD:
    (D) OTHER INFORMATION:

(x i) SEQUENCE DESCRIPTION: SEQ ID NO: 50:

CCAGTCAGGT ATATTTGGAA AAG 23

(2) INFORMATION FOR SEQ ID NO:51:

(i) SEQUENCE CHARACTERISTICS:
    (A) LENGTH: 21
    (B) TYPE: NUCLEIC ACID
    (C) STRANDEDNESS: SINGLE
    (D) TOPOLOGY: LINEAR (i i) MOLECULE TYPE:

(A) DESCRIPTION: OTHER NUCLEIC ACID (iii) HYPOTHETICAL: YES (iv) ANTI-SENSE: NO (ix) FEATURE:
    (A) NAME/KEY:
    (B) LOCATION:
    (C) IDENTIFICATION METHOD:
    (D) OTHER INFORMATION:

(xi) SEQUENCE DESCRIPTION: SEQ ID NO: 51:

CGATCGCTTA TGTGATGCTC G 21

(2) INFORMATION FOR SEQ ID NO:52:

(i) SEQUENCE CHARACTERISTICS:
    (A) LENGTH: 23
    (B) TYPE: NUCLEIC ACID
    (C) STRANDEDNESS: SINGLE
    (D) TOPOLOGY: LINEAR (ii) MOLECULE TYPE:
    (A) DESCRIPTION: OTHER NUCLEIC ACID (iii) HYPOTHETICAL: YES (iv) ANTI-SENSE: NO (ix) FEATURE:
    (A) NAME/KEY:
    (B) LOCATION:
    (C) IDENTIFICATION METHOD:
    (D) OTHER INFORMATION:

(xi) SEQUENCE DESCRIPTION: SEQ ID NO: 52:

GAACTTACAG AAGTCTGCAA ATC 23

(2) INFORMATION FOR SEQ ID NO:53:

(i) SEQUENCE CHARACTERISTICS:
    (A) LENGTH: 22
    (B) TYPE: NUCLEIC ACID
    (C) STRANDEDNESS: SINGLE
    (D) TOPOLOGY: LINEAR (ii) MOLECULE TYPE:
    (A) DESCRIPTION: OTHER NUCLEIC ACID (iii) HYPOTHETICAL: YES (iv) ANTI-SENSE: NO (ix) FEATURE:
    (A) NAME/KEY:
    (B) LOCATION:
    (C) IDENTIFICATION METHOD:
    (D) OTHER INFORMATION:

(xi) SEQUENCE DESCRIPTION: SEQ ID NO: 53:

GGTGTTACTG AAGACAAACT GG 22

(2) INFORMATION FOR SEQ ID NO:54:

(i) SEQUENCE CHARACTERISTICS:
    (A) LENGTH: 20
    (B) TYPE: NUCLEIC ACID
    (C) STRANDEDNESS: SINGLE
    (D) TOPOLOGY: LINEAR (ii) MOLECULE TYPE:
    (A) DESCRIPTION: OTHER NUCLEIC ACID (iii) HYPOTHETICAL: YES (iv) ANTI-SENSE: NO (ix) FEATURE:
   (A) NAME/KEY:
   (B) LOCATION:
   (C) IDENTIFICATION METHOD:
   (D) OTHER INFORMATION:

(xi) SEQUENCE DESCRIPTION: SEQ ID NO: 54:

GGATAAGCCT GTCCAGCAGC  20

(2) INFORMATION FOR SEQ ID NO:55:

(i) SEQUENCE CHARACTERISTICS:
      (A) LENGTH: 20
      (B) TYPE: NUCLEIC ACID
      (C) STRANDEDNESS: SINGLE
      (D) TOPOLOGY: LINEAR (ii) MOLECULE TYPE:
      (A) DESCRIPTION: OTHER NUCLEIC ACID (iii) HYPOTHETICAL: YES (iv) ANTI-SENSE: NO (ix) FEATURE:
      (A) NAME/KEY:
      (B) LOCATION:
      (C) IDENTIFICATION METHOD:
      (D) OTHER INFORMATION:

(xi) SEQUENCE DESCRIPTION: SEQ ID NO: 55:

GCTTCCAGTG GTTCCAAGGC  20

(2) INFORMATION FOR SEQ ID NO:56:

(i) SEQUENCE CHARACTERISTICS:
      (A) LENGTH: 20
      (B) TYPE: NUCLEIC ACID
      (C) STRANDEDNESS: SINGLE
      (D) TOPOLOGY: LINEAR (ii) MOLECULE TYPE:
      (A) DESCRIPTION: OTHER NUCLEIC ACID (iii) HYPOTHETICAL: YES (iv) ANTI-SENSE: NO (ix) FEATURE:
      (A) NAME/KEY:
      (B) LOCATION:
      (C) IDENTIFICATION METHOD:
      (D) OTHER INFORMATION:

(xi) SEQUENCE DESCRIPTION: SEQ ID NO: 56:

CTCAAGCGAC ATCAGGAGCC  20

(2) INFORMATION FOR SEQ ID NO:57:

(i) SEQUENCE CHARACTERISTICS:
      (A) LENGTH: 20
      (B) TYPE: NUCLEIC ACID
      (C) STRANDEDNESS: SINGLE
      (D) TOPOLOGY: LINEAR (ii) MOLECULE TYPE:
      (A) DESCRIPTION: OTHER NUCLEIC ACID (iii) HYPOTHETICAL: YES ( i v ) ANTI-SENSE: NO ( i x ) FEATURE:
    ( A ) NAME/KEY:
    ( B ) LOCATION:
    ( C ) IDENTIFICATION METHOD:
    ( D ) OTHER INFORMATION:

( x i ) SEQUENCE DESCRIPTION: SEQ ID NO: 57:

GCCATCACCG GAACAGAAGG 20

( 2 ) INFORMATION FOR SEQ ID NO:58:

( i ) SEQUENCE CHARACTERISTICS:
        ( A ) LENGTH: 23
        ( B ) TYPE: NUCLEIC ACID
        ( C ) STRANDEDNESS: SINGLE
        ( D ) TOPOLOGY: LINEAR ( i i ) MOLECULE TYPE:
        ( A ) DESCRIPTION: OTHER NUCLEIC ACID ( i i i ) HYPOTHETICAL: YES ( i v ) ANTI-SENSE: NO ( i x ) FEATURE:
        ( A ) NAME/KEY:
        ( B ) LOCATION:
        ( C ) IDENTIFICATION METHOD:
        ( D ) OTHER INFORMATION:

( x i ) SEQUENCE DESCRIPTION: SEQ ID NO: 58:

GATTATGTCT GTTAAAGCTC ATG 23

( 2 ) INFORMATION FOR SEQ ID NO:59:

( i ) SEQUENCE CHARACTERISTICS:
        ( A ) LENGTH: 20
        ( B ) TYPE: NUCLEIC ACID
        ( C ) STRANDEDNESS: SINGLE
        ( D ) TOPOLOGY: LINEAR ( i i ) MOLECULE TYPE:
        ( A ) DESCRIPTION: OTHER NUCLEIC ACID ( i i i ) HYPOTHETICAL: YES ( i v ) ANTI-SENSE: NO ( i x ) FEATURE:
        ( A ) NAME/KEY:
        ( B ) LOCATION:
        ( C ) IDENTIFICATION METHOD:
        ( D ) OTHER INFORMATION:

( x i ) SEQUENCE DESCRIPTION: SEQ ID NO: 59:

CGTGTCAGCC ATGGTGTCAC 20

( 2 ) INFORMATION FOR SEQ ID NO:60:

( i ) SEQUENCE CHARACTERISTICS:
        ( A ) LENGTH: 21
        ( B ) TYPE: NUCLEIC ACID
        ( C ) STRANDEDNESS: SINGLE
        ( D ) TOPOLOGY: LINEAR ( i i ) MOLECULE TYPE:
        ( A ) DESCRIPTION: OTHER NUCLEIC ACID ( i i i ) HYPOTHETICAL: YES ( i v ) ANTI-SENSE: NO ( i x ) FEATURE:
    ( A ) NAME/KEY:
    ( B ) LOCATION:
    ( C ) IDENTIFICATION METHOD:
    ( D ) OTHER INFORMATION:

( x i ) SEQUENCE DESCRIPTION: SEQ ID NO: 60:

CAGATAACCT GACAGCCATC C            21

( 2 ) INFORMATION FOR SEQ ID NO:61:

( i ) SEQUENCE CHARACTERISTICS:
    ( A ) LENGTH: 22
    ( B ) TYPE: NUCLEIC ACID
    ( C ) STRANDEDNESS: SINGLE
    ( D ) TOPOLOGY: LINEAR ( i i ) MOLECULE TYPE:
    ( A ) DESCRIPTION: OTHER NUCLEIC ACID ( i i i ) HYPOTHETICAL: YES ( i v ) ANTI-SENSE: NO ( i x ) FEATURE:
    ( A ) NAME/KEY:
    ( B ) LOCATION:
    ( C ) IDENTIFICATION METHOD:
    ( D ) OTHER INFORMATION:

( x i ) SEQUENCE DESCRIPTION: SEQ ID NO: 61:

CAGTCTGGTC ACATCATGAT AG            22

( 2 ) INFORMATION FOR SEQ ID NO:62:

( i ) SEQUENCE CHARACTERISTICS:
    ( A ) LENGTH: 21
    ( B ) TYPE: NUCLEIC ACID
    ( C ) STRANDEDNESS: SINGLE
    ( D ) TOPOLOGY: LINEAR ( i i ) MOLECULE TYPE:
    ( A ) DESCRIPTION: OTHER NUCLEIC ACID ( i i i ) HYPOTHETICAL: YES ( i v ) ANTI-SENSE: NO ( i x ) FEATURE:
    ( A ) NAME/KEY:
    ( B ) LOCATION:
    ( C ) IDENTIFICATION METHOD:
    ( D ) OTHER INFORMATION:

( x i ) SEQUENCE DESCRIPTION: SEQ ID NO: 62:

GCTGTATTCT CCTGCATTCC G            21

( 2 ) INFORMATION FOR SEQ ID NO:63:

( i ) SEQUENCE CHARACTERISTICS:
    ( A ) LENGTH: 23
    ( B ) TYPE: NUCLEIC ACID
    ( C ) STRANDEDNESS: SINGLE
    ( D ) TOPOLOGY: LINEAR ( i i ) MOLECULE TYPE:
    ( A ) DESCRIPTION: OTHER NUCLEIC ACID ( i i i ) HYPOTHETICAL: YES ( i v ) ANTI-SENSE: NO ( i x ) FEATURE:
    ( A ) NAME/KEY:

(B) LOCATION:
            (C) IDENTIFICATION METHOD:
            (D) OTHER INFORMATION:

(xi) SEQUENCE DESCRIPTION: SEQ ID NO: 63:

CCTTGTGATG AACTATGTTC TTG                                                                          23

(2) INFORMATION FOR SEQ ID NO:64:

(i) SEQUENCE CHARACTERISTICS:
            (A) LENGTH: 23
            (B) TYPE: NUCLEIC ACID
            (C) STRANDEDNESS: SINGLE
            (D) TOPOLOGY: LINEAR (ii) MOLECULE TYPE:
            (A) DESCRIPTION: OTHER NUCLEIC ACID (iii) HYPOTHETICAL: YES (iv) ANTI-SENSE: NO (ix) FEATURE:
            (A) NAME/KEY:
            (B) LOCATION:
            (C) IDENTIFICATION METHOD:
            (D) OTHER INFORMATION:

(xi) SEQUENCE DESCRIPTION: SEQ ID NO: 64:

CCAAAATCTT GTCAAGTATC AGC                                                                          23

(2) INFORMATION FOR SEQ ID NO:65:

(i) SEQUENCE CHARACTERISTICS:
            (A) LENGTH: 24
            (B) TYPE: NUCLEIC ACID
            (C) STRANDEDNESS: SINGLE
            (D) TOPOLOGY: LINEAR (ii) MOLECULE TYPE:
            (A) DESCRIPTION: OTHER NUCLEIC ACID (iii) HYPOTHETICAL: YES (iv) ANTI-SENSE: NO (ix) FEATURE:
            (A) NAME/KEY:
            (B) LOCATION:
            (C) IDENTIFICATION METHOD:
            (D) OTHER INFORMATION:

(xi) SEQUENCE DESCRIPTION: SEQ ID NO: 65:

GGAATTTTCT GTTTCCATAA AGTC                                                                         24

(2) INFORMATION FOR SEQ ID NO:66:

(i) SEQUENCE CHARACTERISTICS:
            (A) LENGTH: 21
            (B) TYPE: NUCLEIC ACID
            (C) STRANDEDNESS: SINGLE
            (D) TOPOLOGY: LINEAR (ii) MOLECULE TYPE:
            (A) DESCRIPTION: OTHER NUCLEIC ACID (iii) HYPOTHETICAL: YES (iv) ANTI-SENSE: NO (ix) FEATURE:
            (A) NAME/KEY:
            (B) LOCATION:
            (C) IDENTIFICATION METHOD:

5,824,501

63

64

-continued (D) OTHER INFORMATION:

(xi) SEQUENCE DESCRIPTION: SEQ ID NO: 66:

CAAGCTTCTT GAGAGTGACG G                                                                 21

(2) INFORMATION FOR SEQ ID NO:67:

(i) SEQUENCE CHARACTERISTICS:
                (A) LENGTH: 23
                (B) TYPE: NUCLEIC ACID
                (C) STRANDEDNESS: SINGLE
                (D) TOPOLOGY: LINEAR (ii) MOLECULE TYPE:
                (A) DESCRIPTION: OTHER NUCLEIC ACID (iii) HYPOTHETICAL: YES (iv) ANTI-SENSE: NO (ix) FEATURE:
                (A) NAME/KEY:
                (B) LOCATION:
                (C) IDENTIFICATION METHOD:
                (D) OTHER INFORMATION:

(xi) SEQUENCE DESCRIPTION: SEQ ID NO: 67:

GATGTCCATT CAGAGTATTT CTG                                                                23

(2) INFORMATION FOR SEQ ID NO:68:

(i) SEQUENCE CHARACTERISTICS:
                (A) LENGTH: 21
                (B) TYPE: NUCLEIC ACID
                (C) STRANDEDNESS: SINGLE
                (D) TOPOLOGY: LINEAR (ii) MOLECULE TYPE:
                (A) DESCRIPTION: OTHER NUCLEIC ACID (iii) HYPOTHETICAL: YES (iv) ANTI-SENSE: NO (ix) FEATURE:
                (A) NAME/KEY:
                (B) LOCATION:
                (C) IDENTIFICATION METHOD:
                (D) OTHER INFORMATION:

(xi) SEQUENCE DESCRIPTION: SEQ ID NO: 68:

GGGTATTTCC TCGTCAAGCT C                                                                 21

(2) INFORMATION FOR SEQ ID NO:69:

(i) SEQUENCE CHARACTERISTICS:
                (A) LENGTH: 23
                (B) TYPE: NUCLEIC ACID
                (C) STRANDEDNESS: SINGLE
                (D) TOPOLOGY: LINEAR (ii) MOLECULE TYPE:
                (A) DESCRIPTION: OTHER NUCLEIC ACID (iii) HYPOTHETICAL: YES (iv) ANTI-SENSE: NO (ix) FEATURE:
                (A) NAME/KEY:
                (B) LOCATION:
                (C) IDENTIFICATION METHOD:
                (D) OTHER INFORMATION:

-continued (x i) SEQUENCE DESCRIPTION: SEQ ID NO: 69:

CCTAGATATC TTTCTACATG TGG    23

(2) INFORMATION FOR SEQ ID NO:70:

(i) SEQUENCE CHARACTERISTICS:
        (A) LENGTH: 23
        (B) TYPE: NUCLEIC ACID
        (C) STRANDEDNESS: SINGLE
        (D) TOPOLOGY: LINEAR (i i) MOLECULE TYPE:
        (A) DESCRIPTION: OTHER NUCLEIC ACID (i i i) HYPOTHETICAL: YES (i v) ANTI-SENSE: NO (i x) FEATURE:
        (A) NAME/KEY:
        (B) LOCATION:
        (C) IDENTIFICATION METHOD:
        (D) OTHER INFORMATION:

(x i) SEQUENCE DESCRIPTION: SEQ ID NO: 70:

GTTATGAGAA TGCATATGAA GGC    23

(2) INFORMATION FOR SEQ ID NO:71:

(i) SEQUENCE CHARACTERISTICS:
        (A) LENGTH: 24
        (B) TYPE: NUCLEIC ACID
        (C) STRANDEDNESS: SINGLE
        (D) TOPOLOGY: LINEAR (i i) MOLECULE TYPE:
        (A) DESCRIPTION: OTHER NUCLEIC ACID (i i i) HYPOTHETICAL: YES (i v) ANTI-SENSE: NO (i x) FEATURE:
        (A) NAME/KEY:
        (B) LOCATION:
        (C) IDENTIFICATION METHOD:
        (D) OTHER INFORMATION:

(x i) SEQUENCE DESCRIPTION: SEQ ID NO: 71:

CAAGAATAAC AGCTTTATAG TCAC    24

(2) INFORMATION FOR SEQ ID NO:72:

(i) SEQUENCE CHARACTERISTICS:
        (A) LENGTH: 4437
        (B) TYPE: NUCLEIC ACID
        (C) STRANDEDNESS: SINGLE
        (D) TOPOLOGY: LINEAR (i i) MOLECULE TYPE:
        (A) DESCRIPTION: OTHER NUCLEIC ACID (i i i) HYPOTHETICAL: YES (i v) ANTI-SENSE: NO (i x) FEATURE:
        (A) NAME/KEY:
        (B) LOCATION:
        (C) IDENTIFICATION METHOD:
        (D) OTHER INFORMATION:

(x i) SEQUENCE DESCRIPTION: SEQ ID NO: 72:

-continued

| | | | | | |
|---|---|---|---|---|---|
| GCGCGGCGGC | CGTGGTTGCG | GCGCGGGAAG | TTTGGATCCT | GGTTCCGTCC | GCTAGGAGTC | 60 |
| TGCGTGCGAG | GATTATGGCT | GCTGTTCCTC | AAAATAATCT | ACAGGAGCAA | CTAGAACGTC | 120 |
| ACTCAGCCAG | AACACTTAAT | AATAAATTAA | GTCTTTCAAA | ACCAAAATTT | TCAGGTTTCA | 180 |
| CTTTTAAAAA | GAAAACATCT | TCAGATAACA | ATGTATCTGT | AACTAATGTG | TCAGTAGCAA | 240 |
| AAACACCTGT | ATTAAGAAAT | AAAGATGTTA | ATGTTACCGA | AGACTTTTCC | TTCAGTGAAC | 300 |
| CTCTACCCAA | CACCACAAAT | CAGCAAAGGG | TCAAGGACTT | CTTTAAAAAT | GCTCCAGCAG | 360 |
| GACAGGAAAC | ACAGAGAGGT | GGATCAAAAT | CATTATTGCC | AGATTTCTTG | CAGACTCCGA | 420 |
| AGGAAGTTGT | ATGCACTACC | CAAAACACAC | CAACTGTAAA | GAAATCCCGG | GATACTGCTC | 480 |
| TCAAGAAATT | AGAATTTAGT | TCTTCACCAG | ATTCTTTAAG | TACCATCAAT | GATTGGGATG | 540 |
| ATATGGATGA | CTTTGATACT | TCTGAGACTT | CAAAATCATT | TGTTACACCA | CCCCAAAGTC | 600 |
| ACTTTGTAAG | AGTAAGCACT | GCTCAGAAAT | CAAAAAGGG | TAAGAGAAAC | TTTTTAAAG | 660 |
| CACAGCTTTA | TACAACAAAC | ACAGTAAAGA | CTGATTTGCC | TCCACCCTCC | TCTGAAAGCG | 720 |
| AGCAAATAGA | TTTGACTGAG | GAACAGAAGG | ATGACTCAGA | ATGGTTAAGC | AGCGATGTGA | 780 |
| TTTGCATCGA | TGATGGCCCC | ATTGCTGAAG | TGCATATAAA | TGAAGATGCT | CAGGAAAGTG | 840 |
| ACTCTCTGAA | AACTCATTTG | GAAGATGAAA | GAGATAATAG | CGAAAAGAAG | AAGAATTTGG | 900 |
| AAGAAGCTGA | ATTACATTCA | ACTGAGAAAG | TTCCATGTAT | TGAATTTGAT | GATGATGATT | 960 |
| ATGATACGGA | TTTTGTTCCA | CCTTCTCCAG | AAGAAATTAT | TTCTGCTTCT | TCTTCCTCTT | 1020 |
| CAAAATGCCT | TACTACGTTA | AAGGACCTTG | ACACATCTGA | CAGAAAAGAG | GATGTTCTTA | 1080 |
| GCACATCAAA | AGATCTTTTG | TCAAAACCTG | AGAAAATGAG | TATGCAGGAG | CTGAATCCAG | 1140 |
| AAACCAGCAC | AGACTGTGAC | GCTAGACAGA | TAAGTTTACA | GCAGCAGCTT | ATTCATGTGA | 1200 |
| TGGAGCACAT | CTGTAAATTA | ATTGATACTA | TTCCTGATGA | TAAACTGAAA | CTTTTGGATT | 1260 |
| GTGGGAACGA | ACTGCTTCAG | CAGCGGAACA | TAAGAAGGAA | ACTTCTAACG | GAAGTAGATT | 1320 |
| TTAATAAAAG | TGATGCCAGT | CTTCTTGGCT | CATTGTGGAG | ATACAGGCCT | GATTCACTTG | 1380 |
| ATGGCCCTAT | GGAGGGTGAT | TCCTGCCCTA | CAGGGAATTC | TATGAAGGAG | TTAAATTTTT | 1440 |
| CACACCTTCC | CTCAAATTCT | GTTTCTCCTG | GGACTGTTT | ACTGACTACC | ACCCTAGGAA | 1500 |
| AGACAGGATT | CTCTGCCACC | AGGAAGAATC | TTTTTGAAAG | GCCTTTATTC | AATACCCATT | 1560 |
| TACAGAAGTC | CTTTGTAAGT | AGCAACTGGG | CTGAAACACC | AAGACTAGGA | AAAAAAAATG | 1620 |
| AAAGCTCTTA | TTTCCCAGGA | AATGTTCTCA | CAAGCACTGC | TGTGAAAGAT | CAGAATAAAC | 1680 |
| ATACTGCTTC | AATAAATGAC | TTAGAAAGAG | AAACCCAACC | TTCCTATGAT | ATTGATAATT | 1740 |
| TTGACATAGA | TGACTTTGAT | GATGATGATG | ACTGGGAAGA | CATAATGCAT | AATTTAGCAG | 1800 |
| CCAGCAAATC | TTCCACAGCT | GCCTATCAAC | CCATCAAGGA | AGGTCGGCCA | ATTAAATCAG | 1860 |
| TATCAGAAAG | ACTTTCCTCA | GCCAAGACAG | ACTGTCTTCC | AGTGTCATCT | ACTGCTCAAA | 1920 |
| ATATAAACTT | CTCAGAGTCA | ATTCAGAATT | ATACTGACAA | GTCAGCACAA | AATTTAGCAT | 1980 |
| CCAGAAATCT | GAAACATGAG | CGTTTCCAAA | GTCTTAGTTT | TCCTCATACA | AAGGAAATGA | 2040 |
| TGAAGATTTT | TCATAAAAAA | TTTGGCCTGC | ATAATTTAG | AACTAATCAG | CTAGAGGCGA | 2100 |
| TCAATGCTGC | ACTGCTTGGT | GAAGACTGTT | TTATCCTGAT | GCCGACTGGA | GGTGGTAAGA | 2160 |
| GTTTGTGTTA | CCAGCTCCCT | GCCTGTGTTT | CTCCTGGGGT | CACTGTTGTC | ATTTCTCCCT | 2220 |
| TGAGATCACT | TATCGTAGAT | CAAGTCCAAA | AGCTGACTTC | CTTGGATATT | CCAGCTACAT | 2280 |
| ATCTGACAGG | TGATAAGACT | GACTCAGAAG | CTACAAATAT | TTACCTCCAG | TTATCAAAAA | 2340 |
| AAGACCCAAT | CATAAAACTT | CTATATGTCA | CTCCAGAAAA | GATCTGTGCA | AGTAACAGAC | 2400 |

| | | | | | | |
|---|---|---|---|---|---|---|
| TCATTTCTAC | TCTGGAGAAT | CTCTATGAGA | GGAAGCTCTT | GGCACGTTTT | GTTATTGATG | 2460 |
| AAGCACATTG | TGTCAGTCAG | TGGGGACATG | ATTTTCGTCA | AGATTACAAA | AGAATGAATA | 2520 |
| TGCTTCGCCA | GAAGTTTCCT | TCTGTTCCGG | TGATGGCTCT | TACGGCCACA | GCTAATCCCA | 2580 |
| GGGTACAGAA | GGACATCCTG | ACTCAGCTGA | AGATTCTCAG | ACCTCAGGTG | TTTAGCATGA | 2640 |
| GCTTTAACAG | ACATAATCTG | AAATACTATG | TATTACCGAA | AAAGCCTAAA | AAGGTGGCAT | 2700 |
| TTGATTGCCT | AGAATGGATC | AGAAAGCACC | ACCCATATGA | TTCAGGGATA | ATTTACTGCC | 2760 |
| TCTCCAGGCG | AGAATGTGAC | ACCATGGCTG | ACACGTTACA | GAGAGATGGG | CTCGCTGCTC | 2820 |
| TTGCTTACCA | TGCTGGCCTC | AGTGATTCTG | CCAGAGATGA | AGTGCAGCAG | AAGTGGATTA | 2880 |
| ATCAGGATGG | CTGTCAGGTT | ATCTGTGCTA | CAATTGCATT | TGGAATGGGG | ATTGACAAAC | 2940 |
| CGGACGTGCG | ATTTGTGATT | CATGCATCTC | TCCCTAAATC | TGTGGAGGGT | TACTACCAAG | 3000 |
| AATCTGGCAG | AGCTGGAAGA | GATGGGGAAA | TATCTCACTG | CCTGCTTTTC | TATACCTATC | 3060 |
| ATGATGTGAC | CAGACTGAAA | AGACTTATAA | TGATGGAAAA | AGATGGAAAC | CATCATACAA | 3120 |
| GAGAAACTCA | CTTCAATAAT | TTGTATAGCA | TGGTACATTA | CTGTGAAAAT | ATAACGGAAT | 3180 |
| GCAGGAGAAT | ACAGCTTTTG | GCCTACTTTG | GTGAAATGG | ATTTAATCCT | GATTTTTGTA | 3240 |
| AGAAACACCC | AGATGTTTCT | TGTGATAATT | GCTGTAAAAC | AAAGGATTAT | AAAACAAGAG | 3300 |
| ATGTGACTGA | CGATGTGAAA | AGTATTGTAA | GATTTGTTCA | AGAACATAGT | TCATCACAAG | 3360 |
| GAATGAGAAA | TATAAAACAT | GTAGGTCCTT | CTGGAAGATT | TACTATGAAT | ATGCTGGTCG | 3420 |
| ACATTTTCTT | GGGGAGTAAG | AGTGCAAAAA | TCCAGTCAGG | TATATTTGGA | AAAGGATCTG | 3480 |
| CTTATTCACG | ACACAATGCC | GAAAGACTTT | TTAAAAAGCT | GATACTTGAC | AAGATTTTGG | 3540 |
| ATGAAGACTT | ATATATCAAT | GCCAATGACC | AGGCGATCGC | TTATGTGATG | CTCGGAAATA | 3600 |
| AAGCCCAAAC | TGTACTAAAT | GGCAATTTAA | AGGTAGACTT | TATGGAAACA | GAAAATTCCA | 3660 |
| GCAGTGTGAA | AAAACAAAAA | GCGTTAGTAG | CAAAAGTGTC | TCAGAGGGAA | GAGATGGTTA | 3720 |
| AAAAATGTCT | TGGAGAACTT | ACAGAAGTCT | GCAAATCTCT | GGGGAAAGTT | TTTGGTGTCC | 3780 |
| ATTACTTCAA | TATTTTTAAT | ACCGTCACTC | TCAAGAAGCT | TGCAGAATCT | TTATCTTCTG | 3840 |
| ATCCTGAGGT | TTTGCTTCAA | ATTGATGGTG | TTACTGAAGA | CAAACTGGAA | AAATATGGTG | 3900 |
| CGGAAGTGAT | TTCAGTATTA | CAGAAATACT | CTGAATGGAC | ATCGCCAGCT | GAAGACAGTT | 3960 |
| CCCCAGGGAT | AAGCCTGTCC | AGCAGCAGAG | GCCCCGGAAG | AAGTGCCGCT | GAGGAGCTTG | 4020 |
| ACGAGGAAAT | ACCCGTATCT | TCCACTACT | TTGCAAGTAA | AACCAGAAAT | GAAAGGAAGA | 4080 |
| GGAAAAAGAT | GCCAGCCTCC | CAAAGGTCTA | AGAGGAGAAA | AACTGCTTCC | AGTGGTTCCA | 4140 |
| AGGCAAAGGG | GGGGTCTGCC | ACATGTAGAA | AGATATCTTC | CAAAACGAAA | TCCTCCAGCA | 4200 |
| TCATTGGATC | CAGTTCAGCC | TCACATACTT | CTCAAGCGAC | ATCAGGAGCC | AATAGCAAAT | 4260 |
| TGGGGATTAT | GGCTCCACCG | AAGCCTATAA | ATAGACCGTT | TCTTAAGCCT | TCATATGCAT | 4320 |
| TCTCATAACA | ACCGAATCTC | AATGTACATA | GACCCTCTTT | CTTGTTTGTC | AGCATCTGAC | 4380 |
| CATCTGTGAC | TATAAAGCTG | TTATTCTTGT | TATACCAAAA | AAAAAAAAA | AAAAAA | 4437 |

( 2 ) INFORMATION FOR SEQ ID NO:73:

( i ) SEQUENCE CHARACTERISTICS:
        ( A ) LENGTH: 65
        ( B ) TYPE: NUCLEIC ACID
        ( C ) STRANDEDNESS: SINGLE
        ( D ) TOPOLOGY: LINEAR ( i i ) MOLECULE TYPE:
        ( A ) DESCRIPTION: OTHER NUCLEIC ACID ( i i i ) HYPOTHETICAL: YES ( i v ) ANTI-SENSE: NO ( i x ) FEATURE:
- ( A ) NAME/KEY:
- ( B ) LOCATION:
- ( C ) IDENTIFICATION METHOD:
- ( D ) OTHER INFORMATION:

( x i ) SEQUENCE DESCRIPTION: SEQ ID NO: 73:

```
GCTTCCGGCG GAAGTGAGCC AGGGCTTGGC GCGGCGGCCG TGGTTGCGGC        50
GCGGGAAGTT TGGAT                                              65
```

( 2 ) INFORMATION FOR SEQ ID NO:74:

- ( i ) SEQUENCE CHARACTERISTICS:
  - ( A ) LENGTH: 393
  - ( B ) TYPE: AMINO ACID
  - ( C ) STRANDEDNESS: SINGLE
  - ( D ) TOPOLOGY: LINEAR

- ( i i ) MOLECULE TYPE:
  - ( A ) DESCRIPTION: OTHER NUCLEIC ACID

- ( i i i ) HYPOTHETICAL: YES

- ( i v ) ANTI-SENSE: NO

- ( i x ) FEATURE:
  - ( A ) NAME/KEY:
  - ( B ) LOCATION:
  - ( C ) IDENTIFICATION METHOD:
  - ( D ) OTHER INFORMATION:

- ( x i ) SEQUENCE DESCRIPTION: SEQ ID NO: 74:

```
Phe Pro His Thr Lys Glu Met Met Lys Ile Phe His Lys Lys Phe
  1           5                  10                      15

Gly Leu His Asn Phe Arg Thr Asn Gln Leu Glu Ala Ile Asn Ala
             20                  25                      30

Ala Leu Leu Gly Glu Asp Cys Phe Ile Leu Met Pro Thr Gly Gly
             35                  40                      45

Gly Lys Ser Leu Cys Tyr Gln Leu Pro Ala Cys Val Ser Pro Gly
             50                  55                      60

Val Thr Val Val Ile Ser Pro Leu Arg Ser Leu Ile Val Asp Gln
             65                  70                      75

Val Gln Lys Leu Thr Ser Leu Asp Ile Pro Ala Thr Tyr Leu Thr
             80                  85                      90

Gly Asp Lys Thr Asp Ser Glu Ala Thr Asn Ile Tyr Leu Gln Leu
             95                 100                     105

Ser Lys Lys Asp Pro Ile Ile Lys Leu Leu Tyr Val Thr Pro Glu
            110                 115                     120

Lys Ile Cys Ala Ser Asn Arg Leu Ile Ser Thr Leu Glu Asn Leu
            125                 130                     135

Tyr Glu Arg Lys Leu Leu Ala Arg Phe Val Ile Asp Glu Ala His
            140                 145                     150

Cys Val Ser Gln Trp Gly His Asp Phe Arg Gln Asp Tyr Lys Arg
            155                 160                     165

Met Asn Met Leu Arg Gln Lys Phe Pro Ser Val Pro Val Met Ala
            170                 175                     180

Leu Thr Ala Thr Ala Asn Pro Arg Val Gln Lys Asp Ile Leu Thr
            185                 190                     195

Gln Leu Lys Ile Leu Arg Pro Gln Val Phe Ser Met Ser Phe Asn
            200                 205                     210
```

| Arg | His | Asn | Leu | Lys<br>215 | Tyr | Tyr | Val | Leu | Pro<br>220 | Lys | Lys | Pro | Lys<br>225 |

| Val | Ala | Phe | Asp | Cys<br>230 | Leu | Glu | Trp | Ile | Arg<br>235 | Lys | His | His | Pro | Tyr<br>240 |

| Asp | Ser | Gly | Ile | Ile<br>245 | Tyr | Cys | Leu | Ser | Arg<br>250 | Arg | Glu | Cys | Asp | Thr<br>255 |

| Met | Ala | Asp | Thr | Leu<br>260 | Gln | Arg | Asp | Gly | Leu<br>265 | Ala | Ala | Leu | Ala | Tyr<br>270 |

| His | Ala | Gly | Leu | Ser<br>275 | Asp | Ser | Ala | Arg | Asp<br>280 | Glu | Val | Gln | Gln | Lys<br>285 |

| Trp | Ile | Asn | Gln | Asp<br>290 | Gly | Cys | Gln | Val | Ile<br>295 | Cys | Ala | Thr | Ile | Ala<br>300 |

| Phe | Gly | Met | Gly | Ile<br>305 | Asp | Lys | Pro | Asp | Val<br>310 | Arg | Phe | Val | Ile | His<br>315 |

| Ala | Ser | Leu | Pro | Lys<br>320 | Ser | Val | Glu | Gly | Tyr<br>325 | Tyr | Gln | Glu | Ser | Gly<br>330 |

| Arg | Ala | Gly | Arg | Asp<br>335 | Gly | Glu | Ile | Ser | His<br>340 | Cys | Leu | Leu | Phe | Tyr<br>345 |

| Thr | Tyr | His | Asp | Val<br>350 | Thr | Arg | Leu | Lys | Arg<br>355 | Leu | Ile | Met | Met | Glu<br>360 |

| Lys | Asp | Gly | Asn | His<br>365 | His | Thr | Arg | Glu | Thr<br>370 | His | Phe | Asn | Asn | Leu<br>375 |

| Tyr | Ser | Met | Val | His<br>380 | Tyr | Cys | Glu | Asn | Ile<br>385 | Thr | Glu | Cys | Arg | Arg<br>390 |

| Ile | Gln | Leu |

(2) INFORMATION FOR SEQ ID NO:75:

(i) SEQUENCE CHARACTERISTICS:
        (A) LENGTH: 386
        (B) TYPE: AMINO ACID
        (C) STRANDEDNESS: SINGLE
        (D) TOPOLOGY: LINEAR (ii) MOLECULE TYPE:
        (A) DESCRIPTION: OTHER NUCLEIC ACID (iii) HYPOTHETICAL: YES (iv) ANTI-SENSE: NO (ix) FEATURE:
        (A) NAME/KEY:
        (B) LOCATION:
        (C) IDENTIFICATION METHOD:
        (D) OTHER INFORMATION:

(xi) SEQUENCE DESCRIPTION: SEQ ID NO: 75:

| Phe<br>1 | Pro | Trp | Ser | Gly<br>5 | Lys | Val | Lys | Asp | Ile<br>10 | Leu | Gln | Asn | Val | Phe<br>15 |

| Lys | Leu | Glu | Lys | Phe<br>20 | Arg | Pro | Leu | Gln | Leu<br>25 | Glu | Thr | Ile | Asn | Val<br>30 |

| Thr | Met | Ala | Gly | Lys<br>35 | Glu | Val | Phe | Leu | Val<br>40 | Met | Pro | Thr | Gly | Gly<br>45 |

| Gly | Lys | Ser | Leu | Cys<br>50 | Tyr | Gln | Leu | Pro | Ala<br>55 | Leu | Cys | Ser | Asp | Gly<br>60 |

| Phe | Thr | Leu | Val | Ile<br>65 | Cys | Pro | Leu | Ile | Ser<br>70 | Leu | Met | Glu | Asp | Gln<br>75 |

| Leu | Met | Val | Leu | Lys<br>80 | Gln | Leu | Gly | Ile | Ser<br>85 | Ala | Thr | Met | Leu | Asn<br>90 |

```
Ala  Ser  Ser  Ser  Lys  Glu  His  Val  Lys  Trp  Val  His  Asp  Glu  Met
               95                  100                           105

Val  Asn  Lys  Asn  Ser  Glu  Leu  Lys  Leu  Ile  Tyr  Val  Thr  Pro  Glu
               110                 115                           120

Lys  Ile  Ala  Lys  Ser  Lys  Met  Phe  Met  Ser  Arg  Leu  Glu  Lys  Ala
               125                 130                           135

Tyr  Glu  Ala  Arg  Arg  Phe  Thr  Arg  Ile  Ala  Val  Asp  Glu  Val  His
               140                 145                           150

Cys  Cys  Ser  Gln  Trp  Gly  His  Asp  Phe  Arg  Pro  Asp  Tyr  Lys  Ala
               155                 160                           165

Leu  Gly  Ile  Leu  Lys  Arg  Gln  Phe  Pro  Asn  Ala  Ser  Leu  Ile  Gly
               170                 175                           180

Leu  Thr  Ala  Thr  Ala  Thr  Asn  His  Val  Leu  Thr  Asp  Ala  Gln  Lys
               185                 190                           195

Ile  Leu  Cys  Ile  Glu  Lys  Cys  Phe  Thr  Phe  Thr  Ala  Ser  Phe  Asn
               200                 205                           210

Arg  Pro  Asn  Leu  Tyr  Tyr  Glu  Val  Arg  Gln  Lys  Pro  Ser  Asn  Thr
               215                 220                           225

Glu  Asp  Phe  Ile  Glu  Asp  Ile  Val  Lys  Leu  Ile  Asn  Gly  Arg  Tyr
               230                 235                           240

Lys  Gly  Gln  Ser  Gly  Ile  Ile  Tyr  Cys  Phe  Ser  Gln  Lys  Asp  Ser
               245                 250                           255

Glu  Gln  Val  Thr  Val  Ser  Leu  Gln  Asn  Leu  Gly  Ile  His  Ala  Gly
               260                 265                           270

Ala  Tyr  His  Ala  Asn  Leu  Glu  Pro  Glu  Asp  Lys  Thr  Thr  Val  His
               275                 280                           285

Arg  Lys  Trp  Ser  Ala  Asn  Glu  Ile  Gln  Val  Val  Val  Ala  Thr  Val
               290                 295                           300

Ala  Phe  Gly  Met  Gly  Ile  Asp  Lys  Pro  Asp  Val  Arg  Phe  Val  Ile
               305                 310                           315

His  His  Ser  Met  Ser  Lys  Ser  Met  Glu  Asn  Tyr  Tyr  Gln  Glu  Ser
               320                 325                           330

Gly  Arg  Ala  Gly  Arg  Asp  Asp  Met  Lys  Ala  Asp  Cys  Ile  Leu  Tyr
               335                 340                           345

Tyr  Gly  Phe  Gly  Asp  Ile  Phe  Arg  Ile  Ser  Ser  Met  Val  Val  Met
               350                 355                           360

Glu  Asn  Val  Gly  Gln  Gln  Lys  Leu  Tyr  Glu  Met  Val  Ser  Tyr  Cys
               365                 370                           375

Gln  Asn  Ile  Ser  Lys  Ser  Arg  Arg  Val  Leu  Met
               380                 385
```

( 2 ) INFORMATION FOR SEQ ID NO:76:

( i ) SEQUENCE CHARACTERISTICS:
        ( A ) LENGTH: 393
        ( B ) TYPE: AMINO ACID
        ( C ) STRANDEDNESS: SINGLE
        ( D ) TOPOLOGY: LINEAR ( i i ) MOLECULE TYPE:
        ( A ) DESCRIPTION: OTHER NUCLEIC ACID ( i i i ) HYPOTHETICAL: YES ( i v ) ANTI-SENSE: NO ( i x ) FEATURE:
        ( A ) NAME/KEY:
        ( B ) LOCATION:

( C ) IDENTIFICATION METHOD:
( D ) OTHER INFORMATION:

( x i ) SEQUENCE DESCRIPTION: SEQ ID NO: 76:

| Tyr | Pro | Trp | Ser | Asp | Glu | Val | Leu | Tyr | Arg | Leu | His | Glu | Val | Phe |
|---|---|---|---|---|---|---|---|---|---|---|---|---|---|---|
| 1 | | | | 5 | | | | | 10 | | | | | 15 |
| Lys | Leu | Pro | Gly | Phe | Arg | Pro | Asn | Gln | Leu | Glu | Ala | Val | Asn | Ala |
| | | | | 20 | | | | | 25 | | | | | 30 |
| Thr | Leu | Gln | Gly | Lys | Asp | Val | Phe | Val | Leu | Met | Pro | Thr | Gly | Gly |
| | | | | 35 | | | | | 40 | | | | | 45 |
| Gly | Lys | Ser | Leu | Cys | Tyr | Gln | Leu | Pro | Ala | Val | Val | Lys | Ser | Gly |
| | | | | 50 | | | | | 55 | | | | | 60 |
| Lys | Thr | His | Gly | Thr | Thr | Ile | Val | Ile | Ser | Pro | Leu | Ile | Ser | Leu |
| | | | | 65 | | | | | 70 | | | | | 75 |
| Met | Gln | Asp | Gln | Val | Glu | His | Leu | Leu | Asn | Lys | Asn | Ile | Lys | Ala |
| | | | | 80 | | | | | 85 | | | | | 90 |
| Ser | Met | Phe | Ser | Ser | Arg | Gly | Thr | Ala | Glu | Gln | Arg | Arg | Gln | Thr |
| | | | | 95 | | | | | 100 | | | | | 105 |
| Phe | Asn | Leu | Phe | Ile | Asn | Gly | Leu | Leu | Asp | Leu | Val | Tyr | Ile | Ser |
| | | | | 110 | | | | | 115 | | | | | 120 |
| Pro | Glu | Met | Ile | Ser | Ala | Ser | Glu | Gln | Cys | Lys | Arg | Ala | Ile | Ser |
| | | | | 125 | | | | | 130 | | | | | 135 |
| Arg | Leu | Tyr | Ala | Asp | Gly | Lys | Leu | Ala | Arg | Ile | Val | Val | Asp | Glu |
| | | | | 140 | | | | | 145 | | | | | 150 |
| Ala | His | Cys | Val | Ser | Asn | Trp | Gly | His | Asp | Phe | Arg | Pro | Asp | Tyr |
| | | | | 155 | | | | | 160 | | | | | 165 |
| Lys | Glu | Leu | Lys | Phe | Phe | Lys | Arg | Glu | Tyr | Pro | Asp | Ile | Pro | Met |
| | | | | 170 | | | | | 175 | | | | | 180 |
| Ile | Ala | Leu | Thr | Ala | Thr | Ala | Ser | Glu | Gln | Val | Arg | Met | Asp | Ile |
| | | | | 185 | | | | | 190 | | | | | 195 |
| Ile | His | Asn | Leu | Glu | Leu | Lys | Glu | Pro | Val | Phe | Leu | Lys | Gln | Ser |
| | | | | 200 | | | | | 205 | | | | | 210 |
| Phe | Asn | Arg | Thr | Asn | Leu | Tyr | Tyr | Glu | Val | Asn | Lys | Lys | Thr | Lys |
| | | | | 215 | | | | | 220 | | | | | 225 |
| Asn | Thr | Ile | Phe | Glu | Ile | Cys | Asp | Ala | Val | Lys | Ser | Arg | Phe | Lys |
| | | | | 230 | | | | | 235 | | | | | 240 |
| Asn | Gln | Thr | Gly | Ile | Ile | Tyr | Cys | His | Ser | Lys | Lys | Ser | Cys | Glu |
| | | | | 245 | | | | | 250 | | | | | 255 |
| Gln | Thr | Ser | Ala | Gln | Met | Gln | Arg | Asn | Gly | Ile | Lys | Cys | Ala | Tyr |
| | | | | 260 | | | | | 265 | | | | | 270 |
| Tyr | His | Ala | Gly | Met | Glu | Pro | Asp | Glu | Arg | Leu | Ser | Val | Gln | Lys |
| | | | | 275 | | | | | 280 | | | | | 285 |
| Ala | Trp | Gln | Ala | Asp | Glu | Ile | Gln | Val | Ile | Cys | Ala | Thr | Val | Ala |
| | | | | 290 | | | | | 295 | | | | | 300 |
| Phe | Gly | Met | Gly | Ile | Asp | Lys | Pro | Asp | Val | Arg | Phe | Val | Tyr | His |
| | | | | 305 | | | | | 310 | | | | | 315 |
| Phe | Thr | Val | Pro | Arg | Thr | Leu | Glu | Gly | Tyr | Tyr | Gln | Glu | Thr | Gly |
| | | | | 320 | | | | | 325 | | | | | 330 |
| Arg | Ala | Gly | Arg | Asp | Gly | Asp | Tyr | Ser | Tyr | Cys | Ile | Thr | Tyr | Phe |
| | | | | 335 | | | | | 340 | | | | | 345 |
| Ser | Phe | Arg | Asp | Ile | Arg | Thr | Met | Gln | Thr | Met | Ile | Gln | Lys | Asp |
| | | | | 350 | | | | | 355 | | | | | 360 |
| Lys | Asn | Leu | Asp | Arg | Glu | Asn | Lys | Glu | Lys | His | Leu | Asn | Lys | Leu |
| | | | | 365 | | | | | 370 | | | | | 375 |

```
Gln  Gln  Val  Met  Ala  Tyr  Cys  Asp  Asn  Val  Thr  Asp  Cys  Arg  Arg
               380                    385                         390

Lys  Leu  Val
```

( 2 ) INFORMATION FOR SEQ ID NO:77:

( i ) SEQUENCE CHARACTERISTICS:
        ( A ) LENGTH: 370
        ( B ) TYPE: AMINO ACID
        ( C ) STRANDEDNESS: SINGLE
        ( D ) TOPOLOGY: LINEAR ( i i ) MOLECULE TYPE:
        ( A ) DESCRIPTION: OTHER NUCLEIC ACID ( i i i ) HYPOTHETICAL: YES ( i v ) ANTI-SENSE: NO ( i x ) FEATURE:
        ( A ) NAME/KEY:
        ( B ) LOCATION:
        ( C ) IDENTIFICATION METHOD:
        ( D ) OTHER INFORMATION:

( x i ) SEQUENCE DESCRIPTION: SEQ ID NO: 77:

```
Val  Leu  Gln  Glu  Thr  Phe  Gly  Tyr  Gln  Gln  Phe  Arg  Pro  Gly  Gln
 1                  5                    10                         15

Glu  Glu  Ile  Ile  Asp  Thr  Val  Leu  Ser  Gly  Arg  Asp  Cys  Leu  Val
                    20                   25                         30

Val  Met  Pro  Thr  Gly  Gly  Gly  Lys  Ser  Leu  Cys  Tyr  Gln  Ile  Pro
                    35                   40                         45

Ala  Leu  Leu  Leu  Asn  Gly  Leu  Thr  Val  Val  Ser  Pro  Leu  Ile
                    50                   55                         60

Ser  Leu  Met  Lys  Asp  Gln  Val  Asp  Gln  Leu  Gln  Ala  Asn  Gly  Val
                    65                   70                         75

Ala  Ala  Ala  Cys  Leu  Asn  Ser  Thr  Gln  Thr  Arg  Glu  Gln  Gln  Leu
                    80                   85                         90

Glu  Val  Met  Thr  Gly  Cys  Arg  Thr  Gly  Gln  Ile  Arg  Leu  Leu  Tyr
                    95                   100                        105

Ile  Ala  Pro  Glu  Arg  Leu  Met  Leu  Asp  Asn  Phe  Leu  Glu  His  Leu
                    110                  115                        120

Ala  His  Trp  Asn  Pro  Val  Leu  Leu  Ala  Val  Asp  Glu  Ala  His  Cys
                    125                  130                        135

Ile  Ser  Gln  Trp  Gly  His  Asp  Phe  Arg  Pro  Glu  Tyr  Ala  Ala  Leu
                    140                  145                        150

Gly  Gln  Leu  Arg  Gln  Arg  Phe  Pro  Thr  Leu  Pro  Phe  Met  Ala  Leu
                    155                  160                        165

Thr  Ala  Thr  Ala  Asp  Asp  Thr  Thr  Arg  Gln  Asp  Ile  Val  Arg  Leu
                    170                  175                        180

Leu  Gly  Leu  Asn  Asp  Pro  Leu  Ile  Gln  Ile  Ser  Ser  Phe  Asp  Arg
                    185                  190                        195

Pro  Asn  Ile  Arg  Tyr  Met  Leu  Met  Glu  Lys  Phe  Lys  Pro  Leu  Asp
                    200                  205                        210

Gln  Leu  Met  Arg  Tyr  Val  Gln  Glu  Gln  Arg  Gly  Lys  Ser  Gly  Ile
                    215                  220                        225

Ile  Tyr  Cys  Asn  Ser  Arg  Ala  Lys  Val  Glu  Asp  Thr  Ala  Ala  Ala
                    230                  235                        240

Leu  Gln  Ser  Lys  Gly  Ile  Ser  Ala  Ala  Ala  Tyr  His  Ala  Gly  Leu
                    245                  250                        255
```

| Glu | Asn | Asn | Val | Arg<br>260 | Ala | Asp | Val | Gln | Glu<br>265 | Lys | Phe | Gln | Arg | Asp<br>270 |
|---|---|---|---|---|---|---|---|---|---|---|---|---|---|---|
| Asp | Leu | Gln | Ile | Val<br>275 | Val | Ala | Thr | Val | Ala<br>280 | Phe | Gly | Met | Gly | Ile<br>285 |
| Asn | Lys | Pro | Asn | Val<br>290 | Arg | Phe | Val | Val | His<br>295 | Phe | Asp | Ile | Pro | Arg<br>300 |
| Asn | Ile | Glu | Ser | Tyr<br>305 | Tyr | Gln | Glu | Thr | Gly<br>310 | Arg | Ala | Gly | Arg | Asp<br>315 |
| Gly | Leu | Pro | Ala | Glu<br>320 | Ala | Met | Leu | Phe | Tyr<br>325 | Asp | Pro | Ala | Asp | Met<br>330 |
| Ala | Trp | Leu | Arg | Arg<br>335 | Cys | Leu | Glu | Glu | Lys<br>340 | Pro | Gln | Gly | Gln | Leu<br>345 |
| Gln | Asp | Ile | Glu | Arg<br>350 | His | Lys | Leu | Asn | Ala<br>355 | Met | Gly | Ala | Phe | Ala<br>360 |
| Glu | Ala | Gln | Thr | Cys<br>365 | Arg | Arg | Leu | Val | Leu<br>370 | | | | | |

(2) INFORMATION FOR SEQ ID NO:78:

(i) SEQUENCE CHARACTERISTICS:
        (A) LENGTH: 1417
        (B) TYPE: AMINO ACID
        (C) STRANDEDNESS: SINGLE
        (D) TOPOLOGY: LINEAR (ii) MOLECULE TYPE:
        (A) DESCRIPTION: OTHER NUCLEIC ACID (iii) HYPOTHETICAL: YES (iv) ANTI-SENSE: NO (ix) FEATURE:
        (A) NAME/KEY:
        (B) LOCATION:
        (C) IDENTIFICATION METHOD:
        (D) OTHER INFORMATION:

(xi) SEQUENCE DESCRIPTION: SEQ ID NO: 78:

| | | | | Met<br>1 | Ala | Ala | Val | Pro<br>5 | Gln | Asn | Asn | Leu | Gln<br>10 | Glu | Gln |
|---|---|---|---|---|---|---|---|---|---|---|---|---|---|---|---|
| Leu | Glu | Arg<br>15 | His | Ser | Ala | Arg | Thr<br>20 | Leu | Asn | Asn | Lys | Leu<br>25 | Ser | Leu | Ser |
| Lys | Pro<br>30 | Lys | Phe | Ser | Gly | Phe<br>35 | Thr | Phe | Lys | Lys | Lys<br>40 | Thr | Ser | Ser | Asp |
| Asn<br>45 | Asn | Val | Ser | Val | Thr<br>50 | Asn | Val | Ser | Val | Ala<br>55 | Lys | Thr | Pro | Val | Leu<br>60 |
| Arg | Asn | Lys | Asp | Val<br>65 | Asn | Val | Thr | Glu | Asp<br>70 | Phe | Ser | Phe | Ser | Glu<br>75 | Pro |
| Leu | Pro | Asn | Thr<br>80 | Thr | Asn | Gln | Gln | Arg<br>85 | Val | Lys | Asp | Phe | Phe<br>90 | Lys | Asn |
| Ala | Pro | Ala<br>95 | Gly | Gln | Glu | Thr | Gln<br>100 | Arg | Gly | Gly | Ser | Lys<br>105 | Ser | Leu | Leu |
| Pro | Asp<br>110 | Phe | Leu | Gln | Thr | Pro<br>115 | Lys | Glu | Val | Val | Cys<br>120 | Thr | Thr | Gln | Asn |
| Thr<br>125 | Pro | Thr | Val | Lys | Lys<br>130 | Ser | Arg | Asp | Thr | Ala<br>135 | Leu | Lys | Lys | Leu | Glu<br>140 |
| Phe | Ser | Ser | Ser | Pro<br>145 | Asp | Ser | Leu | Ser | Thr<br>150 | Ile | Asn | Asp | Trp | Asp<br>155 | Asp |
| Met | Asp | Asp | Phe<br>160 | Asp | Thr | Ser | Glu | Thr<br>165 | Ser | Lys | Ser | Phe | Val<br>170 | Thr | Pro |

```
Pro  Gln  Ser  His  Phe  Val  Arg  Val  Ser  Thr  Ala  Gln  Lys  Ser  Lys  Lys
          175                      180                    185

Gly  Lys  Arg  Asn  Phe  Phe  Lys  Ala  Gln  Leu  Tyr  Thr  Thr  Asn  Thr  Val
     190                 195                      200

Lys  Thr  Asp  Leu  Pro  Pro  Pro  Ser  Ser  Glu  Ser  Glu  Gln  Ile  Asp  Leu
205                      210                    215                           220

Thr  Glu  Glu  Gln  Lys  Asp  Asp  Ser  Glu  Trp  Leu  Ser  Ser  Asp  Val  Ile
               225                      230                              235

Cys  Ile  Asp  Asp  Gly  Pro  Ile  Ala  Glu  Val  His  Ile  Asn  Glu  Asp  Ala
               240                 245                         250

Gln  Glu  Ser  Asp  Ser  Leu  Lys  Thr  His  Leu  Glu  Asp  Glu  Arg  Asp  Asn
          255                      260                    265

Ser  Glu  Lys  Lys  Lys  Asn  Leu  Glu  Glu  Ala  Glu  Leu  His  Ser  Thr  Glu
     270                 275                      280

Lys  Val  Pro  Cys  Ile  Glu  Phe  Asp  Asp  Asp  Tyr  Asp  Thr  Asp  Phe
285                      290                    295                      300

Val  Pro  Pro  Ser  Pro  Glu  Glu  Ile  Ile  Ser  Ala  Ser  Ser  Ser  Ser  Ser
                    305                      310                    315

Lys  Cys  Leu  Ser  Thr  Leu  Lys  Asp  Leu  Asp  Thr  Ser  Asp  Arg  Lys  Glu
               320                      325                    330

Asp  Val  Leu  Ser  Thr  Ser  Lys  Asp  Leu  Leu  Ser  Lys  Pro  Glu  Lys  Met
          335                      340                    345

Ser  Met  Gln  Glu  Leu  Asn  Pro  Glu  Thr  Ser  Thr  Asp  Cys  Asp  Ala  Arg
     350                      355                    360

Gln  Ile  Ser  Leu  Gln  Gln  Leu  Ile  His  Val  Met  Glu  His  Ile  Cys
365                      370                    375                      380

Lys  Leu  Ile  Asp  Thr  Ile  Pro  Asp  Asp  Lys  Leu  Lys  Leu  Leu  Asp  Cys
                    385                      390                         395

Gly  Asn  Glu  Leu  Leu  Gln  Gln  Arg  Asn  Ile  Arg  Arg  Lys  Leu  Leu  Thr
               400                      405                    410

Glu  Val  Asp  Phe  Asn  Lys  Ser  Asp  Ala  Ser  Leu  Leu  Gly  Ser  Leu  Trp
          415                      420                    425

Arg  Tyr  Arg  Pro  Asp  Ser  Leu  Asp  Gly  Pro  Met  Glu  Gly  Asp  Ser  Cys
     430                      435                    440

Pro  Thr  Gly  Asn  Ser  Met  Lys  Glu  Leu  Asn  Phe  Ser  His  Leu  Pro  Ser
445                      450                    455                           460

Asn  Ser  Val  Ser  Pro  Gly  Asp  Cys  Leu  Leu  Thr  Thr  Thr  Leu  Gly  Lys
                    465                      470                         475

Thr  Gly  Phe  Ser  Ala  Thr  Arg  Lys  Asn  Leu  Phe  Glu  Arg  Pro  Leu  Phe
               480                      485                    490

Asn  Thr  His  Leu  Gln  Lys  Ser  Phe  Val  Ser  Ser  Asn  Trp  Ala  Glu  Thr
          495                      500                    505

Pro  Arg  Leu  Gly  Lys  Lys  Asn  Glu  Ser  Ser  Tyr  Phe  Pro  Gly  Asn  Val
     510                      515                    520

Leu  Thr  Ser  Thr  Ala  Val  Lys  Asp  Gln  Asn  Lys  His  Thr  Ala  Ser  Ile
525                      530                    535                           540

Asn  Asp  Leu  Glu  Arg  Glu  Thr  Gln  Pro  Ser  Tyr  Asp  Ile  Asp  Asn  Phe
               545                      550                         555

Asp  Ile  Asp  Asp  Phe  Asp  Asp  Asp  Asp  Trp  Glu  Asp  Ile  Met  His
          560                      565                    570

Asn  Leu  Ala  Ala  Ser  Lys  Ser  Ser  Thr  Ala  Ala  Tyr  Gln  Pro  Ile  Lys
          575                      580                    585
```

```
Glu  Gly  Arg  Pro  Ile  Lys  Ser  Val  Ser  Glu  Arg  Leu  Ser  Ser  Ala  Lys
     590                 595                 600

Thr  Asp  Cys  Leu  Pro  Val  Ser  Ser  Thr  Ala  Gln  Asn  Ile  Asn  Phe  Ser
605                      610                 615                           620

Glu  Ser  Ile  Gln  Asn  Tyr  Thr  Asp  Lys  Ala  Gln  Asn  Leu  Ala  Ser
               625                 630                           635

Arg  Asn  Leu  Lys  His  Glu  Arg  Phe  Gln  Ser  Leu  Ser  Phe  Pro  His  Thr
               640                 645                           650

Lys  Glu  Met  Met  Lys  Ile  Phe  His  Lys  Lys  Phe  Gly  Leu  His  Asn  Phe
               655                 660                           665

Arg  Thr  Asn  Gln  Leu  Glu  Ala  Ile  Asn  Ala  Ala  Leu  Leu  Gly  Glu  Asp
     670                 675                      680

Cys  Phe  Ile  Leu  Met  Pro  Thr  Gly  Gly  Lys  Ser  Leu  Cys  Tyr  Gln
685                      690                 695                      700

Leu  Pro  Ala  Cys  Val  Ser  Pro  Gly  Val  Thr  Val  Val  Ile  Ser  Pro  Leu
               705                 710                           715

Arg  Ser  Leu  Ile  Val  Asp  Gln  Val  Gln  Lys  Leu  Thr  Ser  Leu  Asp  Ile
               720                 725                           730

Pro  Ala  Thr  Tyr  Leu  Thr  Gly  Asp  Lys  Thr  Asp  Ser  Glu  Ala  Thr  Asn
          735                 740                 745

Ile  Tyr  Leu  Gln  Leu  Ser  Lys  Lys  Asp  Pro  Ile  Ile  Lys  Leu  Leu  Tyr
750                      755                 760

Val  Thr  Pro  Glu  Lys  Ile  Cys  Ala  Ser  Asn  Arg  Leu  Ile  Ser  Thr  Leu
765                      770                 775                           780

Glu  Asn  Leu  Tyr  Glu  Arg  Lys  Leu  Leu  Ala  Arg  Phe  Val  Ile  Asp  Glu
               785                 790                           795

Ala  His  Cys  Val  Ser  Gln  Trp  Gly  His  Asp  Phe  Arg  Gln  Asp  Tyr  Lys
               800                 805                           810

Arg  Met  Asn  Met  Leu  Arg  Gln  Lys  Phe  Pro  Ser  Val  Pro  Val  Met  Ala
          815                 820                 825

Leu  Thr  Ala  Thr  Ala  Asn  Pro  Arg  Val  Gln  Lys  Asp  Ile  Leu  Thr  Gln
     830                 835                 840

Leu  Lys  Ile  Leu  Arg  Pro  Gln  Val  Phe  Ser  Met  Ser  Phe  Asn  Arg  His
845                      850                 855                           860

Asn  Leu  Lys  Tyr  Tyr  Val  Leu  Pro  Lys  Lys  Pro  Lys  Lys  Val  Ala  Phe
                    865                 870                      875

Asp  Cys  Leu  Glu  Trp  Ile  Arg  Lys  His  His  Pro  Tyr  Asp  Ser  Gly  Ile
               880                 885                           890

Ile  Tyr  Cys  Leu  Ser  Arg  Arg  Glu  Cys  Asp  Thr  Met  Ala  Asp  Thr  Leu
          895                 900                 905

Gln  Arg  Asp  Gly  Leu  Ala  Ala  Leu  Ala  Tyr  His  Ala  Gly  Leu  Ser  Asp
     910                 915                 920

Ser  Ala  Arg  Asp  Glu  Val  Gln  Gln  Lys  Trp  Ile  Asn  Gln  Asp  Gly  Cys
925                      930                 935                           940

Gln  Val  Ile  Cys  Ala  Thr  Ile  Ala  Phe  Gly  Met  Gly  Ile  Asp  Lys  Pro
                    945                 950                      955

Asp  Val  Arg  Phe  Val  Ile  His  Ala  Ser  Leu  Pro  Lys  Ser  Val  Glu  Gly
               960                 965                           970

Tyr  Tyr  Gln  Glu  Ser  Gly  Arg  Ala  Gly  Arg  Asp  Gly  Glu  Ile  Ser  His
          975                 980                 985

Cys  Leu  Leu  Phe  Tyr  Thr  Tyr  His  Asp  Val  Thr  Arg  Leu  Lys  Arg  Leu
     990                 995                 1000

Ile  Met  Met  Glu  Lys  Asp  Gly  Asn  His  His  Thr  Arg  Glu  Thr  His  Phe
1005                     1010                1015                          1020
```

```
Asn Asn Leu Tyr Ser Met Val His Tyr Cys Glu Asn Ile Thr Glu Cys
                1025                1030                1035

Arg Arg Ile Gln Leu Leu Ala Tyr Phe Gly Glu Asn Gly Phe Asn Pro
                1040                1045                1050

Asp Phe Cys Lys Lys His Pro Asp Val Ser Cys Asp Asn Cys Cys Lys
                1055                1060                1065

Thr Lys Asp Tyr Lys Thr Arg Asp Val Thr Asp Asp Val Lys Ser Ile
                1070                1075                1080

Val Arg Phe Val Gln Glu His Ser Ser Gln Gly Met Arg Asn Ile
1085                1090                1095                1100

Lys His Val Gly Pro Ser Gly Arg Phe Thr Met Asn Met Leu Val Asp
                1105                1110                1115

Ile Phe Leu Gly Ser Lys Ser Ala Lys Ile Gln Ser Gly Ile Phe Gly
                1120                1125                1130

Lys Gly Ser Ala Tyr Ser Arg His Asn Ala Glu Arg Leu Phe Lys Lys
                1135                1140                1145

Leu Ile Leu Asp Lys Ile Leu Asp Glu Asp Leu Tyr Ile Asn Ala Asn
                1150                1155                1160

Asp Gln Ala Ile Ala Tyr Val Met Leu Gly Asn Lys Ala Gln Thr Val
1165                1170                1175                1180

Leu Asn Gly Asn Leu Lys Val Asp Phe Met Glu Thr Glu Asn Ser Ser
                1185                1190                1195

Ser Val Lys Lys Gln Lys Ala Leu Val Ala Lys Val Ser Gln Arg Glu
                1200                1205                1210

Glu Met Val Lys Lys Cys Leu Gly Glu Leu Thr Glu Val Cys Lys Ser
                1215                1220                1225

Leu Gly Lys Val Phe Gly Val His Tyr Phe Asn Ile Phe Asn Thr Val
                1230                1235                1240

Thr Leu Lys Lys Leu Ala Glu Ser Leu Ser Ser Asp Phe Glu Val Leu
1245                1250                1255                1260

Leu Gln Ile Asp Gly Val Thr Glu Asp Lys Leu Glu Lys Tyr Gly Ala
                1265                1270                1275

Glu Val Ile Ser Val Leu Gln Lys Tyr Ser Glu Trp Thr Ser Pro Ala
                1280                1285                1290

Glu Asp Ser Ser Pro Gly Ile Ser Leu Ser Ser Ser Arg Gly Pro Gly
                1295                1300                1305

Arg Ser Ala Ala Glu Glu Leu Asp Glu Glu Ile Pro Val Ser Ser His
                1310                1315                1320

Tyr Phe Ala Ser Lys Thr Arg Asn Glu Arg Lys Arg Lys Lys Met Pro
1325                1330                1335                1340

Ala Ser Gln Arg Ser Lys Arg Arg Lys Thr Ala Ser Ser Gly Ser Lys
                1345                1350                1355

Ala Lys Gly Gly Ser Ala Thr Cys Arg Lys Ile Ser Ser Lys Thr Lys
                1360                1365                1370

Ser Ser Ser Ile Ile Gly Ser Ser Ser Ala Ser His Thr Ser Gln Ala
                1375                1380                1385

Thr Ser Gly Ala Asn Ser Lys Leu Gly Ile Met Ala Pro Pro Lys Pro
                1390                1395                1400

Ile Asn Arg Pro Phe Leu Lys Pro Ser Tyr Ala Phe Ser
1405                1410                1415
```

NUCLEIC ACIDS OF THE BLOOM'S SYNDROME GENE

STATEMENT OF GOVERNMENT INTEREST

This invention was made with government support under NIH Grant Nos. HD 04134, CA 50897 and GM 47890. As such, the government has certain rights in this invention.

BACKGROUND OF THE INVENTION

This invention is based upon the discovery by the inventors of the gene associated with Bloom's syndrome ("BS"), the "BLM gene" or "BLM", and a novel protein encoded by this gene. The discovery of the BLM gene and the protein encoded by the gene will have important implications in the diagnosis and treatment of BS, the recognition of carriers of mutations at BLM, and more broadly in the development of new cancer diagnostics and therapeutics.

BS is a rare autosomal recessive trait characterized clinically by growth deficiency, a sun-sensitive telangiectatic erythema of the face, immunodeficiency, and male infertility (German, J. Medicine 72:393–406 (1993)). Somatic cells from persons with BS are characterized by a striking genomic instability, and display an increased frequency of chromosome abnormalities (breaks, gaps and rearrangements) and inter- and intramolecular exchanges, including sister-chromatid exchanges (Ray, J. H. and German, J. (1983) The cytogenetics of the "chromosome-breakage syndromes." In: German J. (ed.) Chromosome mutations and neoplasia. Alan R. Liss, New York, pp. 135–168). The hypermutability of BS cells is responsible for the benign and malignant neoplasms in BS patients that arise at unusually early ages and in excessive numbers (German, 1993, supra).

Complementation analyses have established that a single locus, designated BLM, is mutated in BS (Weksberg, R., et al. Am. J. Hum. Genet. 42:816–824 (1988)). The BLM locus has been assigned to human chromosome 15 (McDaniel, L. D., and Schultz, R. A. Proc. Natl. Acad. Sci. USA 89:7968–7972 (1992)), and regionally mapped to chromosome band 15q26.1 based upon tight linkage to FES by homozygosity mapping (German, J., et al. Proc. Acad. Natl. Sci. USA 91:6669–6673 (1994)). Prior to the present invention, however, the BLM gene had not been identified.

SUMMARY OF THE INVENTION

The present invention provides a method for diagnosing BS in a subject comprising detecting the presence of two mutated BLM genes or the absence of a wild type BLM gene in nucleic acid of the subject. The present invention also provides a method for determining whether a subject is a carrier of a mutated BLM gene comprising detecting the presence of a mutated BLM gene in nucleic acid of the subject.

The present invention further provides one or more single-stranded nucleic acid probes which specifically hybridize to the wild type BLM gene or the mutated BLM gene, and mixtures thereof, which may be formulated in kits, and used for diagnosing BS or determining whether a subject is a carrier of the mutated BLM gene.

In addition, the present invention provides an antibody immunoreactive with a wild type BLM protein, as well as an antibody immunoreactive with a mutant BLM protein, which may be formulated in kits, and used for diagnosing BS or determining whether a subject is a carrier of the mutated BLM gene.

The present invention also provides a method for treating or preventing the onset of BS in a subject in need of such treatment or prevention comprising the delivery and expression of a functional BLM gene into a sufficient number of cells of the subject to treat or prevent the onset of BS in the subject. A stem cell which expresses the BLM gene introduced therein through viral transduction, homologous recombination or transfection is also provided by the invention.

The present invention further provides a recombinant viral vector for treating a defect in the BLM gene in a target cell comprising (a) the nucleic acid of or corresponding to at least a portion of the genome of a virus, which portion is capable of directing the infection of the target cell, and (b) a BLM gene operably linked to the viral nucleic acid and capable of being expressed as a functional gene product in the target cell.

The present invention still further provides a purified and isolated nucleic acid encoding an enzymatically active BLM protein, a vector comprising this nucleic acid, a cell stably transformed with this vector, as well as a method for producing recombinant, enzymatically active BLM protein. A purified, enzymatically active BLM protein is also provided by the present invention.

Finally, the present invention provides a vector and an embryonic stem cell each of which comprises a mutated BLM gene, a non-human, transgenic animal whose germ and somatic cells contain a mutated BLM gene sequence introduced into said animal, or an ancestor thereof, at an embryonic stage, as well as a method for producing the non-human, transgenic animal.

Additional objects of the invention will be apparent from the description which follows.

of persons with BS as well as samples from their fathers (PF) and their mothers (PM). These persons are identified by their Bloom's Syndrome Registry designations (see German, J., and Passarge, E. *Clin. Genet.* 35:57–69 (1989)). Arrows point to DNA fragments amplified from the heterozygous alleles of the constitutional genotypes, pat (for paternal) and mat (for maternal). Asterisks mark alleles in the low-SCE LCLs that are lost through somatic crossing-over. Lines mark DNA fragments amplified from alleles of the parents but that were not transmitted to the offspring with BS. From one of the four persons with BS, 11 different clonal LCLs were examined; 3 of the 11 had undergone reduction to homozygosity at loci distal to BLM—as explained elsewhere ((Ellis, N. A., et al. Somatic intragenic recombination within the mutated locus BLM can correct the high-SCE phenotype of Bloom syndrome cells. *Am. J. Hum. Genet.,* 1995, in press). Autoradiographic patterns are shown from 2 of the 11 low-SCE LCLs from 11(IaTh), one representative of cell lines in which allele losses were detected ($p^1$ sample on right) and another of cell lines in which they were not ($p^1$ sample on left).

Figure 2A:
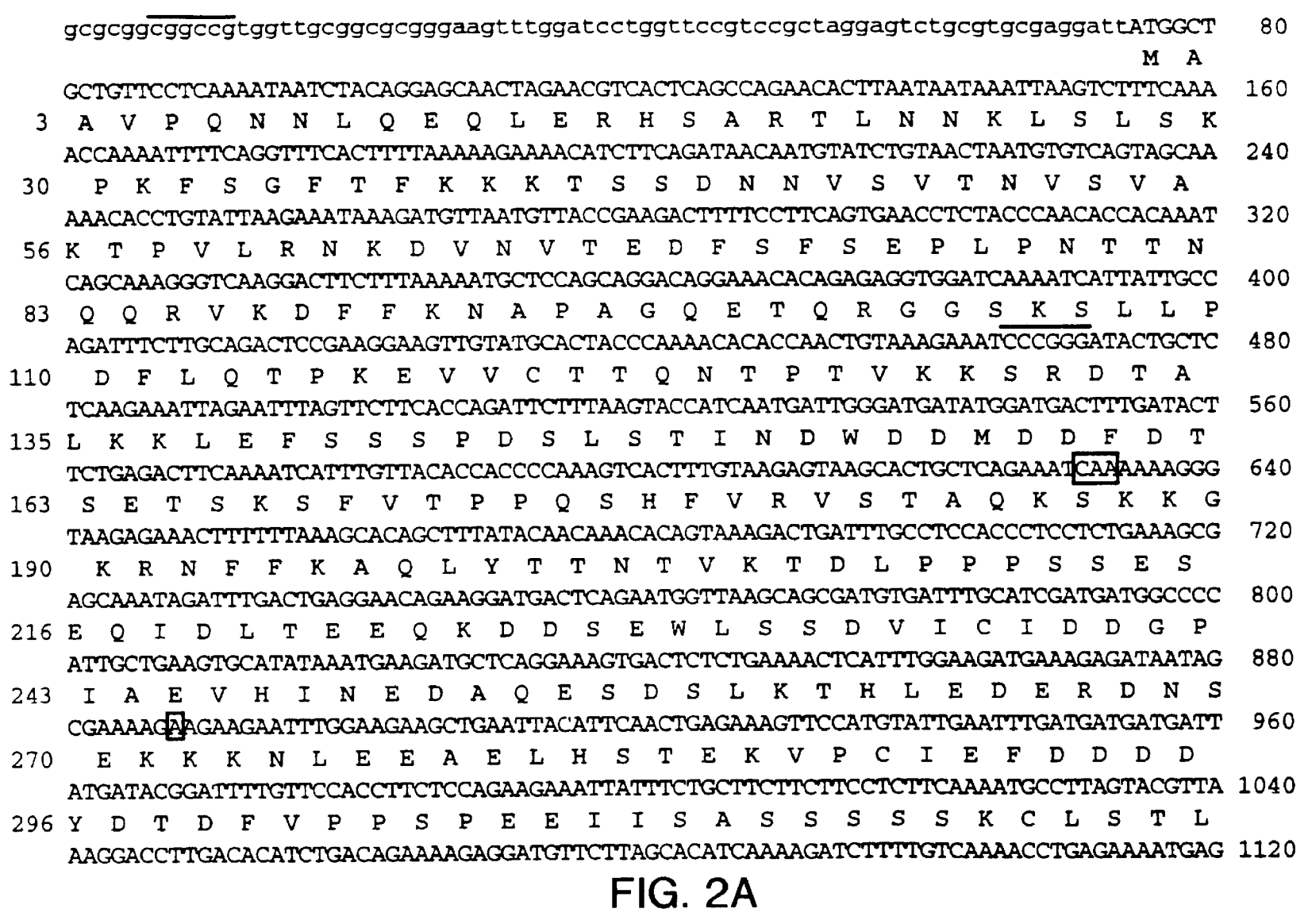

FIGS. 2A through 2D are depictive of the 4,437-bp H1-5' sequence (SEQ. ID. NO:76), which represents the merged sequences of the H1 cDNA and the 5' clones, with its encoded 1,417-residue amino acid sequence (SEQ. ID. NO:78)(single-letter code). Nucleotides in the open reading frame starting at the first in-frame ATG, 75 bp from the first nucleotide of the H1-5' sequence, are capitalized. The in-frame nonsense codon (TAA) marked by a period is followed by 88 nucleotides of 3' untranslated sequence. At the initiator methionine, there is a Kozak consensus sequence (Kozak, M. *J. Cell Biol.* 108:229–241 (1989)), and an acceptable polyadenylation sequence (underlined) is present 20-bp upstream of a 21-bp polyA tail. Sites at which substitution or deletion were detected in persons with BS (see Table 1) are boxed, and a site at which an insertion was identified is marked by a diamond. The EagI and SmaI sites used in the construction of a full-length cDNA referred to as B3 (see Experimental Details Section) are overlined. Asterisks mark amino acid identities to three motifs present in the RNA polymerase II largest subunit.

Figure 3:
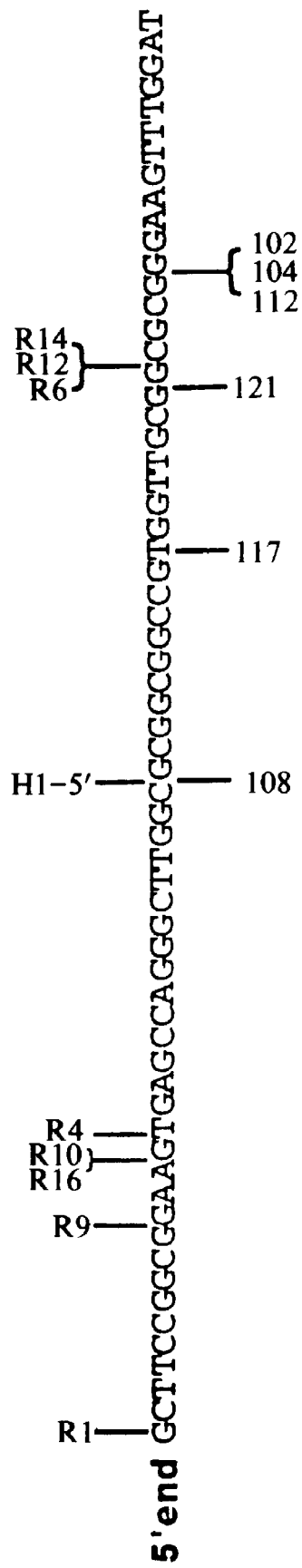

FIG. 3 is depictive of the nucleotide sequence of the 5' end of the candidate gene determined by cDNA analysis and 5'-RACE experiments. The sequence of the longest cDNA isolated (clone R1) is shown (SEQ ID NO:73). The sequences were obtained by analysis of 11 lymphoblastoid cDNAs (clone names prefixed by an R), identified by screening $8\times10^6$ clones with a EagI/SmaI DNA fragment from the 5' part of the H1-5' sequences (FIG. 2), and of 12 5'-RACE clones amplified from fibroblast cDNA with nested PCR primers (Experimental Details Section). Vertical lines mark the nucleotides at which nine lymphoblastoid cDNA (clones named above the sequences) and six cloned 5'-RACE fragments (clones named below the sequences) initiated. Three cDNA and six 5'-RACE clones not shown contained sequences which initiated less than 38 bp upstream of the first in-frame ATG. The sequences at the 5' end are G+C-rich (71%), perhaps explaining the absence of in-frame nonsense codons upstream of the first in-frame ATG.

FIG. 4 represents the amino acid sequence homologies in the seven conserved helicase domains between the putative peptide encoded by the H1-5' sequence (BLM sequence-SEQ. ID. NO:74) and by the three other known members of the RecQ subfamily of helicases (REQL sequence-SEQ.ID. NO:75; SGS1 sequence-SEQ. ID. NO:76; recQ sequence-SEQ. ID. NO:77). The numbers (left) indicate amino acid positions in each peptide, and gene product names are at the right. Sequence alignments were performed by the Megalign computer program (DNAStar); dashes indicate gaps inserted by the program to maintain alignment. Amino acid residues that are identical at a position between sequences are shaded. Two different shadings are used when at a position two pairs of identical amino acids were observed. Overlined sequences mark the seven helicase domains (Gorbalenya, A. E., et al. *Nucl. Acids Res.* 17:4713–4730 (1989)). The DExH box is in helicase domain II. Asterisks denote positions at which putative missense mutations were identified. The candidate gene product is referred to here as BLM because mutations have been discovered in the gene in persons with BS (see text).

Figure 5A:
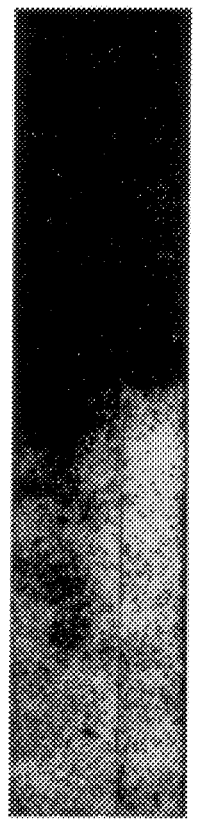
Figure 5B:
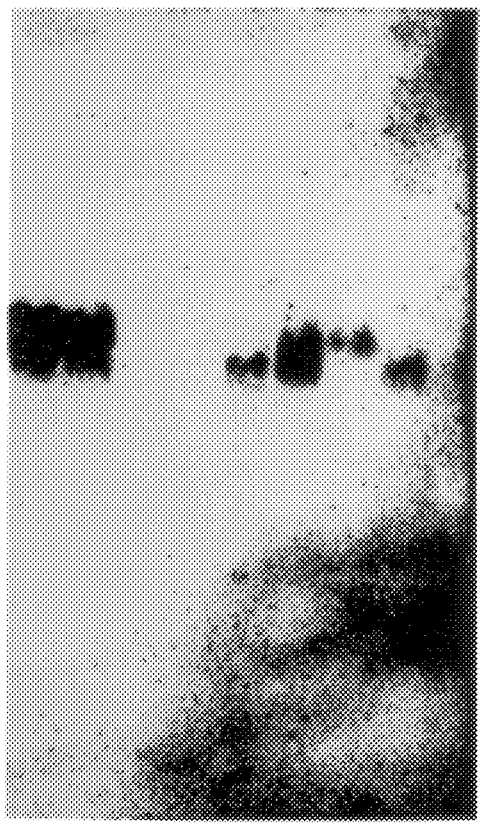
Figure 6A:
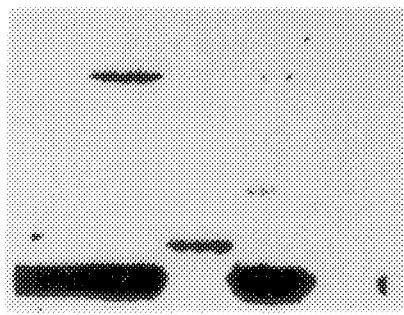
Figure 6B:
Figure 6C:
Figure 6D:
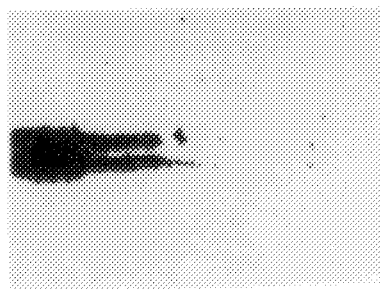
Figure 6E:
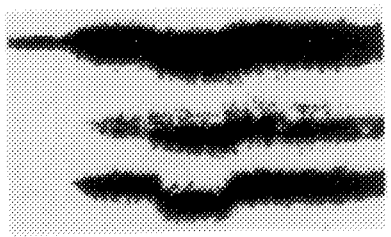

FIGS. 5A and 5B represent the Northern analysis of the H1-5' sequences expressed in cultured cells. In FIG. 5A, RNA preparations were analyzed from HG2162, a normal LCL; HG2635, a normal diploid fibroblast cell line; and HeLa cells. In FIG. 5B, RNA preparations were analyzed from HG 1943 and HG2162—normal LCLs—and HG2703, HG1584, HG1987, HG1972, HG2231, HG1626, HG2820—BS LCLs. Thirty micrograms of total RNA from each cell line was loaded in each lane. Labeled probes—the H1 cDNA (upper panels) and a cDNA for G3PDH (lower panels)—were hybridized to membranes of the blotted gels and, after washing, the membranes were exposed from one to three days (FIG. 5A) or for 15 minutes (FIG. 5B). On a 7-day exposure, faint bands resembling the hybridization pattern in normal cells were detected at the 4.5-kb position in HG2703, HG1584, and HG2820. The LCLs developed from persons with BS are shown in Table 1, except HG2703, [NR2 (CrSpe)]; and HG2820, [142(MaMatu)].

FIGS. 6A–6E represent the novel SSCP conformers detected in cDNA samples isolated from BS LCLs after PCR-amplification of the BLM gene. Each figure includes five lanes of cDNAs from five unrelated persons with BS amplified with oligonucleotides designed from a unique region of the BLM gene. The novel conformers in which mutations were detected are shown in the center lanes of each figure: 6A, BS LCL HG1514 from 15(MaRo); 6B, BS LCL HG1624 from 113(DaDem); 6C, BS LCL HG1926 from 97(AsOk); 6D, BS LCL HG2231 from 139(ViKre); 6E, BS LCL HG1626 from 93(YoYa). Not shown are novel conformers in 92(VaBi) and 112(NaSch).

DETAILED DESCRIPTION OF THE INVENTION

The present invention provides a method for diagnosing BS in a subject comprising detecting the presence of two mutated BLM genes or the absence of a wild type BLM gene in nucleic acid of the subject. The present invention also provides a method for determining whether a subject is a carrier of a mutated BLM gene comprising detecting the presence of a mutated BLM gene in nucleic acid of the subject.

As used herein, the "mutated BLM gene" is the mutated form of the normal BLM gene, which contains one or more deletion, insertion, point or rearrangement mutations, or a combination thereof, that may result in loss or alteration of activity of the gene product expressed by the mutated BLM gene. A subject who inherits a copy of the mutated BLM gene on each chromosome 15 has clinical BS. The "wild type BLM gene" is the normal form of the gene which expresses an enzymatically active gene product. The wild type BLM gene is present in subjects who are not carriers of the mutated BLM gene, and is the preferentially expressed gene in subjects who are carriers of the mutated BLM gene.

The methods of the present invention may be used to determine whether persons in the population at large are carriers of the mutated BLM gene or have BS, for identifying persons at risk in developing the disease, i.e. relatives of persons with BS, as well as for confirming diagnosis of BS. The methods of the present invention are also useful for identifying couples who are carriers of the mutated BLM gene and thus at risk for propagating offspring who will have BS, as well as for identifying embryos or fetuses which may be born with BS. Accordingly, as used herein, "subject" may be an embryo, fetus, newborn, infant or adult.

The presence of the mutated BLM gene(s) (or the absence of the wild type BLM gene) may be detected by procedures known in the art including but not limited to standard sequencing techniques (e.g. dideoxy chain termination), restriction enzyme digestion analysis, hybridization with one or more probes hybridizable to the mutated and/or wild type BLM gene using standard procedures such as Southern blot analysis, polymerase chain reaction using sense and antisense primers prepared from the mutated and/or wild type BLM genes, and combinations thereof.

The presence of the mutated BLM gene(s) (or the absence of the wild type BLM gene) also may be detected by detecting expression of the gene product of the gene. Such expression products include both mRNA as well as the protein product itself. mRNA expression may be detected by standard sequencing techniques, hybridization with one or more probes hybridizable to the mutated and/or wild type BLM mRNA using standard procedures such as Northern blot analysis, dot and slot hybridization, S1 nuclease assay, or ribonuclease protection assays, polymerase chain reaction using sense and antisense primers prepared from the mutated and/or wild type BLM genes, and combinations thereof. The protein may be detected using antibodies to the protein expressed by the mutated BLM gene and/or the wild type BLM gene by procedures known in the art including but not limited to immunoblotting, immunoprecipitation, solid phase radioimmunoassay (e.g. competition RIAs, immobilized antigen or antibody RIAs, or double antibody RIAs), enzyme-linked immunoabsorbent assay, and the like.

The present invention also provides single-stranded nucleic acid probes and mixtures thereof for use in diagnosing BS and/or determining whether an individual is a carrier of the mutated BLM gene. The nucleic acid probes may be DNA, cDNA, or RNA, and may be prepared from the mutated and/or wild type BLM gene. The probes may be the full length sequence of BLM gene, or fragments thereof. Typical probes are 12 to 40 nucleotides in length. Generally, the probes are complementary to the BLM gene coding sequences, although probes to introns are also contemplated. The probes may be synthesized using an oligonucleotide synthesizer such as Applied Biosystems Model 392 DNA/RNA synthesizer, and may be labeled with a detectable marker such as a fluorescence, enzyme or radiolabeled markers including $^{32}p$ and biotin, and the like. Combinations of two or more labelled probes corresponding to different regions of the BLM gene also may be included in kits to allow for the detection and/or analysis of the BLM gene by hybridization.

The present invention also provides antibodies immunoreactive with the protein expressed by the wild type BLM gene (and analogues thereof), as well as antibodies immunoreactive with the protein expressed by the mutated BLM gene. The antibodies may be polyclonal or monoclonal and are produced by standard techniques. The antibodies may be labeled with standard detectable markers (e.g. chemiluminescent detection systems and radioactive labels such as $^{125}I$) for detecting the wild type and mutated BLM genes. The antibodies also may be presented in kits with detectable labels and other reagents and buffers for such detection.

The present invention also provides a method for treating or preventing the onset of BS in a subject in need of such treatment or prevention comprising the delivery and expression of a functional BLM gene into a sufficient number of cells of the subject, preferably bone marrow stem cells, to treat or prevent the onset of BS in the subject. As used herein, "functional BLM gene" is a gene which when incorporated into a cell's nucleic acid expresses a functional gene product, and includes the wild type BLM gene as well as variations thereof. The delivery and expression of the functional BLM gene may be accomplished by introducing the functional BLM gene into the cells or by correcting the mutation(s) in the subject's BLM gene.

The functional BLM gene may be delivered into the subject's cells by a number of procedures known to one skilled in the art, e.g. electroporation, DEAE dextran, cationic liposome fusion (using both monocationic and polycationic lipids), protoplast fusion, DNA coated microprojectile bombardment, injection with recombinant replication-defective retroviruses, homologous recombination, and the like. Accordingly, a stem cell which expresses the BLM gene introduced therein through viral transduction, homologous recombination, or transfection is also provided by the present invention.

The present invention also provides a recombinant viral vector for treating a defect in the BLM gene in a target cell comprising (a) the nucleic acid of or corresponding to at least a portion of the genome of a virus, which portion is capable of directing the infection of the target cell, and (b) a functional BLM gene operably linked to the viral nucleic acid and capable of being expressed as a functional gene product in the target cell. The recombinant viral vectors of the present invention may be derived from a variety of viral nucleic acids known to one skilled in the art, e.g. the genomes of HSV, adenovirus, adeno-associated virus, Semiliki Forest virus, vaccinia virus, and other retroviruses or DNA viruses.

In addition, the present invention provides a purified and isolated nucleic acid encoding an enzymatically active BLM protein, which may be the wild type protein or an analogue thereof, and includes all nucleic acid sequences encoding such enzymatically active proteins, including substitutions due to the degeneracy of the genetic code. The nucleic acid may be genomic DNA, cDNA or RNA. In the preferred embodiment, the nucleic acid encodes the amino acid sequence contained in FIG. 2. In the particularly preferred embodiment, the nucleic acid has the nucleotide sequence contained in FIG. 2.

The present invention also provides a vector comprising nucleic acid encoding an enzymatically active BLM protein, as well as a cell stably transformed with the vector. The vector may be any plasmid, viral-derived nucleic acid, lytic bacteriophage derived from phage lambda, cosmid, filamentous single-stranded bacteriophage such as M13, and the like, for cloning nucleic acid or introducing the nucleic acid into a cell for expression. The cell may be eukaryotic or prokaryotic. Suitable host cells include but are not limited to bacterial cells such as *E. coli, Bacillus subtilis, Agrobacterium tumefaciens, Bacillus subtilis, Agrobacterium tumefaciens, Bacillus megaterium*, eukaryotic cells such as *Pichia pastoris, Chlamydomonas reinhardtii, Cryptococcus neoformans, Neurospora crassa, Podospora anserina, Saccharomyces cerevisiae, Saccharomyces pombe, Uncinula*

*necator*, cultured insect cells, cultured chicken fibroblasts, cultured hamster cells, cultured human cells such as HT1080, MCF7, 143B and cultured mouse cells such as EL4 and NIH3T3 cells. Such expression systems may be used to produce a recombinant, enzymatically active BLM protein by culturing a cell transformed with a vector comprising a nucleic acid encoding an enzymatically active BLM protein, and recovering BLM protein from the culture.

The present invention also provides a purified enzymatically active BLM protein. The protein may be the wild type protein or an analogue thereof. As used herein, "analogue" means functional variants of the wild type protein, and includes BLM proteins isolated from mammalian sources other than human, as well as functional variants thereof. The protein also may be isolated from native cells or recombinantly produced. Preferably, the protein has the amino acid sequence contained in FIG. 2.

The present invention also provides a vector for use in preparing a non-human, transgenic animal comprising a mutated BLM gene which is capable of introducing the mutated BLM gene in at least some embryonic cells to which the vector is introduced, an embryonic stem cell comprising a mutated BLM gene which has been integrated into the cell following transduction with the vector above, as well as a non-human transgenic animal of BS which would be useful for studying BS as well as cancer in general. The mutated BLM gene may be integrated into the germ line of a non-human animal such as a mouse, rat, goat, sheep or other non-human species in order to obtain a transgenic animal model by methods known in the art (see Alberts, B., et al. *Molecular Biology of the Cell*, 2d. Garland Publ. Inc., New York and London, pp. 267–269 (1989)). For example, nucleic acid encoding the mutated BLM protein can be inserted into the genome of a replication-defective virus such as HSV or a retrovirus or transposen and the resultant construct injected into embyronic stem cells. Alternatively, the transgenic animal may be made by injecting nucleic acid into the male pronucleus of a fertilized egg of a nonhuman animal, transplanting the "transgenic embryo" into a pseudopregnant female and then analyzing offspring for the presence of the injected nucleic acid in their genome.

Based upon the high incidence of a variety of tumors in a variety of tissues in a BS patient which appears to model cancer development in the general population (German, J. *Medicine* 72:393–406 (1993)), the identification of the BLM gene and its gene product should be useful for developing diagnostics and therapeutics for cancer in the population at large.

The present invention is described in the following Experimental Details Section, which is set forth to aid in an understanding of the invention, and should not be construed to limit in any way the invention as defined in the claims which follow thereafter.

Experimental Details Section

I. Materials and Methods

A. Subjects and Samples

The persons with BS in whom low-SCE lymphocytes have arisen were described previously (German, J., et al. Bloom's syndrome. XIX. Cytogenetic and population evidence for genetic heterogeneity. *Clin. Genet.*, 1995, in press). Epstein-Barr virus transformed lymphoblastoid cell lines (LCLs) were developed from these and other persons with BS by standard culture methods using material obtained through the Bloom's Syndrome Registry (German and Passarge, supra). The recombinant low-SCE LCLs in which reduction to homozygosity had been detected, and the cells used to determine the constitutional genotypes of the five persons from whom these recombinant low-SCE LCLs were developed, also have been described (Ellis, et al. *Am. J. Hum. Genet.*, 1995, supra). The polymorphic loci typed included some previously reported (Beckmann, J. S., et al. *Hum. Mol. Genet.* 2:2019–2030 (1993); Gyappay, G., et al. *Nature Genetics* 7:246–339 (1994)) and others that were identified during the physical mapping of the BLM region of chromosome 15 (Straughen, et al., supra). The methods of preparation of DNA samples, oligonucleotide primers, and conditions for PCR amplification of microsatellite polymorphisms on chromosome 15 have been described (German, et al., 1994, supra; Ellis, N. A., et al. *Am. J. Hum. Genet.* 55:453–460 (1994); Straughen, et al., supra).

B. Direct cDNA Selection

Direct cDNA selection was carried out as described by Parimoo, S., et al. (*Proc. Natl. Acad. Sci. USA* 88:9623–9627 (1991)). Briefly, DNAs (15 ng) from commercial lambda cDNA libraries prepared from cultured foreskin fibroblasts (Clontech) and Jurkat cells (Stratagene) were amplified by PCR (94° C. 1 min, 55° C. 1 min, 72° C. 2 min and 10 sec for 32 cycles) using primer set A (GGTGGCGACGACTCCTGGA (SEQ. ID. NO:1) and ACCAGACCAACTGGTAATG) (SEQ. ID. NO:2) for the fibroblast cDNA library and the universal forward and reverse M13 sequencing primers for the Jurkat cDNA library under standard conditions with Taq polymerase (Boehringer Mannheim). EcoRI-digested cosmid (c905) or P1 (P1958) DNAs (100 ng) bound to Hybond N membrane in 10×SSC, were denatured in 0.5M NaOH/1.5M NaCl, neutralized in 0.5N Tris-HCl pH 7.2/1.5M NaCl, and fixed by UV-crosslinking. Hybridization of the PCR-amplified cDNAs to repetitive sequences on the cosmid and P1 clones was blocked by prehybridizing the membranes with Cot1 DNA (25 ng/m; Gibco, BRL), poly(dI):poly(dC) (20 ng/$\mu$l; Pharmacia), vector DNA (pWE15 or pAD10SacBII at 25 ng/$\mu$l in 5×SSPE, 5×Denhardt's solution, and 0.5% SDS at 65° C. overnight. Hybridization of the PCR-amplified cDNAs (25 ng/$\mu$l) was at 65° C. for 2 days in the same solution without poly(dI):poly(dC). The membranes were washed, and without elution the bound cDNAs were amplified by PCR with primer set A, followed by nested PCR with primer set B (ATGGTAGCGACCGGCGCTCA (SEQ. ID. NO:3) and CCGTCAGTATCGGCGGAATT) (SEQ. ID. NO:4) for the fibroblast library and the T3 and T7 sequencing primers for the Jurkat library. A sample of the PCR product after each amplification was analyzed by agarose gel electrophoresis, and another was cloned into Bluescript. Independent clones were picked at random, plasmid DNAs prepared, and insert sizes were determined by restriction enzyme digestion and agarose gel electrophoresis. Inserts from selected clones were purified and used as hybridization probes against all of the other clones as well as against selected genomic DNAs to determine the chromosomal origin of the sequences (see below). The enrichment procedure was repeated and the selected cDNA clones analyzed again. The fibroblast cDNA clone 905-28 was obtained after two rounds of selection (250,000-fold enriched), and was sequenced by the dideoxy chain-termination technique (Sanger, F., et al. *Proc. Natl. Acad. Sci.* 74:55463–5467 (1977); Tabor, S., and Richardson, C. C. *Proc. Natl. Acad. Sci. USA* 84:4767–4771 (1987)).

The genomic origin of clones isolated by direct selection were verified by hybridization of inserts to Southern blots of DNAs from the following: clones in the contig; human cells; and two human×hamster somatic cell hybrids, one of which contains an intact chromosome 15 as the only human chromosome present (GS89K-1; Warburton, D., et al.

*Genomics* 6:358–366 (1990)) and one in which the only chromosome 15 material present had, through a translocation, lost all the sequences distal to band 15q25 (GM10664, obtained from NIGMS Human Genetic Mutant Cell Repository at the Cornell Institute of Medical Research).

C. cDNA Cloning, 5'-RACE, and cDNA Sequencing

The selected cDNA 905-28 was hybridized to $10^6$ clones from a HeLa cDNA library (Stratagene) according to standard procedures (Sambrook, J., Fritsch, E. F., and Maniatis, T. (1989) Molecular Cloning. A Laboratory Manual. 2nd edition, Cold Spring Harbor University Press). Twenty-eight lambda clones were isolated and converted to Bluescript plasmids by superinfection with ExAssist helper phage (Stratagene). DNA was prepared and 15 independent size-classes of clones were identified. The 5'-end of a clone from each class was sequenced with Bluescript SK sequencing primer. To extend the sequence, two oligonucleotides were synthesized from the beginning and the end of each of the 5' sequences, and sequencing was performed on the largest cDNA clone obtained by hybridization (clone H1). This procedure provided sequences from both DNA strands for most of the H1 cDNA. Ambiguous segments were determined by sequencing with specific oligonucleotides.

Because the reading frame was open at the 5' end of the H1 clone, additional upstream sequences were obtained by a PCR method. PCR was carried out on DNA prepared from the HeLa cDNA library using an oligonucleotide (Y177, TTGTGGTGTTGGGTAGAGGTT) (SEQ. ID. NO:5) 8 bp from the 5' end of H1 and the T3 sequencing primer. The PCR products were cloned into pT7Blue (Novagen), 18 clones were isolated, and the 8 largest inserts were sequenced. The three largest of these clones (5'-5, 5'-15, and 5'-17) extended the sequences 289 bp 5' of the H1 cDNA. The complete cDNA sequences present in the HeLa library are referred herein as H1-5' (FIG. 2). Database searches then were carried out according to the method of Altschul, S. F., et al. (*J. Mol. Biol.* 215:403–410 (1990)) using segments of the predicted amino acid sequence encoded in the HI-5' sequence as queries against the collected amino acid sequence databases that are accessible through the National Library of Medicine.

A full-length clone referred to as B3 was constructed by performing PCR of HeLa library DNA using an oligonucleotide (Y180, GCCGCCGGCACCAAC) (SEQ. ID. NO:6) from the 5' end of the H1-5' sequence and an internal oligonucleotide (BC13, CCTCAGTCAAATCTATITGCTC) (SEQ. ID. NO:7) which permitted amplification of a 739-bp product. EagI and SmaI sites (FIG. 2) were used to clone the product into NotI/SmaI-digested H1 DNA.

The 461-bp EagI/SmaI fragment of B3 was isolated and used to probe $8 \times 10^6$ clones of a pREP4-cloned unidirectional cDNA library from DEB-treated lymphoblastoid cells (Strathdee, C. A., et al. *Nature* 356:763–767 (1992)). Twelve cDNA clones were identified, and the 5' end of 11 were sequenced. Eight of them are apparently full-length cDNAs (FIG. 3). By restriction enzyme analysis, 1 of the 12 clones was shown to contain a deletion 3' of nucleotide 2897 and the insertion of about 250 bp there.

5'-RACE (rapid amplification of cDNA ends) was performed to characterize the 5' sequences of the candidate gene using a Clontech Marathon™ cDNA Amplification Kit according the manufacturers specifications. Briefly, first-strand synthesis was carried out with MMLV reverse transcriptase using polyT-primed RNAs prepared from cultured fibroblast, lymphoblastoid, and HeLa cells and polyA+ RNA from placenta (provided in the kit). Then, second-strand synthesis was performed with RNAseH, *E. coli* PoLI, and *E. coli* DNA ligase. The DNA ends were made blunt with T7 DNA polymerase, and adapters with overhanging ends were ligated to the cDNA. Nested PCRs then were carried out using 5' oligonucleotides from the adaptor (AP1 and AP2) and internal 3' oligonucleotides from the H1-5' sequence (BC5, GCCATCACCGGAACAGAAGGAAA (SEQ. ID. NO:8); and BC11, TCTTCTGGAGAAGGTGGAACAA) (SEQ. ID. NO:9). Bands derived from the H1-5' sequences were identified in all four of the cDNA samples. PCR products from the 5'-RACE-amplified fibroblast cDNA was cloned into Bluescript, and the 5' ends of 12 clones were sequenced (FIG. 3).

D. Northern Blot Analysis

RNAs were prepared from cultured cells using TRIzol reagent (Gibco, BRL) according to the manufacturer's instructions. Total RNAs (30 μg) were size-separated by electrophoresis through 6.3% formaldehyde 1.2% agarose gels in 0.02M MOPS, 0.05M sodium acetate pH 7.0, and 0.001M EDTA. The RNAs were transferred to Hybond-N (Amersham) in 20×SSPE and fixed to the membranes by UV-crosslinking. Hybridizations were performed as described (Ellis, N. A., et al. *Nature Genetics* 6:394–400 (1994)).

E. Single-Strand Conformation Polymorphism (SSCP) Analysis

After first-strand synthesis, PCR was carried out with 200 ng cDNA, 5.2 pmol of each oligonucleotide primer (Table 2), 3% DMSO, 0.2 mM dNTPs (Pharmacia), 1×reaction buffer from Boehringer Mannheim, 0.25 units of Taq polymerase (Boehringer Mannheim), and 1.0 μCi of α-[$^{32}$P]-dCTP in a total volume of 10 μl. Each reaction was overlaid with mineral oil and initially denatured for 5 min at 94° C. followed by 35 cycles of 94° C. for 1 min, 60° C. for 1 min, and 72° C. for 1 min. The last cycle was extended at 72° C. for 5 min. PCR products were diluted in 25 μl of 0.1% SDS, 10 mM EDTA and 25 μl of 95% formamide, 20 mM EDTA, 0.5% bromophenol blue, and 0.5% xylene cyanol. Two conditions for electrophoresis were carried out for each set of reactions. In one, electrophoresis of a 90 mM Tris borate, 2 mM EDTA (pH 7.5) (Gibco, BRL), 35% MDE (AT Biochem) 10% glycerol gel was performed at room temperature, cooled by fans; in the other, electrophoresis of a 90 mM Tris borate, 2 mM (Gibco, BRL), 25% MDE (AT Biochem) gel was performed at 4° C. Electrophoresis was carried out for both conditions at 40W constant power in 0.6×TBE running buffer. After electrophoresis, gels were transferred to 3 MM paper and dried on a vacuum slab dryer. Autoradiography overnight with Kodak XAR5 film without intensifying screens was sufficient to detect bands.

F. DNA Sequencing of SSCP Conformers

Isolation of DNA from SSCP conformers was performed as described previously in Groden et al. (*Cell* 66:589–600 (1991); *Am. J. Hum. Genet.* 52:263–272 (1993)). Each sample was analyzed by agarose gel electrophoresis to confirm the correct size. The remainder of each sample was purified using Centricon 100 columns (Amicon) and sequenced using the dsDNA Cycle Sequencing System (Gibco, BRL) with the forward primer originally designed for SSCP analysis. Sequencing reactions were analyzed by electrophoresis through 5% denaturing polyacrylamide gels. Gels were dried and exposed to Hyperfilm-MP (Amersham) without intensifying screens.

II. Results

Figure 1A:
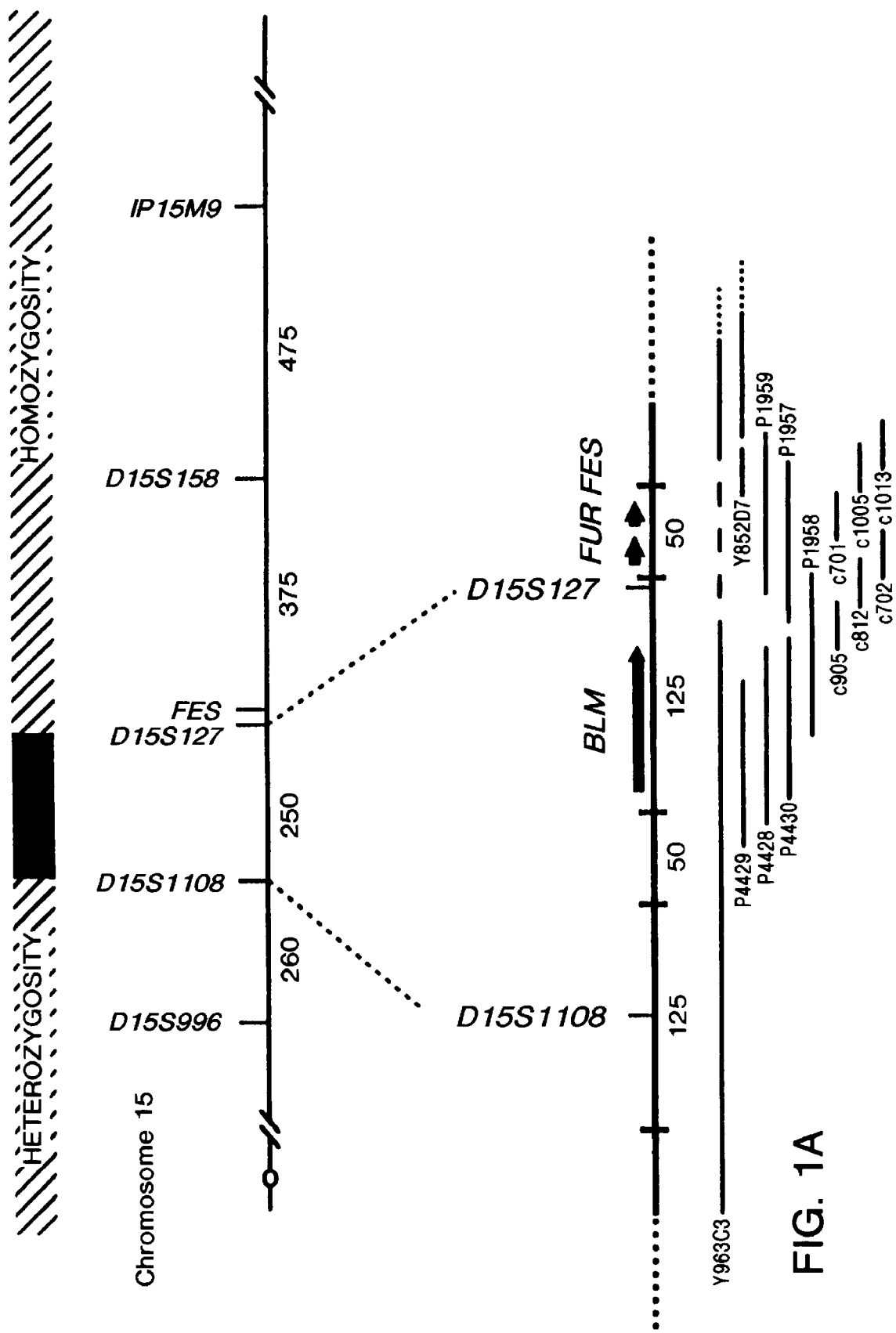
FIG. 1A represents the genetic map of the BLM region of 15q. On the upper horizontal line, the order and distances (shown in kilobase "kb") between the polymorphic microsatellite loci were estimated by long-range-restriction mapping (Straughen, J., et al. Physical mapping of the region containing the Bloom's syndrome gene BLM by the identification of YAC and P1 clones from human chromosome 15. Genomics, 1995, submitted). The distance between D15S127 and FES (not indicated) was determined to be 30 kb by restriction enzyme mapping of a cosmid contig (see below). Vertical lines indicate the position of the marker loci, and the circle represents the centromere. The interval between loci D15S1108 and D15S127 is expanded below the map. Vertical lines intersecting mark the unmethylated CpG-rich regions identified by long-range restriction mapping, and arrows indicate the direction of transcription of three genes in the region. Certain YACs, Pls, and cosmids (Y, P, and c, respectively) from the contig (Straughen, et al., supra) are depicted by horizontal lines underneath the map. Dashes on the YAC lines indicate internal deletions. At the top of the figure, the horizontal cross-hatched bars indicate regions proximal to BLM that remained heterozygous in the low-SCE LCLs and regions distal to BLM that had become homozygous. The minimal region to which BLM was thus assigned by SCP mapping is represented in black.
Figure 1B:
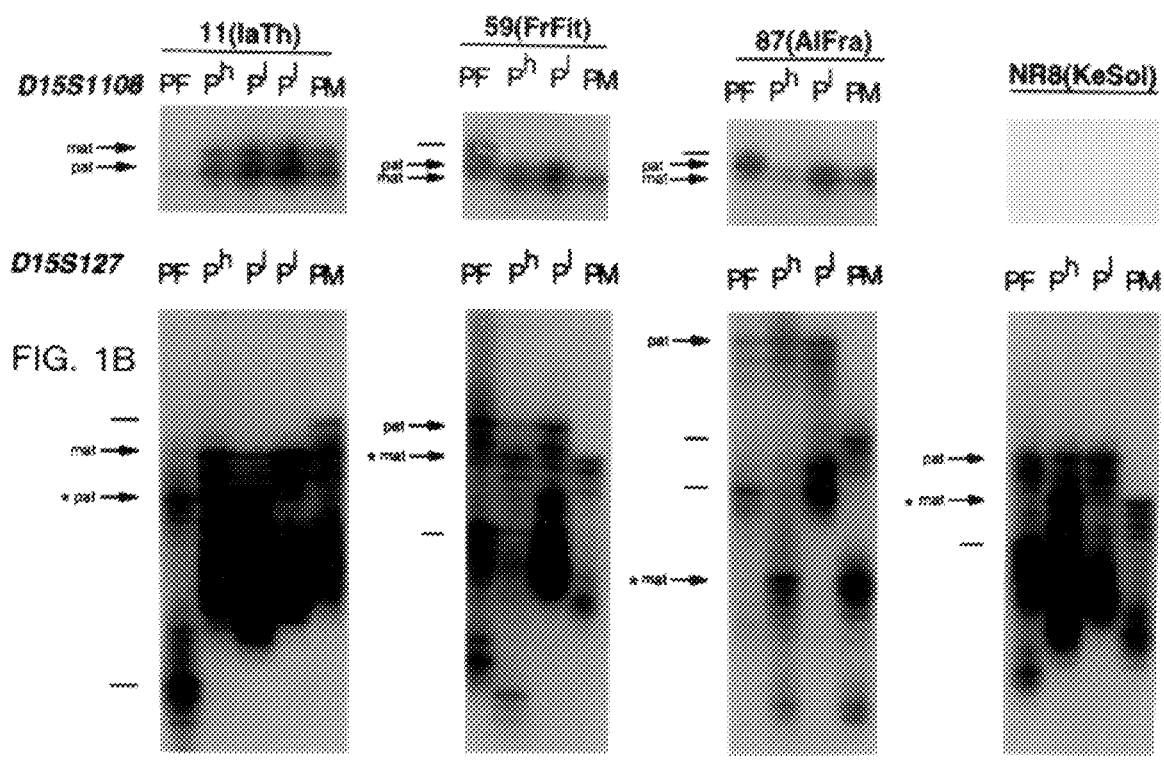
FIG. 1B represents the autoradiographic evidence showing heterozygosity proximal to BLM and reduction to homozygosity distal to BLM. The four persons of five from whom low-SCE LCLs had been established that were informative at D15S1108 or D15S127 are shown. To determine both the constitutional and the recombinant cell line genotypes, PCRs were carried out using DNA samples prepared from high-SCE cells ($p^h$) and low-SCE LCLs ($p^l$)

A. Localization of BLM to a 250-kb Interval BLM previously was localized by SCP mapping to a 1.3 cM interval bounded proximally by D15S116 and distally by four tightly linked loci D15S127, FES, D15S158, and IP15M9 (Ellis, et al., *Am. J. Hum. Genet.*, 1995, supra). The four loci are present in a 1–2 cM interval on chromosome 15 (Beckmann, et al., supra; Gyappay, et al., supra). The order of these four loci was determined by PCR analysis of clones in a 2-Mb YAC and P1 contig that encompasses BLM (Straughen, et al., supra). The four loci were oriented with respect to the telomere by finding a recombinant chromosome in a BS family in which crossing-over had occurred between BLM and IPI5M9, placing IPI5M9 on the distal end of the contig (FIG. 1A). Because D15S127 was the most proximal locus that was reduced to homozygosity in low-SCE LCLs, polymorphic loci in the region proximal to it were sought. There, a polymorphic locus, D15S1108, was identified that remained constitutionally heterozygous in the recombinant low-SCE LCLs, in contrast to locus D15S127 that had become homozygous in them (FIG. 1B). This shift from heterozygosity to homozygosity of markers indicated that BLM is situated in the 250-kb region between D15S1108 and D15S127.

Two genes, FES and FUR, map distal to D15S127 in this region of chromosome 15. SCP mapping thereby eliminated them as candidates for BLM. Consistent with this conclusion, an earlier mutation search in six BS LCLs had failed to uncover mutations in FUR (data not shown).

B. Isolation of a Candidate for BLM cDNAs were isolated from the 250-kb region between D15S1108 and D15S127 by direct cDNA selection using cDNA libraries from cultured fibroblasts and the T-cell line Jurkat. Libraries from these cell lines were chosen because fibroblasts and T lymphocytes from persons with BS exhibit the high-SCE phenotype, indicating that BLM is expressed in these cell types. In direct selection experiments using cosmid c905 (see FIG. 1A), an 847-bp cDNA designated 905-28 was isolated after two rounds of direct selection. It was found in less than 1 in $1\times10^6$ clones screened in the fibroblast library but was present in 6 of 28 selected cDNA clones, a 250,000-fold enrichment. The six cDNAs represented by 905-28 were the only selected cDNAs that by Southern analysis mapped to the BLM region and that identified non-repetitive sequences in the human genome (data not shown). The 905-28 cDNA identified single-copy sequences that are situated approximately 55 kb proximal to FUR (FIG. 1A).

The 905-28 cDNA then was used to screen a HeLa cDNA library. Twenty eight cDNAs were isolated, representing at least 15 distinct classes of overlapping clones. Each of these classes had the same sequence as the 905-28 cDNA at their 3' ends but a different length of 5' sequence. In the longest cDNA isolated, clone H1, a long reading frame was found that was open to the 5' end. Additional sequences upstream of the start of the H1 cDNA were identified by a PCR cloning method (see above). Clones extending 5' of the H1 cDNA were isolated from the HeLa library, permitting the identification of 4,437 bp of sequence, which is referred herein as the H1-5' sequence (FIG. 2).

Starting at the first in-frame ATG 74 bp from its 5' end, the H1-5, sequence encodes a 1,417 amino acid peptide with a predicted molecular weight of 159 kDa. No in-frame stop codons were present between this ATG and the 5' end of the H1-5' sequences. An extensive cDNA analysis was carried out to map the 5' end of the candidate gene. $8\times10^6$ LCL cDNA clones were screened by hybridization with a 5' probe. Eleven clones were isolated, and their 5' ends were sequenced (FIG. 3). In addition, 12 fibroblast clones prepared by a 5' rapid amplification of cDNA ends (RACE) technique were sequenced. Both analyses indicated that the H1-5' sequence is full-length.

The predicted peptide encoded in the H1-5' sequence was used to carry out a BLASTP search of amino acid sequence databases. The searches identified significant homologies to motifs present in the three known peptides in the RecQ subfamily of DExH box-containing helicases (FIG. 4). The amino acid identities were concentrated in the region (residues 649 to 1041) containing the seven conserved helicase domains of the human RECQL (49%), *S. cerevisiae* SGS1 (46%), and *E. coli* recQ (42%) genes. This suggests that the product of the candidate gene is a DNA helicase.

The seven helicase domains identified by their homology to RecQ constitute only the middle third of the predicted peptide. Between residues 588 and 661, amino acid identities were discovered with three short motifs present in a broad phylogenetic spectrum of RNA polymerase II largest subunits (marked by asterisks in FIG. 2). The function of these motifs is unknown. No other significant homologies were identified to amino acid sequences in databases.

The amino-acid composition of the non-helicase regions of the predicted peptide is unusual. The amino-terminal 648 residues of the peptide are rich in acidic (17%), basic (12%), and polar (34%) amino acids; 13% of the residues are serines. Similarly, the carboxy-terminal 376 residues also are rich in acidic (11%), basic (16%), and polar (30%) amino acids; and again, 14% of the residues are serines. The function of these highly charged regions is unknown.

C. RNA Expression of the Candidate Gene in Cultured Cells

Northern blot analysis was used to determine the size of the full-length transcript from the candidate gene. The H1 cDNA was hybridized to total RNAs prepared from HeLa cells, normal diploid cultured fibroblasts, and non-BS LCLs. Two RNA bands at approximately 4.5 kb were visualized on the autoradiogram (FIG. 5A). This size is consistent with the length of the longest cDNAs sequenced (FIG. 2 and 3).

In addition, Northern blot analysis was performed using total RNAs prepared from LCLs from seven unrelated persons with BS (FIG. 5B). In three BS LCLs the quantity of RNAs identified by hybridization to the H1 cDNA was decreased in comparison to that of the control LCLs. In the other four BS LCLs the pattern of RNA mobilizes is aberrant: in one the upper band is missing, in another the lower band is missing, and in remaining two the ratio of the two RNA bands was reversed compared to that in normal cells; i.e., the intensity of the lower of the two bands was increased and the upper decreased in the BS LCLs. The RNA loading was equal in all the lanes as evidenced by hybridization with a probe for the G3PD6 (glyceraldehyde-3-phosphate-dehydrogenase) gene. These observations suggest that RNAs identified by the H1 cDNA might be destabilized in BS LCLs as result of mutations in the candidate gene (see Surdej, P., et al. *Ann. Rev. Genet.* 28:263–282 (1994)).

D. Mutations in the Candidate Gene in Persons With BS

To determine whether the candidate gene is BLM, RNAs were prepared from LCLs from 13 unrelated persons with BS and from cell lines from 4 unaffected controls. These RNAs were used to generate cDNAs for mutational analysis of the expressed sequences of the candidate gene. Sequences in these 13 BS and 4 control non-BS cDNAs were amplified in approximately 200-bp segments using PCR primers designed from the open reading frame in the H1-5' sequence (Table 2). The amplified segments were analyzed by single strand conformation polymorphism (SSCP) analysis using two conditions for electrophoresis. Novel SSCP conformers (FIG. 6) were identified, and the genetic changes underlying them were sequenced (Table 1).

Seven unique mutations were identified in 10 persons with BS (the boxed and diamond-marked nucleotides in FIG. 2), as well as four polymorphic base pairs which will not be described here. Four of the mutations introduced premature nonsense codons into the coding sequence, and three introduced amino acid substitutions (see below). One of the four chain-terminating mutations arose by a 3-bp deletion, one by a nucleotide substitution, one by a 1-bp insertion that caused a frameshift, and one by a 6-bp deletion accompanied by a 7-bp insertion that also caused a frameshift. This last mutation was detected in all four persons with Ashkenazi Jewish ancestry. The potential products encoded in these four mutant alleles are 185, 271, 515, and 739 amino acids in length, respectively, and none contains a complete set of the 7 helicase domains. Three of these mutant alleles were detected in the homozygous state, indicating that the persons inheriting them in double dose probably have no active BLM gene product in their cells. These observations are evidence that the H1-5' sequences are mutated in persons with BS, thereby proving that the candidate gene is BLM.

Finally, two putative missense mutations were identified in two persons with BS that introduced amino acid substitutions at residues conserved in RecQ helicases (residues with asterisks in FIG. 4), and one was identified that introduced an amino acid substitution of cysteine to serine in the C-terminal region of the peptide. Because the three genetic alterations could be polymorphisms and the actual BS-associated mutations could have gone undetected, analyses of the BLM gene product in vitro will be required to demonstrate whether these substitutions cause the mutant phenotype.

III. Discussion

In the present study, BLM was isolated by a positional cloning strategy. BLM first was localized by homozygosity mapping to a 2-cM interval flanking FES (German, et al., 1994, supra), a gene already mapped to chromosome band 15q26.1. A 2-Mb YAC and P1 contig encompassing FES was constructed, and closely spaced polymorphic DNA markers in the contig were identified (Straughen, et al., supra). BLM then was assigned by SCP mapping to a 250-kb interval in the contig, one bounded by the polymorphic loci D15S1108 and D15S127 (FIG. 1). A cDNA clone (905-28) was isolated by direct cDNA selection using a cosmid clone from the interval, and cDNA analysis identified the 4,437-bp H1-5' sequence (FIG. 2). This sequence encodes a putative peptide homologous to the RecQ helicases (FIG. 4). RNA transcripts 4.5-kb long were identified by Northern blot analysis (FIG. 5A), and electrophoretic abnormalities in RNAs were detected in cells from seven unrelated persons with BS, suggesting that these RNAs are derived from mutant BLM genes (FIG. 5B). Finally, RT-PCR/SSCP analysis disclosed 7 unique mutations in 10 persons with BS (Table 1; FIG. 6), 4 that are chain-terminating and 3 that are putative missense substitutions, 2 of the 3 affecting amino acid residues conserved in RecQ helicases and the third changing a cysteine to a serine.

A. SCP Mapping, a Powerful New Strategy

In a recent tabulation of the 42 inherited disease-associated genes isolated by positional cloning (Collins, F. *Nature Genetics* 9:347–350 (1995)) 19 were transmitted as autosomal dominants and 17 as X-linked recessives; however, only 5 were autosomal recessives. The reasons for the paucity of positionally cloned autosomal recessive disease-associated genes are at least twofold. First, the cloning of over half of the genes (26 of the 42 tabulated) was aided by chromosome breakpoints within or near the disease-associated gene; however, only one of these was in an autosomal recessive. Secondly, and of greater importance, the number of families transmitting rare autosomal recessive disease-associated genes generally is small, and the number of persons in sibships who would be informative in recombinational analysis also is small. Because a single investigator usually cannot obtain the numbers of families required for linkage analysis, the localization and subsequent positional cloning of rare autosomal recessive genes has lagged behind that of dominant and X-linked recessive genes.

Even when samples from numerous families have been collected and analyzed, usually the amount of positional information obtained is limited. In the case of BS, the Bloom's Syndrome Registry (German and Passarge, supra), a research resource that has provided the material for all of the inventors' recent genetical studies, made possible an extensive recombinational analysis of BLM by homozygosity mapping. This analysis permitted a minimum regional assignment of BLM to approximately 1.4 Mb (unpublished results). This size of minimum interval is typical of recombinational analysis. A search for and subsequent mutational analysis of genes from a 1.4-Mb region would have been laborious.

The problem of too little positional information in available families can be mitigated in exceptional situations in which linkage disequilibrium between the disease-associated gene and tightly-linked polymorphisms can be detected in a genetic isolate. In these cases localization of a gene to a short interval in the genome by haplotype analysis can be more exact than is possible using standard linkage analysis of family data (e.g., Kerem, B.-S., et al. *Science* 245:1073–1080 (1989); Sirugo, G., et al. *Am. J. Hum. Genet.* 50:559–566 (1992); Lehesjoki, A. E., et al. *Hum. Mol. Genet.* 2:1229–1234 (1993); Hastbacka, J., et al. *Cell* 78:1073–1087 (1994)). Linkage disequilibrium in fact was a strategy available in BS (Ellis, et al., *Am. J. Hum. Genet.*, 1994, supra), and it permitted a minimum regional assignment of BLM to the same 250-kb interval described herein (Ellis, et al., Linkage-disequilibrium mapping permits assignment of the Bloom's syndrome gene BLM to a 250-kb genomic DNA segment on chromosome 15. *Genomics*, submitted). This approach could have allowed the inventors to clone BLM. Instead, the inventors carried out SCP mapping first.

In the SCP-mapping strategy, the inventors took advantage of recombinant cell lines from BS somatic cells in which crossing-over within BLM had taken place, resulting in the correction of the mutant phenotype in their progenies (Ellis, et al., *Am. J. Hum. Genet.*, 1995, supra). After a segregational event, all polymorphic loci distal to BLM were reduced to homozygosity in half of the cases of intragenic recombination. This mapping method was preferred to linkage-disequilibrium mapping because the crossovers that permitted localization of BLM had occurred within the gene itself and fewer genotypes were required for the analysis. By genotyping polymorphic loci that flank BLM in high-SCE and low-SCE samples from only five persons with BS and their parents, the position of BLM was delimited to the short interval bounded by the marker loci D15S1108 and D15S127 (FIG. 1). With BLM assigned to such a short interval the cloning of BLM became straightforward. The first candidate gene isolated from the interval proved to be BLM.

B. Loss-of-Function Mutations at BLM

The candidate gene for BLM isolated from the interval identified by SCP mapping encodes a 1,417 amino acid peptide, previously unrecognized but homologous to RecQ helicases. Mutational analysis of the first 13 unrelated persons with BS examined permitted the identification of 7 unique mutations in 10 of them (Table 1). The fact that four of the seven mutations characterized so far result in premature termination of translation indicates that the cause of most BS is the loss of enzymatic activity of the BLM gene product. Identification of loss-of-function mutations in BLM (Table 1) is consistent with the autosomal recessive transmission of BS, and the homology of BLM and RecQ suggests that BLM has enzymatic activity. Thus, it is predicted that most BS mutations result in loss of function of BLM.

This loss of enzymatic activity is not lethal in cells, because three of the chain-terminating mutations were detected in a homozygous state. The non-lethality could result from the existence of some residual enzymatic activity in the truncated peptides; however, this seems unlikely because one of the homozygous chain-terminating mutations results in chain termination after only 185 amino acids in a person with typical BS. Alternatively, the function of BLM may not be essential for cell survival. Other factors in the cell may be able to substitute for BLM, albeit inefficiently.

In the four persons with Jewish ancestry, 6-bp deletion/7-bp insertion at nucleotide 2,281 was identified and each of the four persons was homozygous for the mutation. Homozygosity was predictable because linkage disequilibrium had been detected in Ashkenazi Jews with BS between BLM, D15S127, and FES (Ellis, et al., *Am. J. Hum. Gen.*, 1994, supra). Thus, a person who carried this 6-bp deletion/7-bp insertion was a founder of the Ashkenazi Jewish population, and nearly all Ashkenazi Jews with BS inherit the mutation identical by descent from this common ancestor. Identification of the mutation now permits the screening of carriers in the Ashkenazim by a simple PCR test.

BS is an autosomal recessive with high penetrance and expressivity. The observation of loss-of-function mutations in BLM helps to explain these genetic characteristics. The short stature, characteristic facies, facial sun-sensitivity, hyper- and hypopigmented patches on the skin, immunodeficiency, male infertility, female subfertility, premature menopause, and the predispositions to late-onset diabetes and to neoplasia exist in virtually all groups of persons with the syndrome. The BS phenotype is similar in the Ashkenazi Jews, the Dutch, Flemish, German, Italian, Greek, Turkish, and Japanese—i.e., wherever it's been diagnosed. In addition, the elevated chromatid exchange and the hypermutability are constant cellular manifestations. No more variability in the expressivity of the mutations has been detected in persons with BS who inherit an identical mutation by descent from a common ancestor, as happens in Ashkenazi Jews with BS and in the 25% of non-Ashkenazi Jewish persons with BS whose parents are cousins, than has been detected in persons who are compound heterozygotes (German et al., 1995, supra). Nevertheless, with BLM cloned, it is possible to identify the mutations in any person with BS, and more subtle genotype-phenotype correlations now can be carried out.

C. BLM as a Putative DNA Helicase

The BLM gene product has been shown to be homologous at the amino acid level to the RecQ helicases (FIG. 4), a subfamily of DExH box-containing DNA and RNA helicases. RecQ is an *E. coli* gene which is a member of the RecF recombination pathway (Nakayama, H., et al. *Mol. Gen. Genet.* 195:474–480 (1984)), a pathway of genes in which mutations abolish the conjugational recombination proficiency and UV-resistance of a mutant strain lacking both the RecBCD (part of exonuclease V) and the SbcB (exonuclease I) activities (Horii, Z., and Clark, A. J. *J. Mol. Biol.* 80:327–344 (1973)). RecQ has DNA-dependent ATPase and DNA helicase activities and can translocate on single-stranded DNA in a 3'-5' direction (Umezu, K., et al. *Proc. Natl. Acad. Sci. USA* 87:5363–5367 (1990)). Besides BLM, only two other recQ-like genes are known. First, SGS1 is a yeast gene in which mutations suppress the slow growth of cells carrying mutations in the TOP3 topoisomerase gene (Gangloff, S., et al. *Mol. Cel. Biol.* 14:8391–8398 (1994)). It also was isolated in a yeast two-hybrid screen through its interactions with both the yeast Top2 and Top3 topoisomerases (Gangloff, et al., supra; Watt, P. M., et al. *Cell* 81:253–260 (1995)). Secondly, REQL is a human gene isolated from HeLa cells the product of which possesses DNA-dependent ATPase, DNA helicase, and 3'-5' single-stranded DNA translocation activities (Puranam, K. L., and Blackshear, P. J. *J. Mol. Biol.* 47:29838–29845 (1994); Seki, M., et al. *Nucl. Acids Res.* 22:4566–4573 (1994)). The homology of BLM with RecQ and RECQL strongly suggests that BLM also has DNA-dependent ATPase and DNA helicase activities, and studies to investigate this have been initiated.

In addition to helicase domains, BLM contains N-terminal and C-terminal regions that are composed predominantly of charged and polar amino acid residues. The presence of non-helicase regions in BLM raises the possibility of additional enzymatic activities. The non-helicase regions could operate to provide functional specificity to BLM, e.g., by promoting interactions with other proteins, or could provide substrates for phosphorylation that might regulate BLM activity in the cell cycle.

D. A Function for BLM in DNA Replication

Some genes in the DExH family have been implicated in DNA repair, and mutations in three of them, the XPB, XPD, and ERCC6 genes, have been identified in the human disease phenotypes xeroderma pigmentosum and Cockayne's syndrome (Weber, C. A., et al. *EMBO J.* 9:1437–1447 (1990); Frejter, W. L., et al. *Proc. Natl. Acad. Sci. USA* 89:261–265 (1992); Troelstra, C., et al. *Cell* 71:939–953 (1992); Sung, P., et al. *Nature* 365:852–855 (1993); Ma, L., et al. *Mol. Cell. Biol.* 14:4126–4134 (1994)). A universal function for the RecQ helicases, however, is not established. No abnormality in humans has been attributed to defects in RECQL. Even the cellular function of RecQ in bacteria is unclear, although it most likely participates in an aspect of post-replication recombinational repair (Luisi-DeLuca, C., et al. *Genetics* 122:269–278 (1989); Kusano, K., et al. *Proc. Natl. Acad. Sci. USA* 91:1173–1177 (1994); Tseng Y.-C., et al. *Mutation Res.* 315:1–9 (1994)). The phenotype of yeast SGSI mutants includes slow growth, poor sporulation, chromosome nondisjunction at mitosis, missegregation in meiosis (Watt, et al., supra), and an elevated recombination frequency (Gangloff, et al., supra). SGS1 is known to interact with topoisomerases II and TOP3, and therefore may function in chromosome separation, a process in which intertwined DNA strands are resolved when replication forks converge. The predicted sizes of BLM (1,417 residues) and SGS1 (1,447 residues) are similar, the two peptides have similar base-compositions outside the helicase domains, and mutations in the genes encoding them result in genomic instability. In addition, an interaction between BLM and topoisomerase II in human cells has been suggested by the observation that topoisomerase II activity is decreased in BrdU-treated BS cells (Heartlein, M. W., et al. *Exp. Cell Res.* 169:245–254 (1987)). Although these interesting similarities are inconclusive, the possible functional homology between BLM and SGS1 warrants further investigation.

In general, BLM has been implicated in the complex processes of DNA replication. Mutations in BLM have impressively pleiotropic cytogenetic and biochemical consequences. The chromosome breaks, gaps, and translocations and the high frequency of intra- and interchromosomal strand exchanges all point to a disturbance of DNA replication. In BS cells, the rate of nascent DNA chain-elongation is retarded (Hand, R., and German, *J. Proc. Natl. Acad. Sci. U.S.A.* 72:758–762 (1975); Giannelli, F., et al. *Nature* 265:466–469 (1977)), and the distribution of DNA replicational intermediates is abnormal (Lonn, U., et al. *Cancer Res.* 50:3141–3145 (1990)). Some though not all cultured BS cells exhibit increased sensitivity to DNA-damaging agents, e.g. UV radiation, mitomycin C, N-nitroso-N-ethylurea, and ethyl methanesulfonate (Krepinsky, A. B., et al. *Hum. Genet.* 50:151–156 (1979); Krepinsky, A. B., et al. *Mutation Res.* 69:357–368 (1980); Ishizaki, K., et al. *Mutation Res.* 80:213–219 (1981); Heddle, J. A., et al. (1983) Cellular sensitivity to mutagens and carcinogens in the chromosome-breakage and other cancer-prone syndromes. In Chromosome Mutation and Neoplasia, J. German, ed. (Alan R. Liss, Inc., New York), pp.203–234; Kurihara, T., et al. *Mutation Res.* 184:147–151 (1987)). Disturbances in several enzymes that participate in DNA replication, DNA repair, or both have been identified in some though, again, not all BS cell lines, including DNA ligase I (Chan, J. Y. H., et al. *Nature* 325:357–359 (1987); Willis, A. E. and Lindahl, T. *Nature* 325:355–357 (1987)), topoisomerase II in BrdU-treated BS cells (Heartlein, et al., supra), thymidylate synthetase (Shiraishi, Y., et al. *Mutation Res.* 211:273–278 (1989)), uracil DNA glycosylase (Seal, G., et al. *Proc. Natl. Acad. Sci. U.S.A.* 85:2339–2343 (1988)), N-methylpurine DNA glycosylase (Dehazya, P., and Sirover, M. A. *Cancer Res.* 46:3756–3761 (1986)), $O^6$-methylguanine methyltransferase (Kim, S., et al. *Mutation Res.* 173:141–145 (1986)), and superoxide dismutase (Nicotera, T. M., et al. *Cancer Res.* 49:5239–5243 (1989)). These investigations show that certain enzymes concerned with DNA replication and, or, repair appear to be dysregulated in BS and that cultured BS cells make variously abnormal responses to DNA-damaging agents.

The evidence that BS cells have a defect in DNA repair, however, is slight (Friedberg E. C., et al. *Adv. Rad. Biol.* 8:85–174 (1979); German, J, and Schonberg, S. (1980) Bloom syndrome. IX. Review of cytological and biochemical aspects. In Genetic and Environmental Factors in Experimental and Human Cancer, H. V. Gelboin, B. MacMahon, T. Matsushima, T. Sugimura, S. Takayama, and H. Takebe (eds.) (Japan Scientific Societies Press, Tokyo) pp 175–186). BS cells are not hypersensitive to UV or X-ray irradiation by standard assays, and no defect in a specific DNA-repair enzyme or pathway has been reported. Although the explanation for the pleiotropic effects of BS mutations still is unknown, the predicted function of BLM as a DNA helicase implies that the BS cell encounters greater difficulties than the normal in the resolution of specific DNA structures generated during DNA replication. BLM presumably is one member of an assembly of gene products that acts in a pathway to resolve these structures. The excessive rates of chromatid exchange (homologous chromatid interchange configurations at metaphase and the SCE rates) might be microscopically visible manifestations of repair processes that are activated by the mutant cell's inability to resolve the structures properly. Identification of the substrates on which BLM operates represents one of the important areas for future investigation.

IV. Conclusions

With the cloning of the BS gene and the inference that its gene product is a DNA helicase, new insight has been gained into the molecular basis of the genomic instability which is the most impressive feature of BS cells. The absence of the BLM gene product most likely destabilizes other enzymes that participate in DNA replication and repair, perhaps through direct interactions or through more general responses to DNA damage. Elucidation of the enzymatic activities of BLM, the factors with which it interacts, and the substrates on which it operates now are required in order to understand the role of BLM in the maintenance of genomic stability, and may play a role in cancer diagnosis and therapy in the population at large.

| | | | | Mutation | | | | |
|---|---|---|---|---|---|---|---|---|
| | try | Cell line | Position[b] (bp) | Alteration[c] | Zygosity at BLM[d] | Kind | Codon change | Predicted peptide[e] |
| 97(AsOk) | Japanese | HG1926 | 631 | 3-bp del[f] | Homo | Nonsense | S→stop | 185 |
| 112(NaSch) | German | HG2510 | 888 | A→T | Hetero | Nonsense | K→stop | 271 |
| 93(YoYa) | Japanese | HG1626 | 1610 | 1 bp ins | Homo | Frameshift[g] | | 515 |
| 139(ViKre) | American/European | HG2231 | 2089 | A→G | Hetero | Missense | Q→R[g] | 1417 |
| 15(MaRo) | Ashkenazi Jewish | HG1514 | 2281 | 6 bp del/ 7 bp ins | Homo | Frameshift[i] | | 739 |
| 42(RaFr) | Ashkenazi Jewish | HG2522 | 2281 | 6 bp del/ 7 bp ins | Homo | Frameshift[i] | | 739 |
| 107(MyAsa) | Ashkenazi Jewish | HG2654 | 2281 | 6 bp del/ 7 bp ins | Homo | Frameshift[i] | | 739 |
| NR2(CrSpe) | Ashkenazi Jewish | HG2727 | 2281 | 6 bp del/ 7 bp ins | Homo | Frameshift[i] | | 739 |
| 92(VaBi) | Italian | HG1584 | 2596 | T→C | Homo | Missense | I→T[j] | 1417 |
| 113(DaDem) | Italian | HG1624 | 3238 | G→C | Homo | Missense | C→S[k] | 1417 |

[a]Bloom's Syndrome Registry designations. Three unrelated persons with BS were examined in whom mutations have yet to be detected: 61(DoHo), in HG2122; 30(MaKa), in HG1987; 140(DrKas), in HG1972.
[b]The nucleotide positions are as identified in the H1-5' sequence (FIG 2).
[c]Del, deletion; ins, insertion.
[d]Homo, homozygous; hetero, heterozygous.
[e]Number of amino acids starting from the first in-frame ATG found in the H1-5' sequence (FIG. 2).
[f]The deletion of CAA at nucleotide positions 631–633 results in a stop codon at amino acid position 186 (FIG. 2).
[g]The insertion of an A bp causes the insertion of a novel codon for K after amino acid 514 position (taken from the H1-5' sequence, FIG. 2), and after this codon there is a stop codon.
[h]At amino acid position 672.
[i]The deletion of ATCTGA and insertion of TAGATTC causes the insertion of the novel condons for LDSR after amino acid position 736, and after these codons there is a stop codon.
[j]At amino acid position 843.
[k]At amino acid position 1055

TABLE 2

Pairs of primer sequences used for SSCP analysis of BLM.

| Name | Forward sequence[a] | SEQ. ID. NO. | Reverse sequence[a] | SEQ. ID. NO. | Product length (bp) |
|---|---|---|---|---|---|
| C1-B | GGATCCTGGTTCCGTCCGC | (10) | GAGGTTCACTGAAGGAAAAGTC | (26) | 269 |
| C1-A | CAACTAGAACGTCACTCAGCC | (11) | GAAGTCCTTGACCCTTTGCTG | (27) | 233 |
| C1-1 | GACTTTTCCTTCAGTGAACCTC | (12) | GGGATTTCTTTACAGTTGGTGTG | (28) | 186 |
| C1-2 | CCAGATTTCTTGCAGACTCCG | (13) | CTCTTACAAAGTGACTTTGGGG | (29) | 213 |
| C1-3 | CTTTAAGTACCATCAATGATTGGG | (14) | CCTCAGTCAAATCTATTTGCTCG | (30) | 227 |
| C1-4 | GAGTAAGCACTGCTCAGAAATC | (15) | GCTTAACCATTCTGAGTCATCC | (31) | 160 |
| C1-5 | CGAGCAAATAGATTTGACTGAGG | (16) | CAATACATGGAACTTTCTCAGTTG | (32) | 223 |
| C1-6 | GAAGATGCTCAGGAAAGTGAC | (17) | CGTACTAAGGCATTTTGAAGAGG | (33) | 215 |
| C1-7 | CAACTGAGAAAGTTCCATGTATTG | (18) | CACAGTCTGTGCTGGTTTCTG | (34) | 239 |
| C1-9 | CTATTCCTGATGATAAACTGAAAC | (19) | CCTTCATAGAATTCCCTGTAGG | (35) | 200 |
| C1-10 | GTGGAGATACAGGCCTGATTC | (20) | GTGTTTCAGCCCAGTTGCTAC | (36) | 244 |
| C1-11 | CAGGATTCTCTGCCACCAGG | (21) | GCAGTATGTTTATTCTGATCTTTC | (37) | 183 |
| C1-12 | CAGGAAATGTTCTCACAAGCAC | (22) | CCTTGATGGGTTGATAGGCAG | (38) | 203 |
| C1-13 | CAGCCAGCAAATCTTCCACAG | (23) | CGCTCATGTTTCAGATTTCTGG | (39) | 204 |
| C1-14 | GAATTATACTGACAAGTCAGCAC | (24) | GATCTACGATAAGTGATCTCAAG | (40) | 295 |
| C1-15 | CTCCTGGGGTCACTGTTGTC | (25) | GAGTCTGTTACTTGCACAGATC | (41) | 211 |
| C1-16 | CAATCATAAAACTTCTATATGTCAC | (42) | GCCATCACCGGAACAGAAGG | (57) | 207 |
| C1-17 | GTGGGGACATGATTTTCGTCAAG | (43) | GATTATGTCTGTTAAAGCTCATG | (58) | 175 |
| C1-18 | GACATCCTGACTCAGCTGAAG | (44) | CGTGTCAGCCATGGTGTCAC | (59) | 203 |
| C1-19 | GCACCACCCATATGATTCAGG | (45) | CAGATAACCTGACAGCCATCC | (60) | 179 |
| C1-20 | GATGAAGTGCAGCAGAAGTGG | (46) | CAGTCTGGTCACATCATGATAG | (61) | 221 |
| C1-21 | GCAGAGCTGGAAGAGATGGG | (47) | GCTGTATTCTCCTGCATTCCG | (62) | 188 |
| C1-22 | GTATAGCATGGTACATTACTGTG | (48) | CCTTGTGATGAACTATGTTCTTG | (63) | 228 |
| C1-23 | GACTGACGATGTGAAAAGTATTG | (49) | CCAAAATCTTGTCAAGTATCAGC | (64) | 235 |
| C1-24 | CCAGTCAGGTATATTTGGAAAAG | (50) | GGAATTTTCTGTTTCCATAAAGTC | (65) | 206 |
| C1-25 | CGATCGCTTATGTGATGCTCG | (51) | CAAGCTTCTTGAGAGTGACGG | (66) | 248 |
| C1-26 | GAACTTACAGAAGTCTGCAAATC | (52) | GATGTCCATTCAGAGTATTTCTG | (67) | 208 |
| C1-27 | GGTGTTACTGAAGACAAACTGG | (53) | GGGTATTTCCTCGTCAAGCTC | (68) | 168 |
| C1-28 | GGATAAGCCTGTCCAGCAGC | (54) | CCTAGATATCTTTCTACATGTGG | (69) | 214 |
| C1-29 | GCTTCCAGTGGTTCCAAGGC | (55) | GTTATGAGAATGCATATGAAGGC | (70) | 204 |
| C1-30 | CTCAAGCGACATCAGGAGCC | (56) | CAAGAATAACAGCTTTATAGTCAC | (71) | 178 |

[a] 5' to 3'

All publications mentioned hereinabove are hereby incorporated by reference in their entirety.

While the foregoing invention has been described in some detail for purposes of clarity and understanding, it will be appreciated by one skilled in the art from a reading of the disclosure that various changes in form and detail can be made without departing from the true scope of the invention in the appended claims.

---

What is claimed is:

1. A purified and isolated nucleic acid encoding the amino acid sequence shown in FIG. 2 (SEQ. ID. NO. 78).

2. A vector comprising the nucleic acid of claim 1.

3. An isolated cell transformed with the vector of claim 2.

4. A method for producing a recombinant protein comprising the amino acid sequence shown in FIG. 2 (SEQ ID NO: 78), said method comprising culturing the cell of claim 3, wherein the recombinant protein is produced, and recovering the protein from the culture.

5. A purified and isolated wild type nucleic acid encoding a human functional variant of the amino acid sequence shown in FIG. 2 (SEQ. ID. NO. 78), said nucleic acid mapping between loci D15S1108 and D15S127 of human chromosome 15.

6. A vector comprising the nucleic acid of claim 5.

7. An isolated cell transformed with the vector of claim 5.

8. A method for producing a recombinant protein comprising the human functional variant of the amino acid sequence shown in FIG. 2 (SEQ ID NO: 78), said method comprising culturing the cell of claim 7, wherein the recombinant protein is produced, and recovering the protein from the culture.

9. A purified and isolated nucleic acid encoding a gene product that is not expressed in a Bloom's syndrome patient, said nucleic acid comprising the nucleotide sequence of FIG. 2 (SEQ. ID. NO. 72).

10. A vector comprising the nucleic acid of claim 9.

11. An isolated cell stably transformed with the vector of claim 10.

12. A method for producing a recombinant protein encoded by said nucleic acid comprising the nucleotide sequence shown in FIG. 2 (SEQ ID NO:72), said method comprising culturing the cell of claim 11, wherein the recombinant protein is produced, and recovering the protein from the culture.

13. A purified and isolated nucleic acid containing at least one mutation that results in an aberrant gene product that is expressed in a Bloom's syndrome patient, said nucleic acid corresponding to a mutated form of: (i) nucleic acid encoding the amino acid sequence shown in FIG. 2 (SEQ. ID. NO. 78) or (ii) wild type nucleic acid encoding a human functional variant of the amino acid sequence shown in FIG. 2 (SEQ. ID. NO. 78), said isolated nucleic acid mapping between loci D15S1108 and D15S127 of human chromosome 15.

14. A vector comprising the nucleic acid of claim 13.

15. An isolated cell stably transformed with the vector of claim 14.

* * * * *